US012582336B2

(12) United States Patent
Kitamura et al.

(10) Patent No.: US 12,582,336 B2
(45) Date of Patent: Mar. 24, 2026

(54) DETECTION DEVICE

(71) Applicant: Magnolia White Corporation, Tokyo (JP)

(72) Inventors: Ayato Kitamura, Tokyo (JP); Yuta Haga, Tokyo (JP)

(73) Assignee: Magnolia White Corporation, Tokyo (JP)

( * ) Notice: Subject to any disclaimer, the term of this patent is extended or adjusted under 35 U.S.C. 154(b) by 539 days.

(21) Appl. No.: 18/102,935

(22) Filed: Jan. 30, 2023

(65) Prior Publication Data

US 2023/0240567 A1 Aug. 3, 2023

(30) Foreign Application Priority Data

Feb. 1, 2022 (JP) ................................. 2022-014396

(51) Int. Cl.
*A61B 5/1455* (2006.01)

(52) U.S. Cl.
CPC .... *A61B 5/14552* (2013.01); *A61B 2562/043* (2013.01)

(58) Field of Classification Search
CPC .................................................. A61B 5/1455
See application file for complete search history.

(56) References Cited

U.S. PATENT DOCUMENTS 7,355,688 B2 * 4/2008 Lash .................. A61B 5/14552
356/213
2023/0015361 A1 1/2023 Kato et al.

FOREIGN PATENT DOCUMENTS

| JP | 2008-242617 A | 10/2008 |
| JP | 2019-180861 A | 10/2019 |
| JP | 2021-157657 A | 10/2021 |

OTHER PUBLICATIONS

Office Action issued in related Japanese Patent Application No. 2022-014396, mailed on May 27, 2025 and English translation of same. 6 pages.

* cited by examiner

*Primary Examiner* — Marjan Fardanesh
(74) *Attorney, Agent, or Firm* — K&L Gates LLP

(57) ABSTRACT

According to an aspect, a detection device includes: a first light source configured to emit light having a predetermined wavelength; a second light source configured to emit light having a wavelength different from that of light emitted by the first light source; optical sensors provided at different locations from each other and configured to measure the light emitted by the first light source and the second light source; a light quantity controller configured to set a light quantity of at least one of the first light source or the second light source so that a measurement value based on at least one of detection values of the optical sensors reaches a predetermined target value; and a biometric information detector configured to, when the measurement value has reached the predetermined target value, detect information on a living body with the optical sensors using the set light quantity for detecting biometric information.

16 Claims, 35 Drawing Sheets

| Raw (1) <1, 1> | Raw (1) <2, 1> | ... | Raw (1) <M, 1> |
|---|---|---|---|
| Raw (1) <1, 2> | Raw (1) <2, 2> | ... | Raw (1) <M, 2> |
| : | : | Raw (1) <m, n> | : |
| Raw (1) <1, N> | Raw (1) <2, N> | ... | Raw (1) <M, N> |

| Raw (2) <1, 1> | Raw (2) <2, 1> | ... | Raw (2) <M, 1> |
|---|---|---|---|
| Raw (2) <1, 2> | Raw (2) <2, 2> | ... | Raw (2) <M, 2> |
| : | : | Raw (2) <m, n> | : |
| Raw (2) <1, N> | Raw (2) <2, N> | ... | Raw (2) <M, N> |

:

| Raw (F) <1, 1> | Raw (F) <2, 1> | ... | Raw (F) <M, 1> |
|---|---|---|---|
| Raw (F) <1, 2> | Raw (F) <2, 2> | ... | Raw (F) <M, 2> |
| : | : | Raw (F) <m, n> | : |
| Raw (F) <1, N> | Raw (F) <2, N> | ... | Raw (F) <M, N> |

DETECTION DEVICE

CROSS-REFERENCE

This application claims the benefit of priority from Japanese Patent Application No. 2022-014396 filed on Feb. 1, 2022, the entire contents of which are incorporated herein by reference.

BACKGROUND

1. Technical Field

What is disclosed herein relates to a detection device.

2. Description of the Related Art

Detection devices are known that emit light into a body through the skin and acquire an oxygen saturation level in blood (hereinafter, called "blood oxygen saturation level" (SpO$_2$)) based on transcutaneous data acquired by detecting light transmitted through or reflected by arteries. The blood oxygen saturation level (SpO$_2$) refers to a ratio of an amount of oxygen actually bound to hemoglobin to the total amount of oxygen under the assumption that the oxygen is bound to all the hemoglobin in the blood. When acquiring the blood oxygen saturation level (SpO$_2$), for example, a pulse wave acquired by infrared light and a pulse wave acquired by red light are used (refer to Japanese Patent Application Laid-open Publication No. 2019-180861, for example).

Before measuring the blood oxygen saturation level (SpO$_2$), the light quantity of a light source needs to be initialized. Unless the light quantity is properly initialized, highly accurate data may not be acquired.

For the foregoing reasons, there is a need for a detection device capable of acquiring highly accurate data.

SUMMARY

According to an aspect, a detection device includes: a first light source configured to emit light having a predetermined wavelength; a second light source configured to emit light having a wavelength different from that of the light emitted by the first light source; a plurality of optical sensors provided at different locations from each other and configured to measure and detect the light emitted by the first light source and the second light source; a light quantity controller configured to set a light quantity of at least one of the first light source or the second light source so that a measurement value based on at least one of detection values of the optical sensors reaches a predetermined target value; and a biometric information detector configured to, when the measurement value has reached the predetermined target value, detect information on a living body with the optical sensors using the light quantity for detecting biometric information set by the light quantity controller.

BRIEF DESCRIPTION OF THE DRAWINGS

FIG. 5B is a sectional view illustrating a schematic sectional configuration of the sensor of a detection device according to a first modification;

FIG. 14 is a timing waveform chart illustrating the operation example of the detection device according to the embodiment;

FIG. 24 is a plan view explaining the initialization performed by the configuration illustrated in FIG. 23;

FIG. 33 is a chart illustrating detection values for F frames in the respective partial detection areas in the detection area that are temporarily stored in a storage;

DETAILED DESCRIPTION

Figure 1:
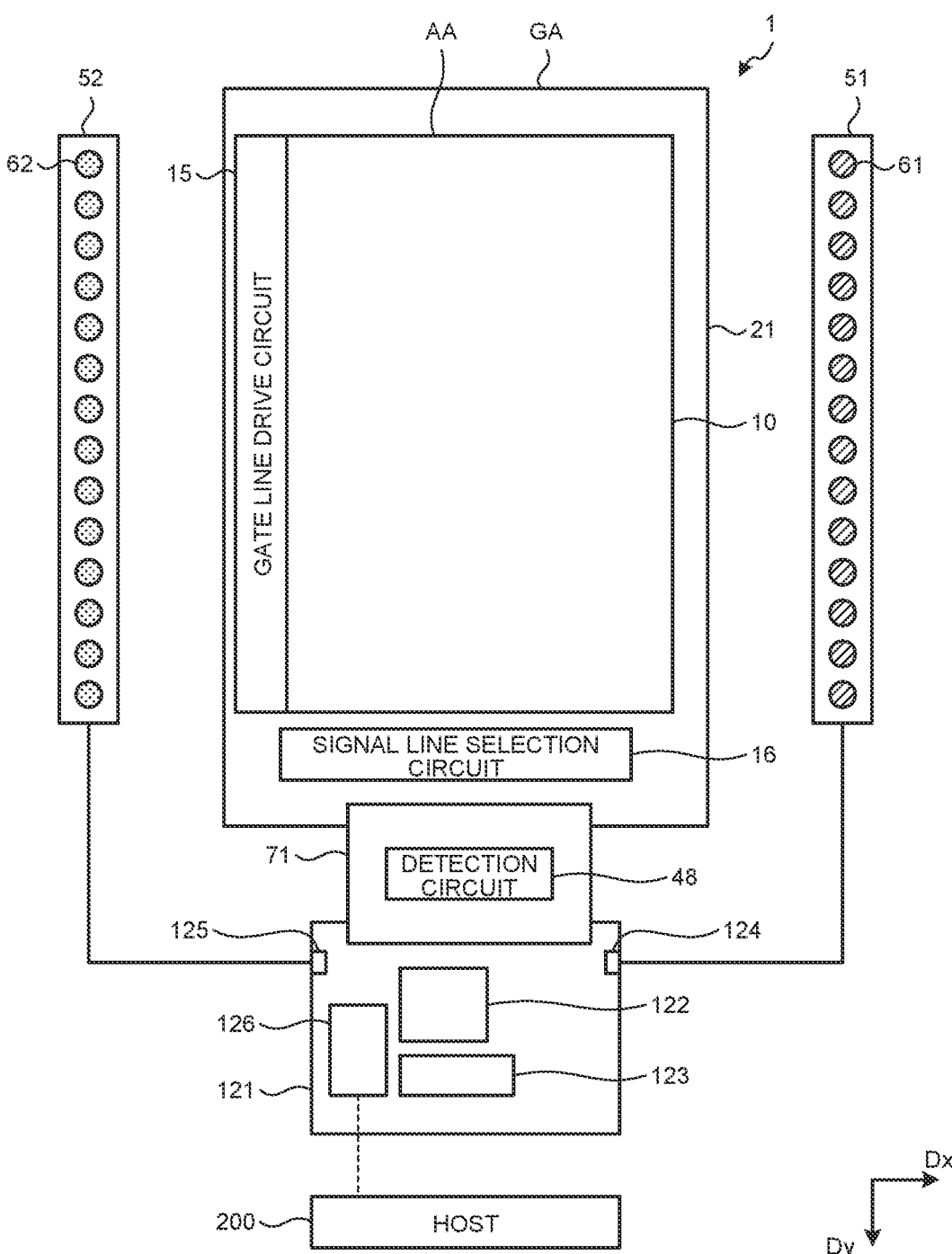
FIG. 1 is a plan view illustrating a detection device according to an embodiment.

The following describes mode (embodiment) for carrying out the present disclosure in detail with reference to the drawings. The present disclosure is not limited to the description of the embodiment given below. Components described below include those easily conceivable by those skilled in the art or those substantially identical thereto. In addition, the components described below can be combined as appropriate. What is disclosed herein is merely an example, and the present disclosure naturally encompasses appropriate modifications easily conceivable by those skilled in the art while maintaining the gist of the disclosure. To further clarify the description, the drawings may schematically illustrate, for example, widths, thicknesses, and shapes of various parts as compared with actual aspects thereof. However, they are merely examples, and interpretation of the present disclosure is not limited thereto. The same component as that described with reference to an already mentioned drawing is denoted by the same reference numeral through the description and the drawings, and detailed description thereof may not be repeated where appropriate.

In this disclosure, when an element is described as being "on" another element, the element can be directly on the other element, or there can be one or more elements between the element and the other element.

FIG. 1 is a plan view illustrating a detection device according to the embodiment. As illustrated in FIG. 1, a detection device 1 includes a sensor base member 21, a sensor 10, a gate line drive circuit 15, a signal line selection circuit 16, a detection circuit 48, a control circuit 122, a power supply circuit 123, first light sources 61, and second light sources 62. FIG. 1 illustrates an example in which a first light source base member 51 is provided with the first light sources 61 and a second light source base member 52 is provided with the second light sources 62. However, the arrangement of the first and the second light sources 61 and 62 illustrated in FIG. 1 is merely an example, and can be changed as appropriate. For example, the first and the second light sources 61 and 62 may be arranged on each of the first and the second light source base members 51 and 52. In this case, a group including the first light sources 61 and a group including the second light sources 62 may be arranged in a second direction Dy, or the first and the second light sources 61 and 62 may be alternately arranged in the second direction Dy. The first and the second light sources 61 and 62 may be provided on one light source base member, or three or more light source base members. A specific example of the arrangement of the first and the second light sources 61 and 62 will be described later.

The detection device 1 is electrically coupled to a host 200. The host 200 is, for example, a higher-level control device for an apparatus (not illustrated) to which the detection device 1 is applied. The host 200 performs a predetermined biometric information acquisition process based on data output from the detection device 1.

The sensor base member 21 is electrically coupled to a control substrate 121 through a flexible printed circuit board 71. The flexible printed circuit board 71 is provided with the detection circuit 48. The control substrate 121 is provided with the control circuit 122, the power supply circuit 123, and an output circuit 126.

The control circuit 122 includes, for example, a control integrated circuit (IC) that outputs logic control signals. The control circuit 122 may be, for example, a programmable logic device (PLD) such as a field-programmable gate array (FPGA).

The control circuit 122 supplies control signals to the sensor 10, the gate line drive circuit 15, and the signal line selection circuit 16 to control a detection operation of the sensor 10. The control circuit 122 supplies control signals to the first and the second light sources 61 and 62 to control lighting and non-lighting of the first and the second light sources 61 and 62.

The power supply circuit 123 supplies voltage signals including, for example, a sensor power supply potential VDDSNS (refer to FIG. 4) to the sensor 10, the gate line drive circuit 15, and the signal line selection circuit 16. The power supply circuit 123 supplies a power supply voltage to the first and the second light sources 61 and 62.

The output circuit 126 is, for example, a Universal Serial Bus (USB) controller IC and controls communication between the control circuit 122 and the host 200.

The sensor base member 21 has a detection area AA and a peripheral area GA. The detection area AA is an area provided with a plurality of optical sensors PD (refer to FIG. 4) included in the sensor 10. The peripheral area GA is an area between the outer perimeter of the detection area AA and the ends of the sensor base member 21, and is an area not provided with the optical sensors PD.

The gate line drive circuit 15 and the signal line selection circuit 16 are provided in the peripheral area GA. Specifically, the gate line drive circuit 15 is provided in an area extending along the second direction Dy in the peripheral area GA. The signal line selection circuit 16 is provided in an area extending along a first direction Dx in the peripheral area GA, and is provided between the sensor 10 and the detection circuit 48.

The first direction Dx is one direction in a plane parallel to the sensor base member 21. The second direction Dy is one direction in the plane parallel to the sensor base member 21, and is a direction orthogonal to the first direction Dx. The second direction Dy may non-orthogonally intersect the first direction Dx. A third direction Dz is a direction orthogonal to the first direction Dx and the second direction Dy, and is a direction normal to the sensor base member 21.

The first light sources 61 are provided on the first light source base member 51, and are arranged along the second direction Dy. The second light sources 62 are provided on the second light source base member 52, and are arranged along the second direction Dy. The first light source base member 51 and the second light source base member 52 are electrically coupled, through terminals 124 and 125 provided on the control substrate 121, to the control circuit 122 and the power supply circuit 123.

For example, inorganic light-emitting diodes (LEDs) or organic electroluminescent (EL) diodes (organic light-emitting diodes (OLEDs)) are used as the first and the second light sources 61 and 62. The first and the second light sources 61 and 62 emit first light and second light, respectively, having different wavelengths.

The first light emitted from the first light sources 61 is reflected, for example, on a surface of an object to be detected, such as a finger or a wrist of a subject, and is incident on the sensor 10. As a result, the sensor 10 can detect a fingerprint by detecting a shape of asperities on the surface of a finger Fg or the like. The second light emitted from the second light sources 62 is, for example, reflected in the finger Fg or the like, or transmitted through the finger Fg or the like, and is incident on the sensor 10. As a result, the sensor 10 can detect information on a living body in the finger, the wrist, and the like of the subject. Examples of the information on the living body include pulse waves, pulsation, and a vascular image of the subject. That is, the detection device 1 may be configured as a fingerprint detection device to detect a fingerprint or a vein detection device to detect a vascular pattern of, for example, veins.

The first light may have a wavelength of from 520 nm to 600 nm, for example, a wavelength of approximately 550 nm, and the second light may have a wavelength of from 780 nm to 950 nm, for example, a wavelength of approximately 850 nm. In this case, the first light is visible light in blue or green (blue light or green light), and the second light is infrared light. The sensor 10 can detect a fingerprint based on the first light emitted from the first light sources 61. The second light emitted from the second light sources 62 is reflected in, or transmitted through or absorbed by the object to be detected, and is incident on the sensor 10. As a result, the sensor 10 can detect the biometric data such as the pulse waves and the vascular image (vascular pattern) as the information on the living body in the finger, the wrist, and the like of the subject.

Alternatively, the first light may have a wavelength of from 600 nm to 700 nm, for example, approximately 660 nm, and the second light may have a wavelength of from 780 nm to 950 nm, for example, approximately 850 nm. In this case, the sensor 10 can detect a blood oxygen level in addition to the pulse waves, the pulsation, and the vascular image as the information on the living body based on the first light emitted from the first light sources 61 and the second light emitted from the second light sources 62. As described above, the detection device 1 includes the first and the second light sources 61 and 62, and performs the detection based on the first light and the detection based on the second light, and thereby can detect the various types of information on the living body.

Figure 2:
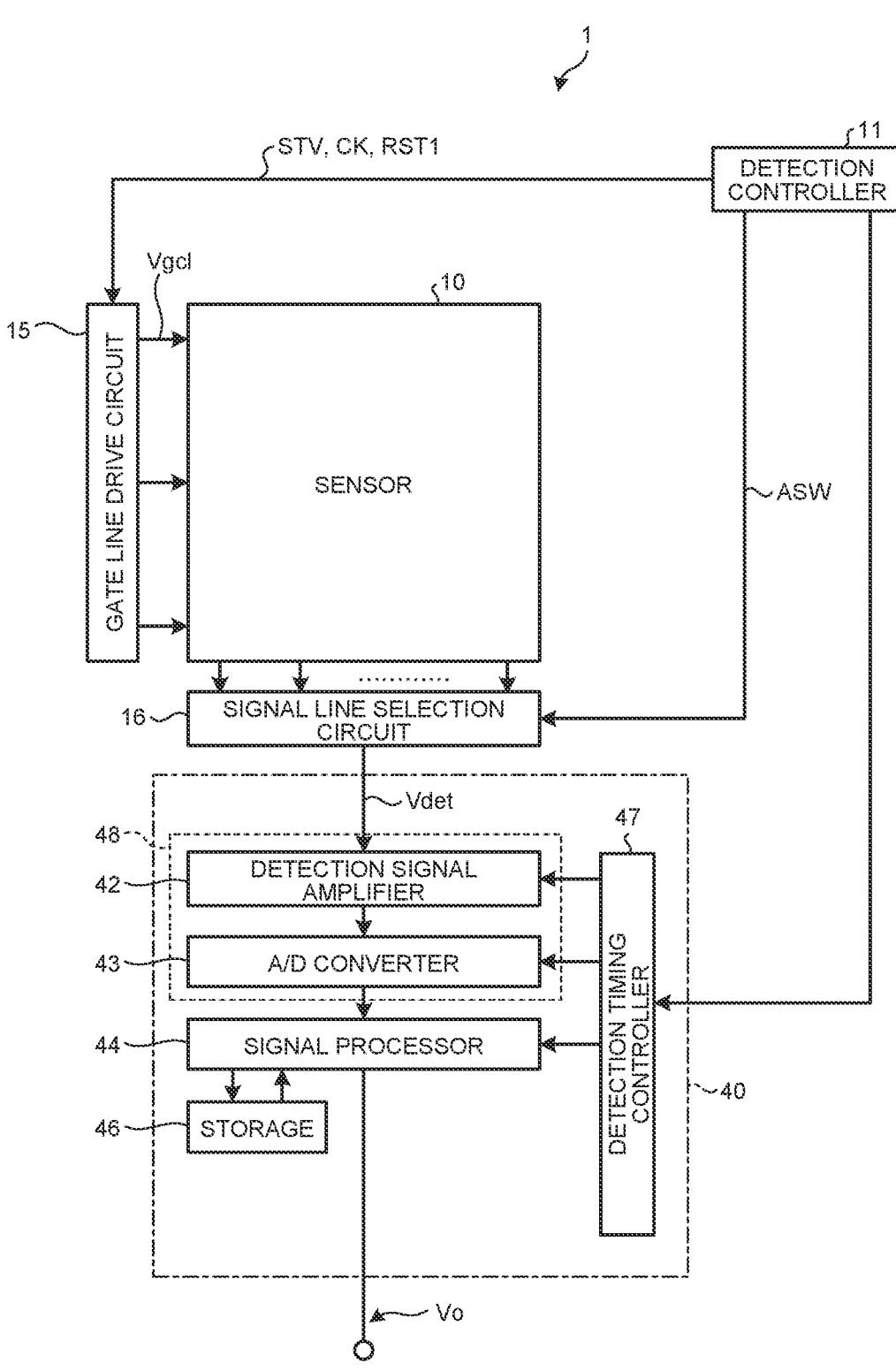
FIG. 2 is a block diagram illustrating a configuration example of the detection device according to the embodiment.

FIG. 2 is a block diagram illustrating a configuration example of the detection device according to the embodiment. As illustrated in FIG. 2, the detection device 1 further includes a detection controller (detection control circuit) 11 and a detector (detection signal processing circuit) 40.

The sensor 10 includes the optical sensors PD. Each of the optical sensors PD included in the sensor 10 is an organic photodiode (OPD), and outputs an electrical signal corresponding to light emitted thereto as a detection signal Vdet to the signal line selection circuit 16. The sensor 10 performs the detection in response to a gate drive signal Vgcl supplied from the gate line drive circuit 15.

The detection controller 11 is a circuit that supplies respective control signals to the gate line drive circuit 15, the signal line selection circuit 16, and the detector 40 to control operations of these components. The detection controller 11 supplies various control signals including, for example, a start signal STV, a clock signal CK, and a reset signal RST1 to the gate line drive circuit 15. The detection controller 11 also supplies various control signals including, for example, a selection signal ASW to the signal line selection circuit 16. The detection controller 11 supplies various control signals to the first and the second light sources 61 and 62 to control the lighting and the non-lighting of each group of the first and the second light sources 61 and 62.

The gate line drive circuit 15 is a circuit that drives a plurality of gate lines GCL (refer to FIG. 3) based on the various control signals. The gate line drive circuit 15 sequentially or simultaneously selects the gate lines GCL and supplies the gate drive signals Vgcl to the selected gate lines GCL. Through this operation, the gate line drive circuit 15 selects the optical sensors PD coupled to the gate lines GCL.

Figure 3:
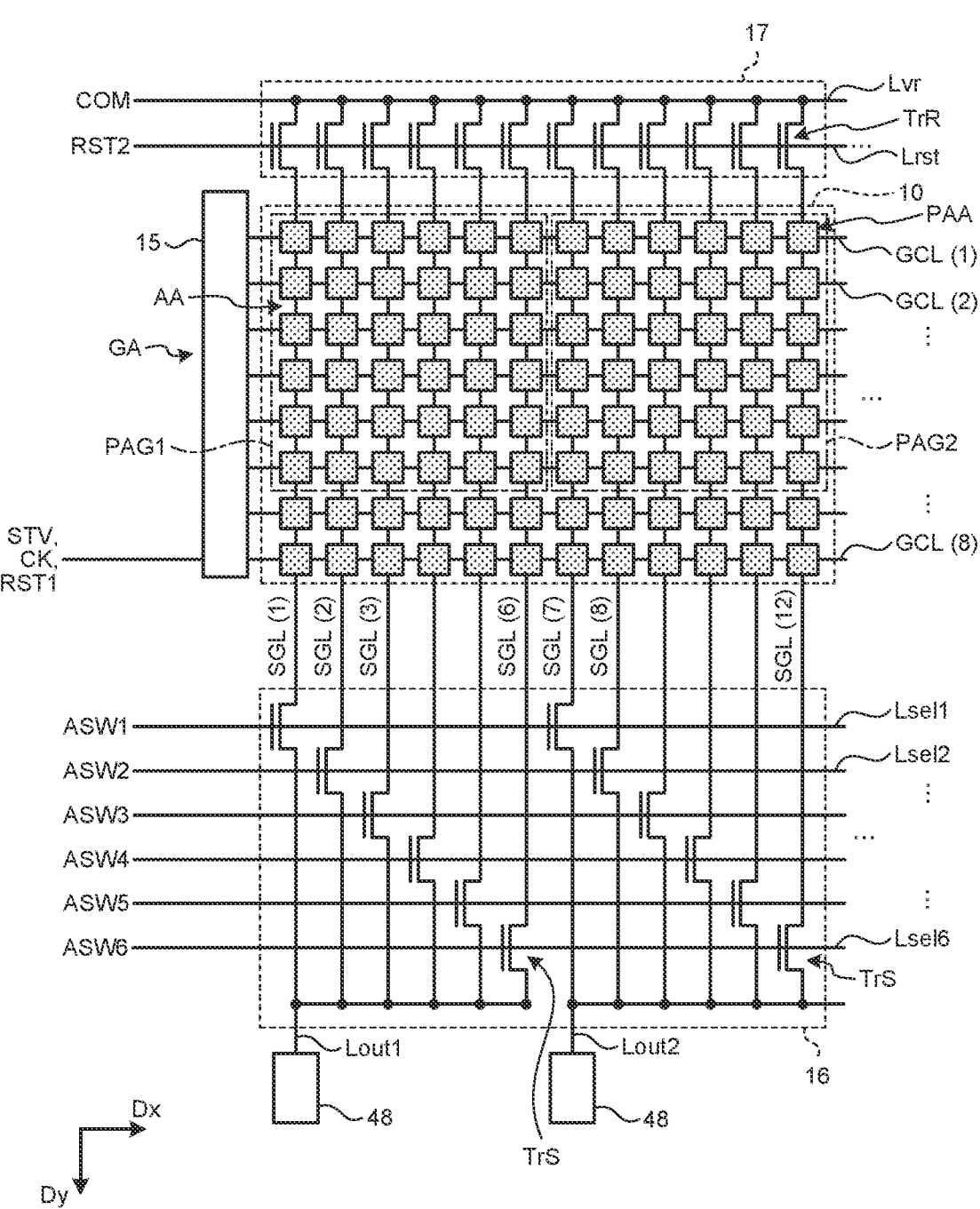
FIG. 3 is a circuit diagram illustrating the detection device.

The signal line selection circuit 16 is a switch circuit that sequentially or simultaneously selects a plurality of signal lines SGL (refer to FIG. 3). The signal line selection circuit 16 is, for example, a multiplexer. The signal line selection circuit 16 electrically couples the selected signal lines SGL to the detection circuit 48 based on the selection signal ASW supplied from the detection controller 11. By this operation, the signal line selection circuit 16 outputs the detection signals Vdet of the optical sensors PD to the detector 40.

The detector 40 includes the detection circuit 48, a signal processor (signal processing circuit) 44, a storage (storage circuit) 46, and a detection timing controller (detection timing control circuit) 47. Based on a control signal supplied from the detection controller 11, the detection timing controller 47 controls the detection circuit 48 and the signal processor 44 so as to operate in synchronization with each other.

The detection circuit 48 generates a detection value of each of the optical sensors PD based on the detection signal of the optical sensor PD output from the sensor 10. The detection circuit 48 is, for example, an analog front-end (AFE) circuit.

The detection circuit 48 is a signal processing circuit having functions of at least a detection signal amplifier 42 and an analog-to-digital (A/D) converter 43. The detection signal amplifier 42 amplifies the detection signals Vdet. The A/D converter 43 converts analog signals output from the detection signal amplifier 42 into digital signals.

In the present disclosure, the control circuit 122 includes the signal processor 44 and the storage 46.

The signal processor 44 acquires the biometric data for generating the information on the living body based on the detection values of the optical sensors PD output from the detection circuit 48. In the present disclosure, the information on the living body includes the pulse waves acquired using the infrared light and/or the red light.

The storage 46 temporarily stores therein signals processed by the signal processor 44. In the present disclosure, the storage 46 also stores therein information on a biometric data acquisition area that is set in a biometric data acquisition area setting process (to be described later) when the signal processor 44 acquires the biometric data, and stores therein various types of setting information. In an aspect of the present disclosure, the storage 46 may include, for example, a random-access memory (RAM), a read-only memory (ROM), and an electrically erasable programmable read-only memory (EEPROM). The storage 46 may be a register circuit, for example.

The following describes a circuit configuration example of the detection device 1. FIG. 3 is a circuit diagram illustrating the detection device. As illustrated in FIG. 3, the sensor 10 has a plurality of partial detection areas PAA arranged in a matrix having a row-column configuration. Each of the partial detection areas PAA is provided with the optical sensor PD.

The gate lines GCL extend in the first direction Dx, and are each coupled to the partial detection areas PAA arranged in the first direction Dx. A plurality of gate lines GCL(1), GCL(2), ..., GCL(8) are arranged in the second direction Dy and are each coupled to the gate line drive circuit 15. In the following description, the gate lines GCL(1), GCL(2), ..., GCL(8) will each be simply referred to as the gate line GCL when they need not be distinguished from one another. For ease of understanding of the description, FIG. 3 illustrates eight of the gate lines GCL. However, this is merely an example, and M gate lines GCL (where M is a natural number, for example, M=256) may be arranged.

The signal lines SGL extend in the second direction Dy and are each coupled to the optical sensors PD of the partial detection areas PAA arranged in the second direction Dy. A plurality of signal lines SGL(1), SGL(2), ..., SGL(12) are arranged in the first direction Dx, and are each coupled to the signal line selection circuit 16 and a reset circuit 17. In the following description, the signal lines SGL(1), SGL(2), ..., SGL(12) will each be simply referred to as the signal line SGL when they need not be distinguished from one another.

For ease of understanding of the description, 12 of the signal lines SGL are illustrated. However, this is merely an example, and N signal lines SGL (where N is a natural number, for example, N=252) may be arranged. In FIG. 3, the sensor 10 is provided between the signal line selection circuit 16 and the reset circuit 17. The present disclosure is not limited thereto. The signal line selection circuit 16 and the reset circuit 17 may be coupled to ends of the signal lines SGL in the same direction.

The gate line drive circuit 15 receives the various control signals such as the start signal STV, the clock signal CK, and the reset signal RST1 from the control circuit 122 (refer to FIG. 1). The gate line drive circuit 15 sequentially selects the gate lines GCL(1), GCL(2), ..., GCL(8) in a time-division manner based on the various control signals. The gate line drive circuit 15 supplies the gate drive signal Vgcl to the selected one of the gate lines GCL. This operation supplies the gate drive signal Vgcl to a plurality of first switching elements Tr coupled to the gate line GCL, and corresponding ones of the partial detection areas PAA arranged in the first direction Dx are each selected as a detection target.

The gate line drive circuit 15 may perform different driving for each of detection modes including the detection of a fingerprint and the detection of a plurality of different items of information on the living body (including, for example, the pulse waves, the pulsation, the vascular image, and the blood oxygen level, which are hereinafter called also simply "biometric information"). For example, the gate line drive circuit 15 may drive more than one of the gate lines GCL collectively.

Specifically, the gate line drive circuit 15 simultaneously selects a predetermined number of the gate lines GCL from among the gate lines GCL(1), GCL(2), ..., GCL(8) based on the control signals. For example, the gate line drive circuit 15 simultaneously selects six of the gate lines GCL (1) to GCL(6) and supplies thereto the gate drive signals Vgcl. The gate line drive circuit 15 supplies the gate drive signals Vgcl through the selected six gate lines GCL to the first switching elements Tr. By this operation, block units PAG1 and PAG2 each including corresponding ones of the partial detection areas PAA arranged in the first direction Dx and the second direction Dy are each selected as the detection target. The gate line drive circuit 15 drives the predetermined number of the gate lines GCL collectively, and sequentially supplies the gate drive signals Vgcl in units of the predetermined number of the gate lines GCL.

The signal line selection circuit 16 includes a plurality of selection signal lines Lsel, a plurality of output signal lines Lout, and third switching elements TrS. The third switching elements TrS are provided correspondingly to the signal lines SGL. Six signal lines SGL(1), SGL(2), ..., SGL(6) are coupled to a common output signal line Lout1. Six signal lines SGL(7), SGL(8), ..., SGL(12) are coupled to a common output signal line Lout2. The output signal lines Lout1 and Lout2 are each coupled to the detection circuit 48.

The signal lines SGL(1), SGL(2), ..., SGL(6) are grouped into a first signal line block, and the signal lines SGL(7), SGL(8), ..., SGL(12) are grouped into a second signal line block. The selection signal lines Lsel are coupled to the gates of the respective third switching elements TrS included in one of the signal line blocks. One of the selection signal lines Lsel is coupled to the gates of the third switching elements TrS in the signal line blocks.

Specifically, selection signal lines Lsel1, Lsel2, ..., Lsel6 are coupled to the third switching elements TrS corresponding to the signal lines SGL(1), SGL(2), ..., SGL(6), respectively. The selection signal line Lsel1 is coupled to the third switching element TrS corresponding to the signal line SGL(1) and the third switching element TrS corresponding to the signal line SGL(7). The selection signal line Lsel2 is coupled to the third switching element TrS corresponding to the signal line SGL(2) and the third switching element TrS corresponding to the signal line SGL(8).

The control circuit 122 (refer to FIG. 1) sequentially supplies the selection signal ASW to the selection signal lines Lsel. This operation causes the signal line selection circuit 16 to operate the third switching elements TrS to sequentially select the signal lines SGL in one of the signal line blocks in a time-division manner. The signal line selection circuit 16 selects one of the signal lines SGL in each of the signal line blocks. With the above-described configuration, the detection device 1 can reduce the number of integrated circuits (ICs) including the detection circuit 48 or the number of terminals of the ICs.

The signal line selection circuit 16 may couple more than one of the signal lines SGL collectively to the detection circuit 48. Specifically, the control circuit 122 (refer to FIG. 1) simultaneously supplies the selection signal ASW to the selection signal lines Lsel. The signal line selection circuit 16 operates the third switching elements TrS to select the signal lines SGL (for example, six of the signal lines SGL) in one of the signal line blocks and couples the signal lines SGL to the detection circuit 48. As a result, signals detected in each of the block units PAG1 and PAG2 are output to the detection circuit 48. In this case, the signals from the partial detection areas PAA (optical sensors PD) included in each of the block units PAG1 and PAG2 are integrated and output to the detection circuit 48.

The detection is performed for each of the block units PAG1 and PAG2 by the operations of the gate line drive circuit 15 and the signal line selection circuit 16. As a result, the strength of the detection signal Vdet obtained by a one-time detection operation increases, so that the sensor sensitivity can be improved.

In the detection device 1 of the present disclosure, the number of the partial detection areas PAA (optical sensors PD) included in each of the block units PAG1 and PAG2 can be changed. Thus, the resolution per inch (pixels per inch (ppi), hereinafter, referred to as "definition") can be set according to the information to be acquired.

For example, the number of the partial detection areas PAA (optical sensors PD) included in each of the block units PAG1 and PAG2 can be relatively reduced. While this setting results in a longer detection time and a lower frame rate (for example, 20 frames per second (fps) or lower), the detection can be performed at a higher definition (for example, at 300 ppi or higher). Hereafter, the term "first mode" denotes a mode of performing the detection at a lower frame rate and a higher definition. By selecting the first mode of performing the detection at a lower frame rate and a higher definition, for example, a fingerprint on the surface of a finger can be acquired at a higher definition.

Alternatively, for example, the number of the partial detection areas PAA (optical sensors PD) included in each of the block units PAG1 and PAG2 can be relatively increased. While this setting results in a lower definition (for example, 50 ppi or lower), the detection can be performed at a higher frame rate (for example, at 100 fps or higher) that allows the detection to be repeatedly performed in a shorter time in one frame. Hereafter, the term "second mode" denotes a mode of performing the detection at a higher frame rate and a lower definition. By selecting the second mode of performing the detection at a higher frame rate and a lower definition, for example, time-dependent changes in the pulse waves can be more accurately detected. In the second mode, calculation of a pulse wave velocity and calculation of blood pressure and the like are enabled by using the pulse waves acquired at a higher frame rate (for example, 1000 fps or higher).

For example, when acquiring the vascular image (vein pattern), the number of the partial detection areas PAA (optical sensors PD) included in each of the block units PAG1 and PAG2 is set to an intermediate value between those of the first mode and the second mode. This setting allows the detection to be performed at a medium frame rate higher than that of the first mode and lower than that of the second mode (for example, higher than 20 fps and lower than 100 fps) and at a medium definition lower than that of the first mode and higher than that of the second mode (for example, higher than 50 ppi and lower than 300 ppi). Hereafter, the term "third mode" denotes a mode of performing the detection at a medium frame rate and a medium definition. The third mode of performing the detection at a medium frame rate and a medium definition is suitable for, for example, acquiring the vascular pattern of veins and the like.

As illustrated in FIG. 3, the reset circuit 17 includes a reference signal line Lvr, a reset signal line Lrst, and fourth switching elements TrR. The fourth switching elements TrR are provided correspondingly to the signal lines SGL. The reference signal line Lvr is coupled to either the sources or the drains of the fourth switching elements TrR. The reset signal line Lrst is coupled to the gates of the fourth switching elements TrR.

The control circuit 122 supplies a reset signal RST2 to the reset signal line Lrst. This operation turns on the fourth switching elements TrR to electrically couple the signal lines SGL to the reference signal line Lvr. The power supply circuit 123 supplies a reference signal COM to the reference signal line Lvr. This operation supplies the reference signal COM to a capacitive element Ca (refer to FIG. 4) included in each of the partial detection areas PAA.

Figure 4:
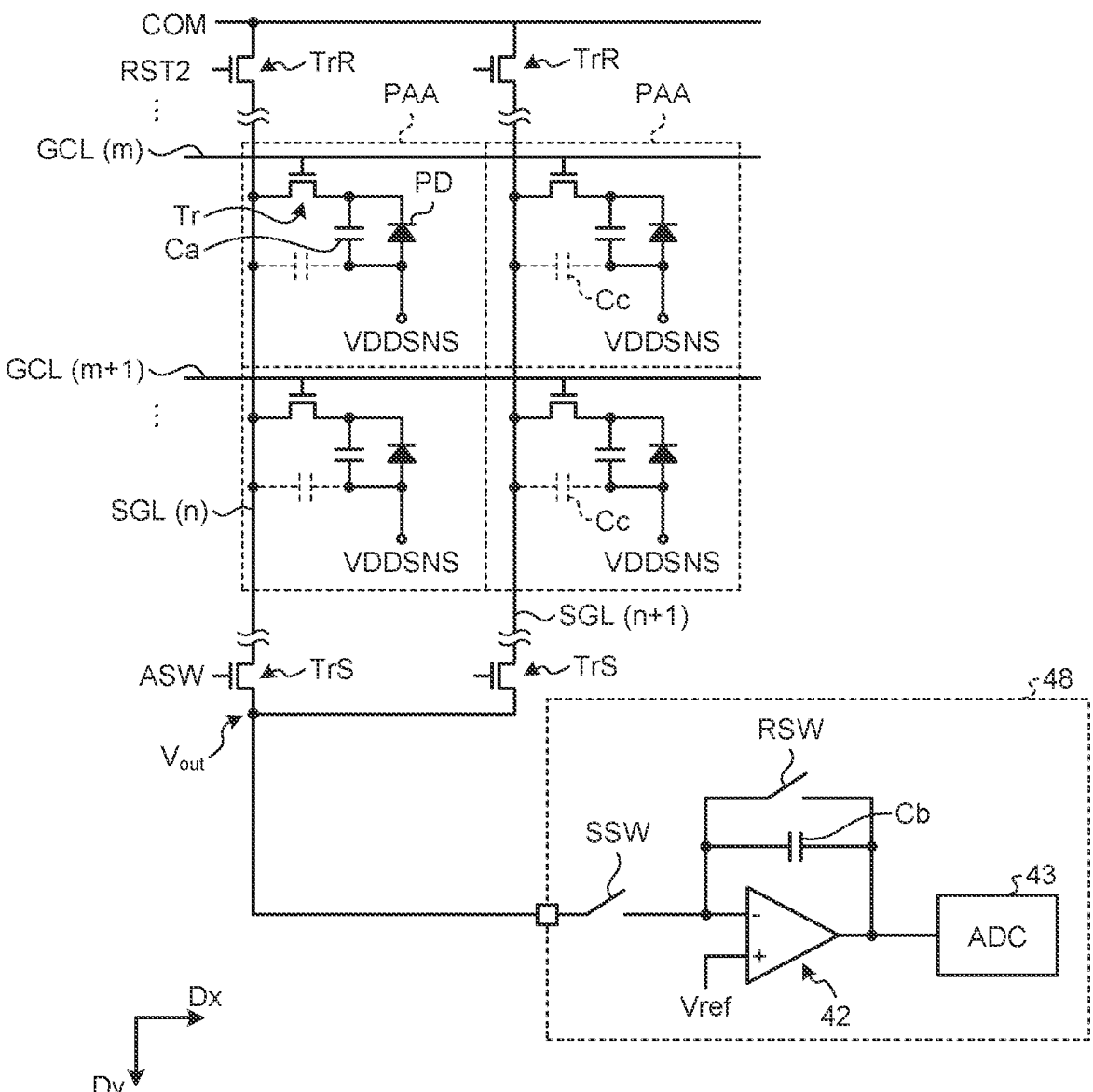
FIG. 4 is a circuit diagram illustrating a plurality of partial detection areas of the detection device according to the embodiment.

FIG. 4 is a circuit diagram illustrating the partial detection areas of the detection device according to the embodiment. FIG. 4 also illustrates a circuit configuration of the detection circuit 48. As illustrated in FIG. 4, each of the partial detection areas PAA includes the optical sensor PD, the capacitive element Ca, and a first switching element Tr. The capacitive element Ca is a capacitor (sensor capacitance) generated in the optical sensor PD, and is equivalently coupled in parallel with the optical sensor PD. In addition, signal line capacitance Cc is a parasitic capacitor (parasitic capacitance) generated on the signal line SGL, and is equivalently provided between the signal line SGL and a node between the anode of the optical sensor PD and one end side of the capacitive element Ca.

FIG. 4 illustrates two gate lines GCL(m) and GCL(m+1) arranged in the second direction Dy among the gate lines GCL. FIG. 4 also illustrates two signal lines SGL(n) and SGL(n+1) arranged in the first direction Dx among the signal lines SGL. The partial detection area PAA is an area surrounded by the gate lines GCL and the signal lines SGL.

Each of the first switching elements Tr is provided correspondingly to the optical sensor PD. The first switching element Tr is made with a thin-film transistor, and in this example, made with an n-channel metal oxide semiconductor (MOS) thin-film transistor (TFT).

The gates of the first switching elements Tr belonging to the partial detection areas PAA arranged in the first direction Dx are coupled to the gate line GCL. The sources of the first switching elements Tr belonging to the partial detection areas PAA arranged in the second direction Dy are coupled to the signal line SGL. The drain of the first switching element Tr is coupled to the cathode of the optical sensor PD and the capacitive element Ca.

The anode of the optical sensor PD is supplied with the sensor power supply potential VDDSNS from the power supply circuit 123. The signal line SGL and the capacitive element Ca are supplied with the reference signal COM that serves as an initial potential of the signal line SGL and the capacitive element Ca from the power supply circuit 123.

When the partial detection area PAA is irradiated with light, a current corresponding to a light quantity flows through the optical sensor PD. As a result, an electric charge is stored in the capacitive element Ca. After the first switching element Tr is turned on, a current corresponding to the electric charge stored in the capacitive element Ca flows through the signal line SGL. The signal line SGL is coupled to the detection circuit 48 through a corresponding one of the third switching elements TrS of the signal line selection circuit 16. Thus, the detection device 1 can detect a signal corresponding to the light quantity of light received by the optical sensor PD in each of the partial detection areas PAA or in each of the block units PAG1 and PAG2. Initialization of the light quantities of the first and the second light sources 61 and 62 will be described later.

During a read period Pdet (refer to FIG. 6), a switch SSW of the detection circuit 48 is turned on, and the detection circuit 48 is coupled to the signal lines SGL. The detection signal amplifier 42 of the detection circuit 48 converts a current supplied from the signal lines SGL into a voltage corresponding to the value of the current and amplifies the result. A reference potential (Vref) having a fixed potential is supplied to a non-inverting input terminal (+) of the detection signal amplifier 42, and the signal lines SGL are coupled to an inverting input terminal (−) of the detection signal amplifier 42. In the embodiment, the same signal as the reference signal COM is supplied as the reference potential (Vref) voltage. The detection signal amplifier 42 includes a capacitive element Cb and a reset switch RSW. During a reset period Prst (refer to FIG. 6), the reset switch RSW is turned on, and the electric charge of the capacitive element Cb is reset.

Figure 5A:
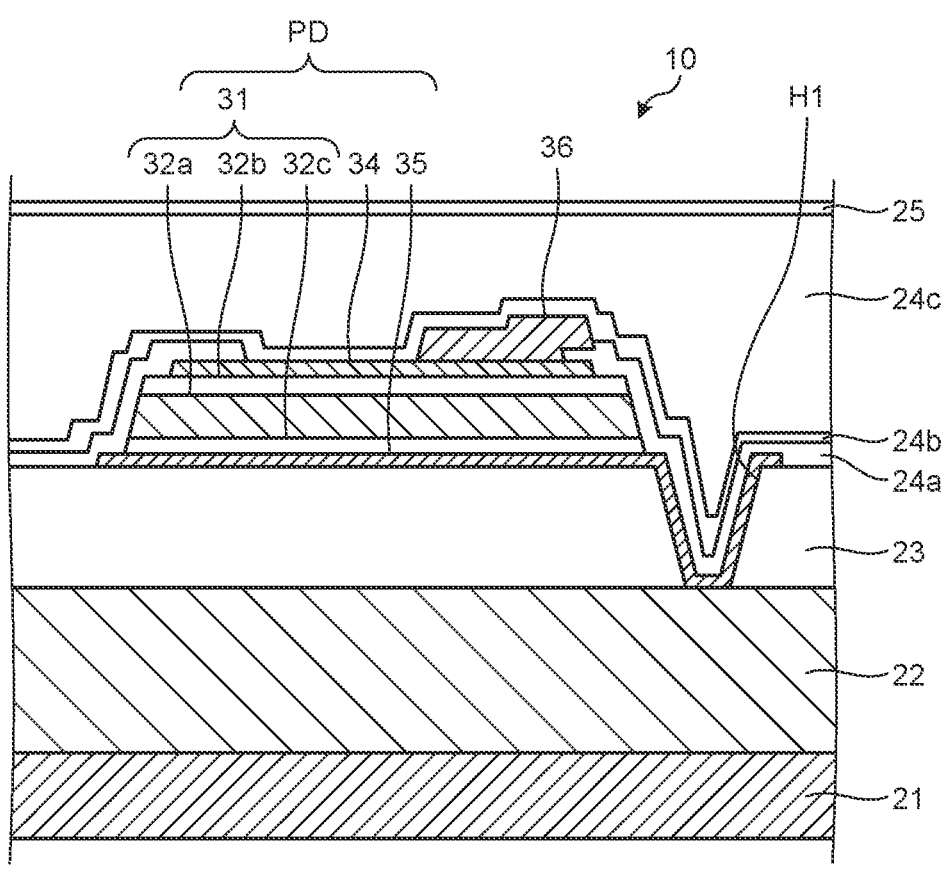
FIG. 5A is a sectional view illustrating a schematic sectional configuration of a sensor.

The following describes a configuration of the optical sensor PD. FIG. 5A is a sectional view illustrating a schematic sectional configuration of the sensor. As illustrated in FIG. 5A, the sensor 10 includes the sensor base member 21, a TFT layer 22, an insulating layer 23, the optical sensor PD, and insulating layers 24*a*, 24*b*, 24*c*, and 25. The sensor base member 21 is an insulating base member, and is made using, for example, glass or a resin material. The sensor base member 21 is not limited to having a flat plate shape, and may have a curved surface. In this case, the sensor base member 21 can be a film-like resin. The sensor base member 21 has a first surface and a second surface on the opposite side of the first surface. The TFT layer 22, the insulating layer 23, the optical sensor PD, and the insulating layers 24 and 25 are stacked in this order on the first surface.

The TFT layer 22 is provided with circuits such as the gate line drive circuit 15 and the signal line selection circuit 16 described above. The TFT layer 22 is also provided with TFTs, such as the first switching elements Tr, and various types of wiring, such as the gate lines GCL and the signal lines SGL. The sensor base member 21 and the TFT layer 22 serve as a drive circuit board that drives the sensor for each predetermined detection area, and are also called a backplane or an array substrate.

The insulating layer 23 is an organic insulating layer, and is provided on the TFT layer 22. The insulating layer 23 is a planarizing layer that planarizes asperities formed by the first switching elements Tr and various conductive layers formed in the TFT layer 22.

The optical sensor PD is provided on the insulating layer 23. The optical sensor PD includes a lower electrode 35, a semiconductor layer 31, and an upper electrode 34, which are stacked in this order.

The lower electrode 35 is provided above the insulating layer 23 and is electrically coupled to the first switching element Tr in the TFT layer 22 through a contact hole H1. The lower electrode 35 is the cathode of the optical sensor PD and is an electrode for reading the detection signal Vdet. A metal material such as molybdenum (Mo) or aluminum (Al) is used as the lower electrode 35. Alternatively, the lower electrode 35 may be a multilayered film formed by stacking these metal materials. The lower electrode 35 may be formed of, for example, a light-transmitting conductive material such as indium tin oxide (ITO).

The semiconductor layer 31 is formed of amorphous silicon (a-Si). The semiconductor layer 31 includes an i-type semiconductor layer 32*a*, a p-type semiconductor layer 32*b*, and an n-type semiconductor layer 32*c*. The i-type semiconductor layer 32*a*, the p-type semiconductor layer 32*b*, and the n-type semiconductor layer 32*c* constitute a specific example of a photoelectric conversion element. In FIG. 5A, the n-type semiconductor layer 32*c*, the i-type semiconductor layer 32*a*, and the p-type semiconductor layer 32*b* are stacked in this order in a direction orthogonal to a surface of the sensor base member 21. However, the semiconductor layer 31 may have a reversed configuration, that is, the p-type semiconductor layer 32*b*, the i-type semiconductor layer 32*a*, and the n-type semiconductor layer 32*c* may be stacked in this order. The semiconductor layer 31 may be a photoelectric conversion element formed of organic semiconductors.

The a-Si of the n-type semiconductor layer 32*c* is doped with impurities to form an n+ region. The a-Si of the p-type semiconductor layer 32*b* is doped with impurities to form a p+ region. The i-type semiconductor layer 32*a* is, for example, a non-doped intrinsic semiconductor and has lower conductivity than that of the p-type semiconductor layer 32*b* and the n-type semiconductor layer 32*c*.

The upper electrode 34 is the anode of the optical sensor PD, and is an electrode for supplying the sensor power supply potential VDDSNS to the photoelectric conversion layer. The upper electrode 34 is a light-transmitting conductive layer of, for example, ITO, and is provided so as to be common to all the optical sensors PD.

The insulating layers 24*a* and 24*b* are provided on the insulating layer 23. The insulating layer 24*a* covers the periphery of the upper electrode 34, and is provided with an opening in a position overlapping the upper electrode 34. Coupling wiring 36 is coupled to the upper electrode 34 at a portion of the upper electrode 34 not provided with the insulating layer 24*a*. The insulating layer 24*b* is provided on the insulating layer 24*a* so as to cover the upper electrode 34 and the coupling wiring 36. The insulating layer 24*c* serving as a planarizing layer is provided on the insulating layer 24*b*. The insulating layer 25 is provided on the insulating layer 24*c*. However, the insulating layer 25 need not be provided.

Figure 5B:
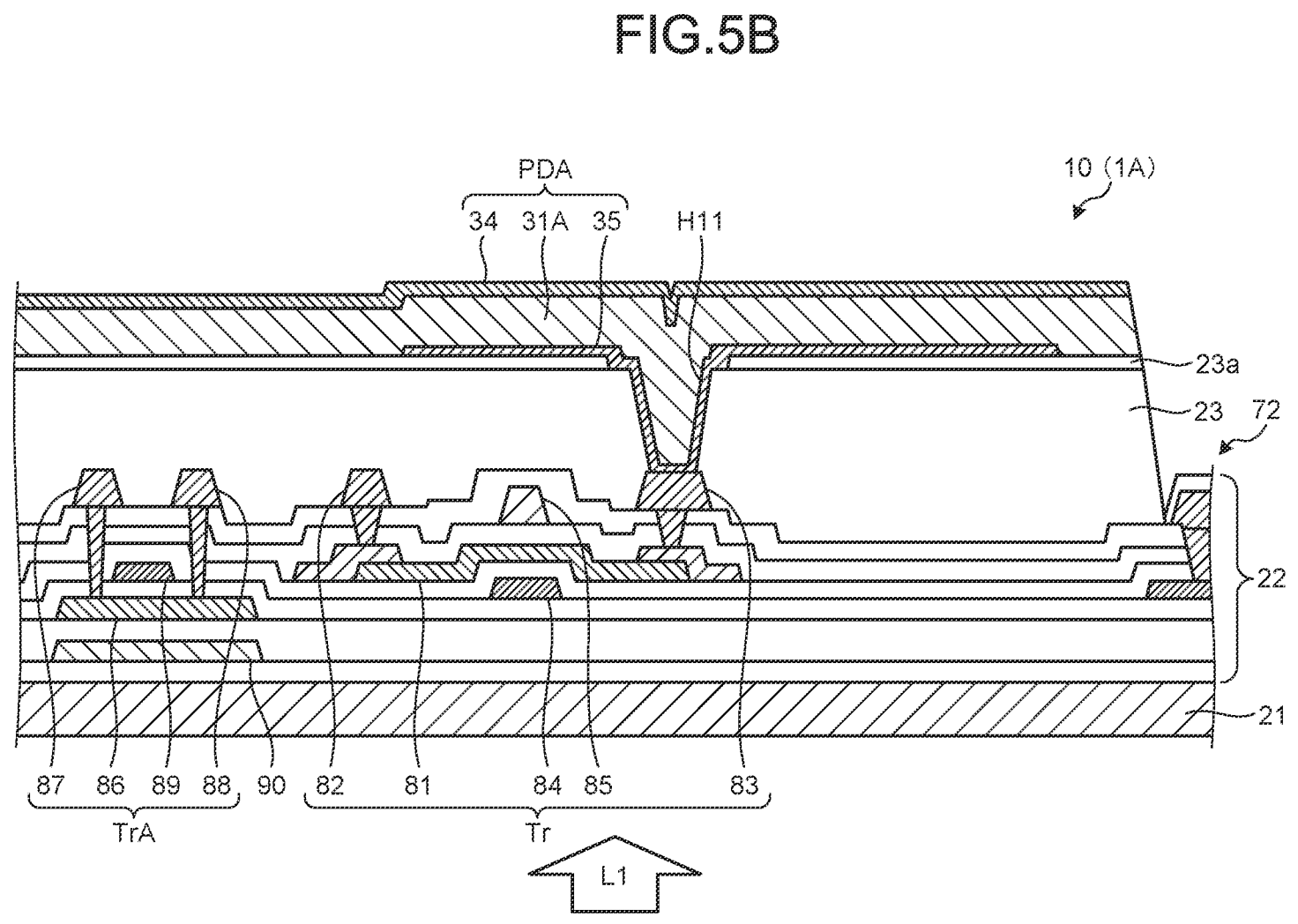

FIG. 5B is a sectional view illustrating a schematic sectional configuration of the sensor of a detection device according to a first modification. As illustrated in FIG. 5B, in a detection device 1A of the first modification, an optical sensor PDA is provided above an insulating layer 23*a*. The insulating layer 23*a* is an inorganic insulating layer provided so as to cover the insulating layer 23 and is formed of, for example, silicon nitride (SiN). The optical sensor PDA includes a photoelectric conversion layer 31A, the lower electrode 35 (cathode electrode), and the upper electrode 34 (anode electrode). The lower electrode 35, the photoelectric conversion layer 31A, and the upper electrode 34 are stacked in this order in a direction orthogonal to a first surface S1 of the sensor base member 21.

The photoelectric conversion layer 31A changes in characteristics (for example, voltage-current characteristics and resistance value) depending on light emitted thereto. An organic material is used as a material of the photoelectric conversion layer 31A. Specifically, as the photoelectric conversion layer 31A, low-molecular-weight organic materials can be used, such as fullerene ($C_{60}$), phenyl-$C_{61}$-butyric acid methyl ester (PCBM), copper phthalocyanine (CuPc), fluorinated copper phthalocyanine ($F_{16}$CuPc), 5,6,11,12-tetraphenyltetracene (rubrene), and perylene diimide (PDI) (derivative of perylene).

The photoelectric conversion layer 31A can be formed by a vapor deposition process (dry process) using any of these low-molecular-weight organic materials. In this case, the photoelectric conversion layer 31A may be, for example, a multilayered film of CuPc and $F_{16}$CuPc, or a multilayered film of rubrene and $C_{60}$. The photoelectric conversion layer 31A can also be formed by a coating process (wet process). In this case, the photoelectric conversion layer 31A is made using a material obtained by combining any of the above-listed low-molecular-weight organic materials with a high-molecular-weight organic material. As the high-molecular-weight organic material, for example, poly(3-hexylthiophene) (P3HT) and F8-alt-benzothiadiazole (F8BT) can be used. The photoelectric conversion layer 31A can be a film made of a mixture of P3HT and PCBM, or a film made of a mixture of F8BT and PDI.

The lower electrode 35 faces the upper electrode 34 with the photoelectric conversion layer 31A interposed therebetween. For example, a light-transmitting conductive material such as ITO is used as the upper electrode 34. For example, a metal material such as silver (Ag) or aluminum (Al) is used as the lower electrode 35. Alternatively, the lower electrode 35 may be made of an alloy material containing at least one or more of these metal materials.

The lower electrode 35 can be formed as a light-transmitting transflective electrode by controlling the film thickness of the lower electrode 35. For example, the lower electrode 35 is formed of a thin Ag film having a thickness of 10 nm so as to have light transmittance of approximately 60%. In this case, the optical sensor PDA can detect light emitted from both sides of the sensor base member 21, for example, both light L1 emitted from the first surface S1 side and light emitted from a second surface S2 side.

Although not illustrated in FIG. 5B, the insulating layer 24 may be provided so as to cover the upper electrode 34. The insulating layer is a passivation film and is provided to protect the optical sensor PDA.

As illustrated in FIG. 5B, the TFT layer 22 is provided with the first switching element Tr electrically coupled to the optical sensor PDA. The first switching element Tr includes a semiconductor layer 81, a source electrode 82, a drain electrode 83, and gate electrodes 84 and 85. The lower electrode 35 of the optical sensor PDA is electrically coupled to the drain electrode 83 of the first switching element Tr through a contact hole H11 provided in the insulating layers 23 and 23a.

The first switching element Tr has what is called a dual-gate structure provided with the gate electrodes 84 and 85 on the upper and lower sides of the semiconductor layer 81. However, the first switching element Tr is not limited to this structure and may have a top-gate structure or a bottom-gate structure.

FIG. 5B schematically illustrates a second switching element TrA and a terminal 72 that are provided in the peripheral area GA. The second switching element TrA is, for example, a switching element provided in the gate line drive circuit 15 (refer to FIG. 1). The second switching element TrA includes a semiconductor layer 86, a source electrode 87, a drain electrode 88, and a gate electrode 89. The second switching element TrA has what is called a top-gate structure provided with the gate electrode 89 on the upper side of the semiconductor layer 86. A light-blocking layer 90 is provided between the semiconductor layer 86 and the sensor base member 21 on the lower side of the semiconductor layer 86. The second switching element TrA is, however, not limited to this structure, and may have a bottom-gate structure or a dual-gate structure.

The semiconductor layer 81 of the first switching element Tr is provided in a layer different from that of the semiconductor layer 86 of the second switching element TrA. The semiconductor layer 81 of the first switching element Tr is formed of, for example, an oxide semiconductor. The semiconductor layer 86 of the second switching element TrA is formed of, for example, polysilicon.

Figure 6:
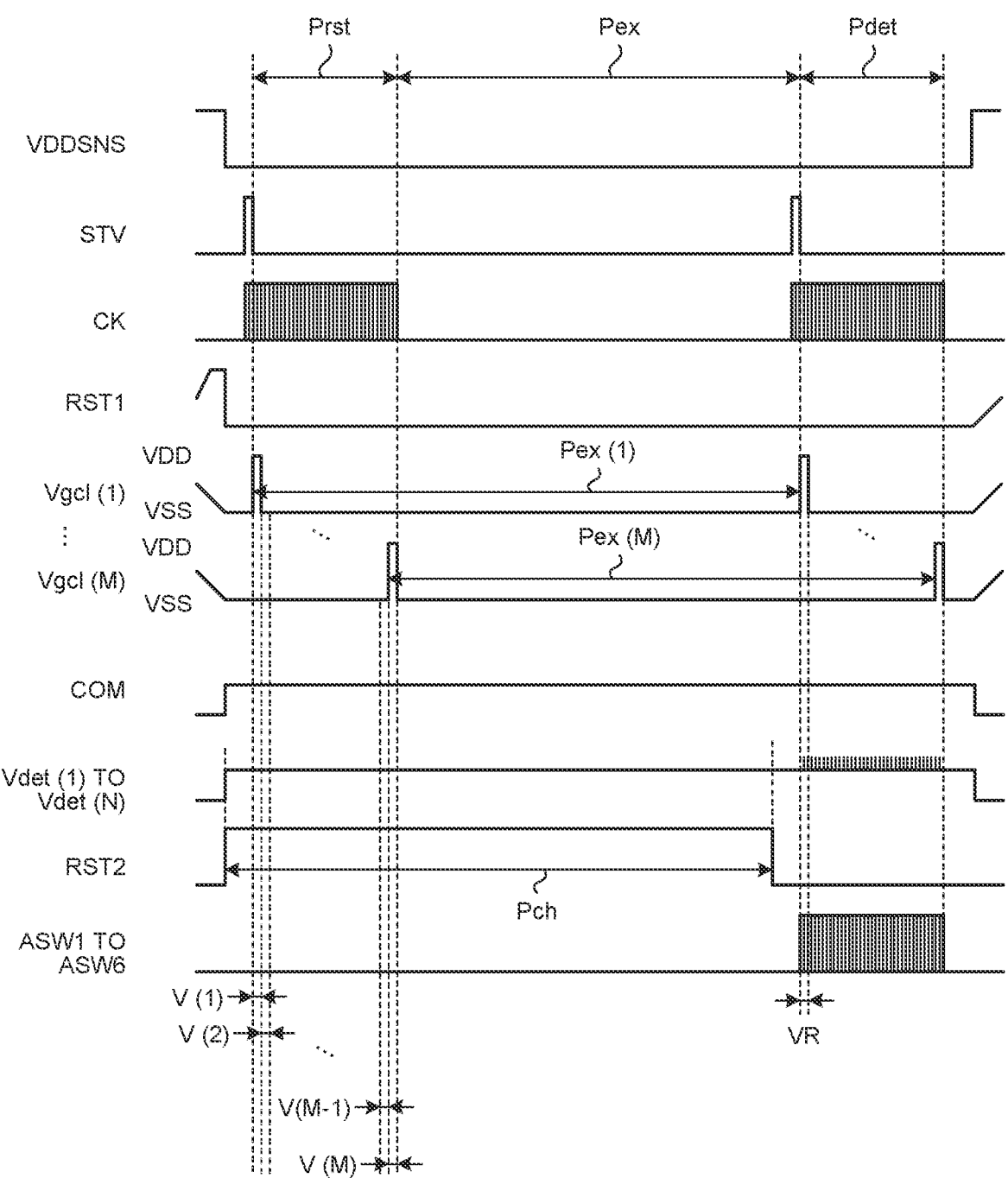
FIG. 6 is a timing waveform chart illustrating an operation example of the detection device.
Figure 7:
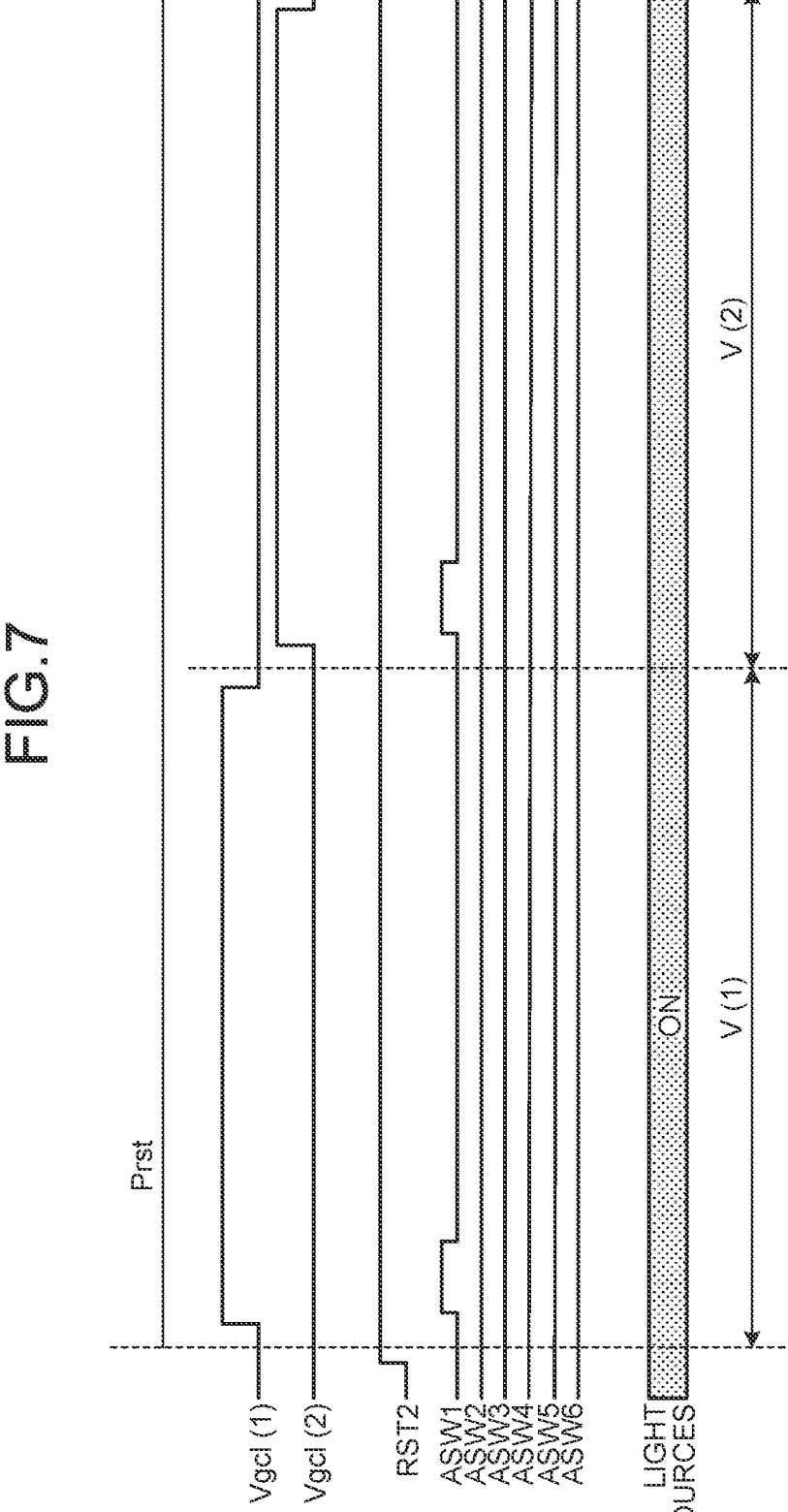
FIG. 7 is a timing waveform chart illustrating an operation example during a reset period in FIG. 6.
Figure 8:
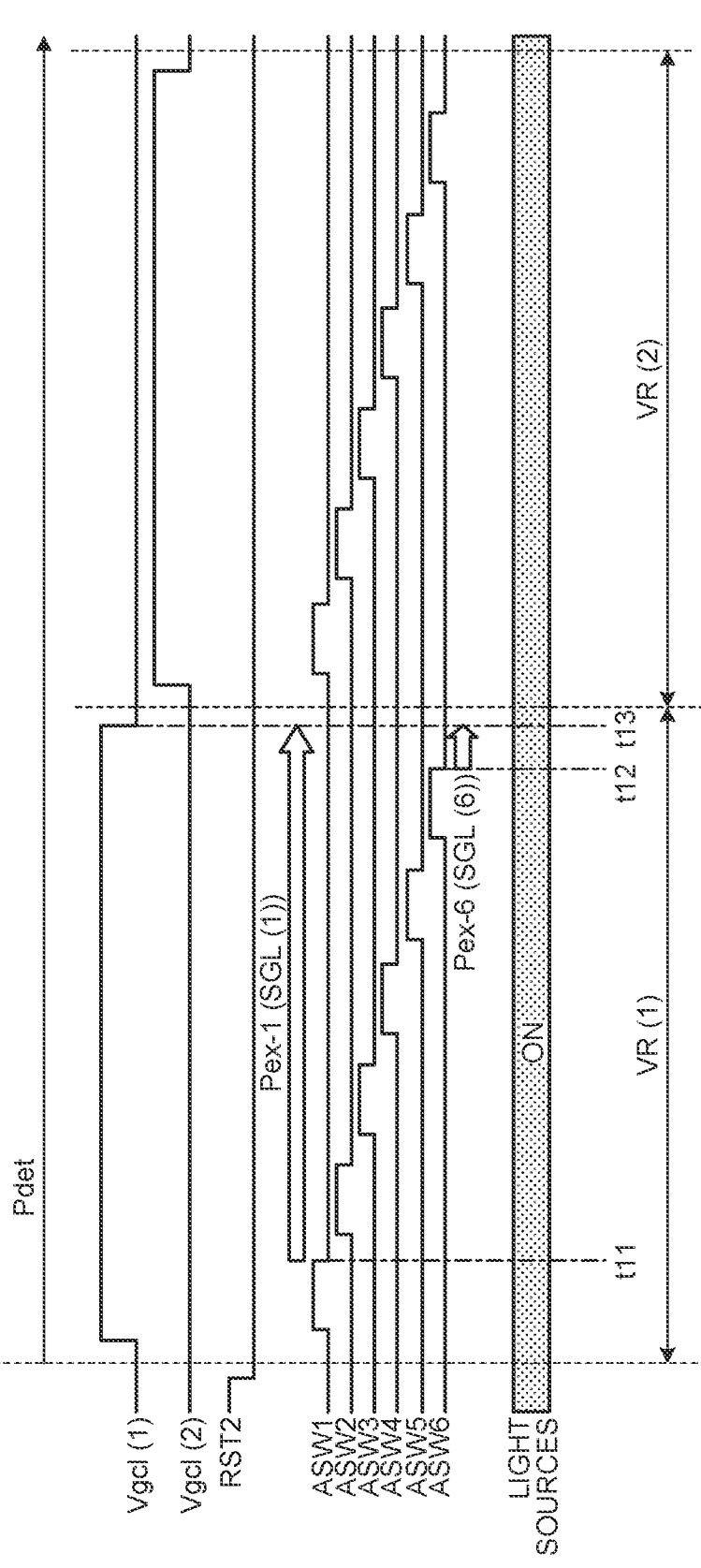
FIG. 8 is a timing waveform chart illustrating an operation example during a read period in FIG. 6.
Figure 9:
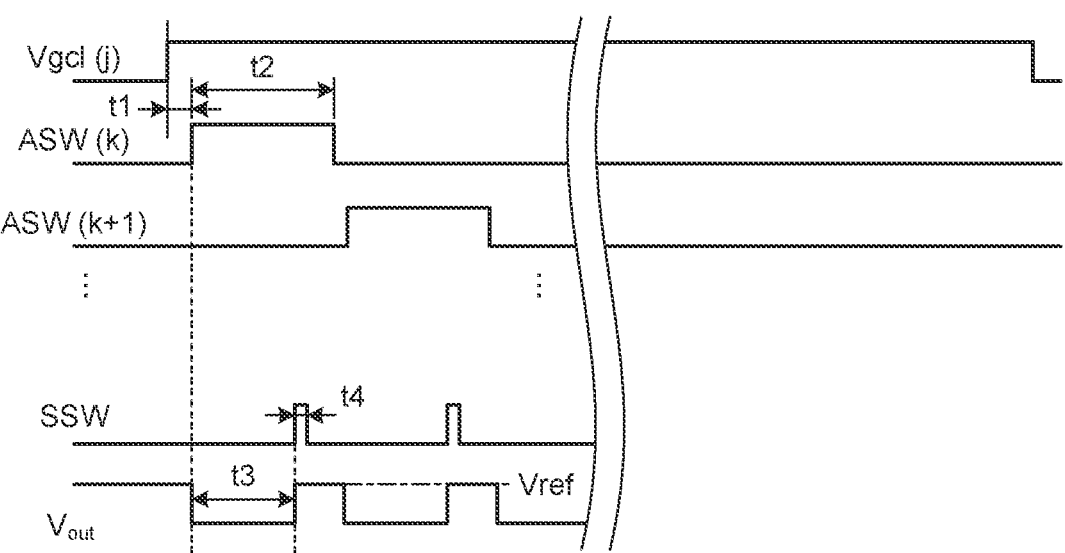
FIG. 9 is a timing waveform chart illustrating an operation example during a drive period of one gate line included in a row read period VR in FIG. 6.
Figure 10:
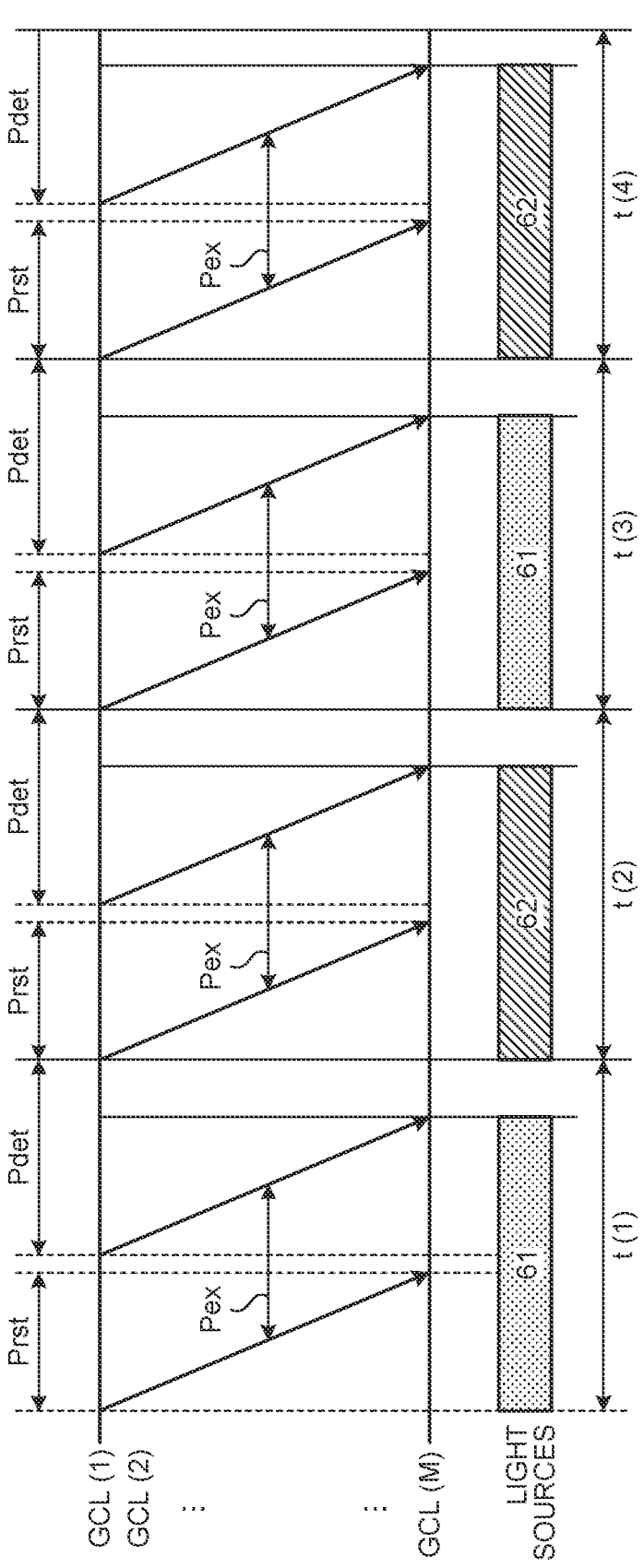
FIG. 10 is an explanatory chart for explaining a relation between driving of the sensor of the detection device and lighting operations of light sources.

The following describes an operation example of the detection device 1. FIG. 6 is a timing waveform chart illustrating the operation example of the detection device. FIG. 7 is a timing waveform chart illustrating an operation example during the reset period in FIG. 6. FIG. 8 is a timing waveform chart illustrating an operation example during the read period in FIG. 6. FIG. 9 is a timing waveform chart illustrating an operation example during a drive period of one gate line included in a row read period VR in FIG. 6. FIG. 10 is an explanatory chart for explaining a relation between driving of the sensor of the detection device and lighting operations of the light sources.

As illustrated in FIG. 6, the detection device 1 has the reset period Prst, an exposure period Pex, and the read period Pdet. The power supply circuit 123 supplies the sensor power supply potential VDDSNS to the anode of the optical sensor PD over the reset period Prst, the exposure period Pex, and the read period Pdet. The sensor power supply potential VDDSNS is a signal for applying a reverse bias between the anode and the cathode of the optical sensor PD. For example, the reference signal COM of substantially 0.75 V is applied to the cathode of the optical sensor PD, and the sensor power supply potential VDDSNS of substantially −1.25 V is applied to the anode thereof. As a result, a reverse bias of substantially 2.0 V is applied between the anode and the cathode. The control circuit 122 sets the reset signal RST2 to "H", and then, supplies the start signal STV and the clock signal CK to the gate line drive circuit 15 to start the reset period Prst. During the reset period Prst, the control circuit 122 supplies the reference signal COM to the reset circuit 17 and uses the reset signal RST2 to turn on the fourth switching elements TrR for supplying a reset voltage. This operation supplies the reference signal COM as the reset voltage to each of the signal lines SGL. The reference signal COM is set to, for example, 0.75 V.

During the reset period Prst, the gate line drive circuit 15 sequentially selects each of the gate lines GCL based on the start signal STV, the clock signal CK, and the reset signal RST1. The gate line drive circuit 15 sequentially supplies the gate drive signals Vgcl {Vgcl(1), . . . , Vgcl(M)} to the gate lines GCL. The gate drive signal Vgcl has a pulsed waveform having a power supply voltage VDD serving as a high-level voltage and a power supply voltage VSS serving as a low-level voltage. In FIG. 6, M gate lines GCL (where M is, for example, 256) are provided, and the gate drive signals Vgcl(1), . . . , Vgcl(M) are sequentially supplied to the respective gate lines GCL. Thus, the first switching elements Tr are sequentially brought into a conducting state and supplied with the reset voltage on a row-by-row basis. For example, a voltage of 0.75 V of the reference signal COM is supplied as the reset voltage.

Specifically, as illustrated in FIG. 7, the gate line drive circuit 15 supplies the gate drive signal Vgcl(1) at the high-level voltage (power supply voltage VDD) to the gate line GCL(1) during a period V(1). The control circuit 122 supplies any one of selection signals ASW1, . . . , ASW6 (selection signal ASW1 in FIG. 7) to the signal line selection circuit 16 during a period in which the gate drive signal Vgcl(1) is at the high-level voltage (power supply voltage VDD). This operation couples the signal line SGL of the partial detection area PAA selected by the gate drive signal Vgcl(1) to the detection circuit 48. As a result, the reset voltage (reference signal COM) is also supplied to coupling wiring between the third switching element TrS and the detection circuit 48.

In the same manner, the gate line drive circuit 15 supplies the gate drive signals Vgcl(2), . . . , Vgcl(M−1), Vgcl(M) at the high-level voltage to gate lines GCL(2), . . . , GCL(M−1), GCL(M) during periods V(2), . . . , V(M−1), V(M), respectively.

Thus, during the reset period Prst, the capacitive elements Ca of all the partial detection areas PAA are sequentially electrically coupled to the signal lines SGL, and are supplied with the reference signal COM. As a result, the capacitance of the capacitive elements Ca is reset. The capacitance of the capacitive elements Ca of some of the partial detection areas PAA can be reset by partially selecting the gate lines and the signal lines SGL.

Examples of the method of controlling the exposure include a method of controlling the exposure during non-selection of the gate lines and a method of always controlling the exposure. In the method of controlling the exposure during non-selection of the gate lines, the gate drive signals {Vgcl(1), . . . , Vgcl(M)} are sequentially supplied to all the gate lines GCL coupled to the optical sensors PD serving as the detection targets, and all the optical sensors PD serving as the detection targets are supplied with the reset voltage. Then, after all the gate lines GCL coupled to the optical sensors PD serving as the detection targets are set to a low voltage (the first switching elements Tr are turned off), the exposure starts and the exposure is performed during the exposure period Pex. After the exposure ends, the gate drive signals {Vgcl(1), . . . , Vgcl(M)} are sequentially supplied to the gate lines GCL coupled to the optical sensors PD serving as the detection targets as described above, and reading is performed during the read period Pdet. In the method of always controlling the exposure, the control for performing the exposure is also performed during the reset period Prst and the read period Pdet (the exposure is always controlled). In this case, the actual exposure period Pex(1) starts immediately after the gate drive signal Vgcl(1) supplied to the gate line GCL becomes L, H, and then L during the reset period Prst. The actual exposure periods Pex {(1), . . . , (M)} are periods during which the capacitive elements Ca are charged from the optical sensors PD. The electric charge stored in the capacitive element Ca during the reset period Prst causes a reverse directional current (from cathode to anode) to flow through the optical sensor PD due to light irradiation, and the potential difference in the capacitive element Ca decreases. The start timing and the end timing of the actual exposure periods Pex(1), . . . , Pex(M) are different among the partial detection areas PAA corresponding to the respective gate lines GCL. The "actual exposure period" is not a period during which the light source emits light but a period during which the electric charges corresponding to the light received by the optical sensors PD are stored in the respective capacitive elements Ca in the lighting period of the light source. Each of the exposure periods Pex(1), . . . , Pex(M) starts when the gate drive signal Vgcl changes from the power supply voltage VDD serving as the high-level voltage to the power supply voltage VSS serving as the low-level voltage during the reset period Prst. Each of the exposure periods Pex(1), . . . , Pex(M) ends when the gate drive signal Vgcl changes from the power supply voltage VSS to the power supply voltage VDD during the read period Pdet. The lengths of the exposure time of the exposure periods Pex(1), . . . , Pex(M) are equal.

During the exposure periods Pex {(1) . . . (M)}, a current corresponding to the light received by the optical sensor PD flows in each of the partial detection areas PAA. As a result, an electric charge is stored in each of the capacitive elements Ca.

At a time before the read period Pdet starts, the control circuit 122 sets the reset signal RST2 to a low-level voltage. This operation stops the operation of the reset circuit 17. The reset signal may be set to a high-level voltage only during the reset period Prst. During the read period Pdet, the gate line drive circuit 15 sequentially supplies the gate drive signals Vgcl(1) . . . , Vgcl(M) to the gate lines GCL in the same manner as during the reset period Prst.

Specifically, as illustrated in FIG. 8, the gate line drive circuit 15 supplies the gate drive signal Vgcl(1) at the high-level voltage (power supply voltage VDD) to the gate line GCL(1) during a row read period VR(1). The control circuit 122 sequentially supplies the selection signals ASW1, . . . , ASW6 to the signal line selection circuit 16 during a period in which the gate drive signal Vgcl(1) is at the high-level voltage (power supply voltage VDD). This operation sequentially or simultaneously couples the signal lines SGL of the partial detection areas PAA selected by the gate drive signal Vgcl(1) to the detection circuit 48. As a result, the detection signal Vdet for each of the partial detection areas PAA is supplied to the detection circuit 48.

In the same manner, the gate line drive circuit 15 supplies the gate drive signals Vgcl(2), . . . , Vgcl(M−1), Vgcl(M) at the high-level voltage to the gate lines GCL(2), . . . , GCL(M−1), GCL(M) during row read periods VR(2), . . . , VR(M−1), VR(M), respectively. That is, the gate line drive circuit 15 supplies the gate drive signal Vgcl to the gate line GCL during each of the row read periods VR(1), VR(2), . . . , VR(M−1), VR(M). The signal line selection circuit 16 sequentially selects each of the signal lines SGL based on the selection signal ASW in each period in which the gate drive signal Vgcl is set to the high-level voltage. The signal line selection circuit 16 sequentially couples each of the signal lines SGL to one detection circuit 48. Thus, the detection device 1 can output the detection signals Vdet of all the partial detection areas PAA to the detection circuit 48 during the read period Pdet.

With reference to FIG. 9, the following describes the operation example during the row read period VR that is a supply period of one of the gate drive signals Vgcl(j) in FIG. 6. In FIG. 6, the reference numeral of the row read period VR is assigned to the first gate drive signal Vgcl(1). The same applies to the other gate drive signals Vgcl(2) . . . , Vgcl(M). The index j is any one of the natural numbers 1 to M.

As illustrated in FIGS. 9 and 4, an output (Vout) of each of the third switching elements TrS has been reset to the reference potential (Vref) voltage in advance. The reference potential (Vref) voltage serves as the reset voltage and is set to, for example, 0.75 V. Then, the gate drive signal Vgcl(j) is set to a high level, and the first switching elements Tr of a corresponding row are turned on. Thus, each of the signal lines SGL in each row is set to a voltage corresponding to the electric charge stored in the capacitor (capacitive element Ca) of the partial detection area PAA. After a period t1 elapses from a rising edge of the gate drive signal Vgcl(j), a period t2 starts in which the selection signal ASW(k) is set to a high level. After the selection signal ASW(k) is set to the high level and the third switching element TrS is turned on, the electric charge stored in the capacitor (capacitive element Ca) of the partial detection area PAA coupled to the detection circuit 48 through the third switching element TrS changes the output (Vout) of the third switching element TrS (refer to FIG. 4) to a voltage corresponding to the electric charge stored in the capacitor (capacitive element Ca) of the partial detection area PAA (in a period t3). In the example of FIG. 9, this voltage is reduced from the reset voltage as illustrated in the period t3. Then, after the switch SSW is turned on (period t4 during which an SSW signal is set to a high level), the electric charge stored in the capacitor (capacitive element Ca) of the partial detection area PAA moves to the capacitor (capacitive element Cb) of the detection signal amplifier 42 of the detection circuit 48, and the output voltage of the detection signal amplifier 42 is set to a voltage corresponding to the electric charge stored in the capacitive element Cb. At this time, the potential of the inverting input portion of the detection signal amplifier 42 is set to an imaginary short-circuit potential of an operational amplifier, and therefore, becomes the reference potential (Vref). The A/D converter 43 reads the output voltage of the detection signal amplifier 42. In the example of FIG. 9, waveforms of the selection signals ASW(k), ASW(k+1), . . . corresponding to the signal lines SGL of the respective columns are set to a high level to sequentially turn on the third switching elements TrS, and the same operation is sequentially performed to sequentially read the electric charges stored in the capacitors (capacitive elements Ca) of the partial detection areas PAA coupled to the gate line GCL. ASW(k), ASW(k+1), . . . in FIG. 9 are, for example, any of ASW1 to ASW6 in FIG. 9.

Specifically, after the period t4 starts in which the switch SSW is on, the electric charge moves from the capacitor (capacitive element Ca) of the partial detection area PAA to the capacitor (capacitive element Cb) of the detection signal amplifier 42 of the detection circuit 48. At this time, the non-inverting input (+) of the detection signal amplifier 42 is set to the reference potential (Vref) voltage (for example, 0.75 V). As a result, the output (Vout) of the third switching element TrS is also set to the reference potential (Vref) voltage due to the imaginary short-circuit between input ends of the detection signal amplifier 42. The voltage of the capacitive element Cb is set to a voltage corresponding to the electric charge stored in the capacitor (capacitive element Ca) of the partial detection area PAA at a location where the third switching element TrS is turned on in response to the selection signal ASW(k). After the output (Vout) of the third switching element TrS is set to the reference potential (Vref) voltage due to the imaginary short-circuit, the output of the detection signal amplifier 42 reaches a voltage corresponding to the capacitance of the capacitive element Cb, and this output voltage is read by the A/D converter 43. The voltage of the capacitive element Cb is, for example, a voltage between two electrodes provided on a capacitor constituting the capacitive element Cb.

The period t1 is, for example, 20 μs. The period t2 is, for example, 60 μs. The period t3 is, for example, 44.7 μs. The period t4 is, for example, 0.98 μs.

As illustrated in FIG. 10, in each of a period t(1), a period t(2), a period t(3), and a period t(4), the detection device 1 performs the processing in the reset period Prst, the exposure periods Pex {(1), . . . , (M)}, and the read period Pdet described above. In the reset period Prst and the read period Pdet, the gate line drive circuit 15 sequentially scans the gate lines from GCL(1) to GCL(M). In the following description, the term "one-frame detection" denotes detection operation of one frame, that is, the detection in each period t. More specifically, "one-frame detection" denotes the detection in which the gate lines are scanned from GCL(1) to GCL(M) in the reset period Prst and the read period Pdet and the detection signals Vdet are acquired from the signal lines SGL in the respective columns.

The control circuit 122 can control the lighting and the non-lighting of the light sources according to the detection target. FIG. 10 illustrates an example in which the first light sources 61 are on during the periods t(1) and t(3), and the second light sources 62 are on during the periods t(2) and t(4). That is, in the example illustrated in FIG. 10, the control circuit 122 alternately switches the first light sources 61 and the second light sources 62 between on and off for each one-frame detection. The present disclosure is not limited to this example. For example, the control circuit 122 may switch the first light sources 61 and the second light sources 62 between on and off at intervals of a predetermined period of time, or may continuously turn on either of the first light sources 61 and the second light sources 62.

Although FIGS. 6 to 10 illustrate the example in which the gate line drive circuit 15 individually selects the gate line GCL, the present disclosure is not limited to this example. The gate line drive circuit 15 may simultaneously select a predetermined number (two or more) of the gate lines GCL, and sequentially supply the gate drive signals Vgcl to the gate lines GCL in units of the predetermined number of the gate lines GCL. The signal line selection circuit 16 may also simultaneously couple a predetermined number (two or more) of the signal lines SGL to one detection circuit 48. Moreover, the gate line drive circuit 15 may scan some of the gate lines GCL while skipping the others.

As illustrated in FIG. 8, in the row read period VR(1), the selection signals ASW1, . . . , ASW6 are sequentially supplied to the signal line selection circuit 16 during the period in which the gate drive signal Vgcl(1) is at the high-level voltage (power supply voltage VDD). That is, even after the selection signal ASW1 is set to a low-level voltage at time t11, the exposure continues during an exposure period Pex-1 until the gate drive signal Vgcl(1) is set to the low-level voltage at time t13. The signal line SGL(1) corresponding to the selection signal ASW1 is charged with an electric charge corresponding to the exposure period Pex-1 from the optical sensor PD.

In the same manner, each of the signal lines SGL is charged with an electric charge during a corresponding one of exposure periods Pex-1, . . . , Pex-6 corresponding to the selection signals ASW1, . . . , ASW6. For example, the exposure period Pex-6 is a period after the selection signal ASW6 is set to the low-level voltage at time t12 until the gate drive signal Vgcl(1) is set to the low-level voltage at time t13, and the exposure period Pex differs column by column.

In the next row read period VR(2), the detection circuit 48 is supplied with a signal obtained by adding an electric charge stored during the exposure periods Pex-1 (SGL(1)), . . . , Pex-6(SGL(6)) of the previous row read period VR(1) to the detection signal Vdet of the second row.

As described above, the detection device 1 has the configuration including, for example, a plurality of types of light sources (first light sources 61 and second light sources 62) that emit light having different wave lengths, and thereby, can acquire a fingerprint acquired by detecting the light reflected on the surface of a finger of the subject and the various types of biometric information acquired by detecting the light reflected in or transmitted through the finger or the wrist of the subject.

Figure 11:
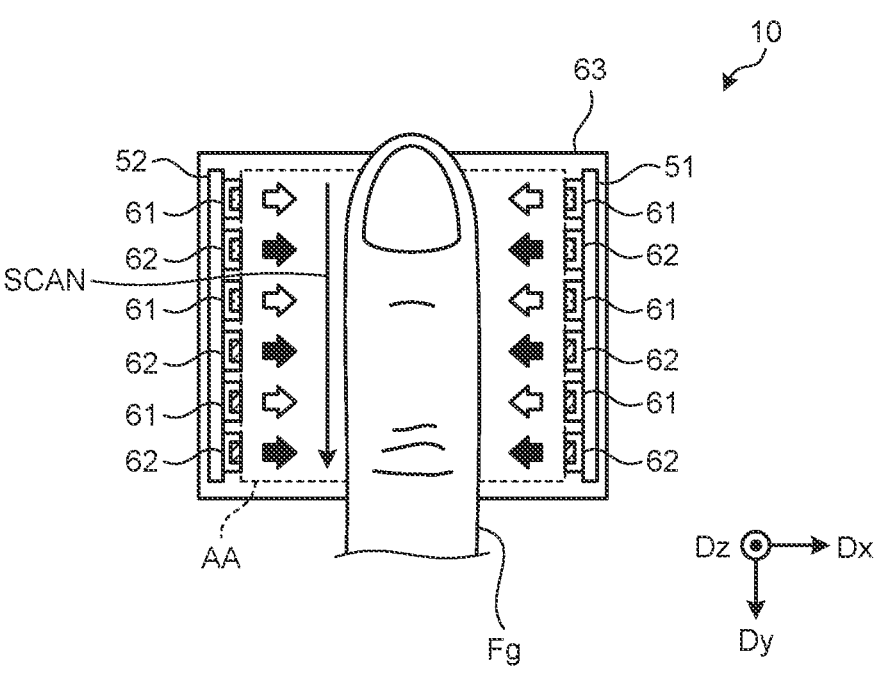
FIG. 11 is a plan view schematically illustrating a relation between the sensor, first light sources, and second light sources in the detection device according to the embodiment.

As a specific example of the information on the living body acquired by the detection device 1, the following describes an example of acquiring the pulse waves serving as biometric information for calculating an oxygen saturation level in the blood (hereinafter, called "blood oxygen saturation level" (SpO$_2$)). FIG. 11 is a plan view schematically illustrating a relation between the sensor, the first light sources, and the second light sources in the detection device according to the embodiment.

As illustrated in FIG. 11, the detection device 1 includes a filter 63. The filter 63 is disposed so as to overlap the detection area AA from one end to the other end in a scan direction SCAN of the sensor 10. The filter 63 has a transmission bandwidth for transmitting the first light emitted from the first light sources 61 and the second light emitted from the second light sources 62. In a configuration according to the embodiment, the filter 63 is not required, and the configuration may exclude the filter 63.

In the configuration illustrated in FIG. 11, the scan direction SCAN is the direction in which the gate line drive circuit 15 scans the gate line GCL. That is, one gate line GCL is provided so as to extend in the first direction Dx in the detection area AA and is coupled to the partial detection areas PAA provided in the detection area AA. One signal line SGL is provided so as to extend in the second direction Dy in the detection area AA, and is coupled to the optical sensors PD in the detection area AA.

The first light source base member 51 and the second light source base member 52 face each other in the first direction Dx with the detection area AA interposed therebetween in the plan view. The first and the second light sources 61 and 62 are provided on a surface of the first light source base member 51 facing the second light source base member 52. The first and the second light sources 61 and 62 are also provided on a surface of the second light source base member 52 facing the first light source base member 51. The first and the second light sources 61 and 62 are arranged in the first direction Dx along the periphery of the detection area AA and are alternately provided in the second direction Dy on each of the first light source base member 51 and the second light source base member 52.

The first light sources 61 emit the first light in a direction parallel to the first direction Dx. As a result, the detection area AA is irradiated by the first light. The second light sources 62 emit the second light in the direction parallel to the first direction Dx. As a result, the detection area AA is irradiated by the second light.

Figure 12:
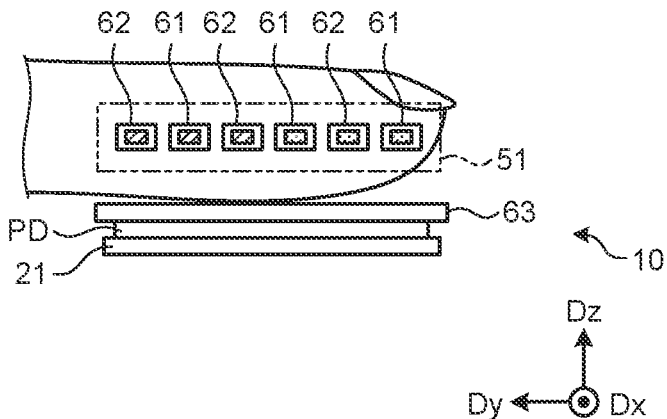
FIG. 12 is a side view of the detection device illustrated in FIG. 11 as viewed in a first direction.

FIG. 12 is a side view of the detection device illustrated in FIG. 11 as viewed in the first direction Dx. As illustrated in FIG. 12, the object to be detected such as the finger Fg or the wrist of the subject comes in contact with or in proximity to the top of the sensor 10 with the filter 63 interposed therebetween. The first and the second light sources 61 and 62 are arranged above the sensor 10 and the filter 63, and are arranged with the object to be detected such as the finger Fg or the wrist of the subject interposed therebetween in the first direction Dx.

In this example, visible light in red (red light) having a wavelength of from 600 nm to 700 nm, specifically, approximately 660 nm is employed as the first light emitted from the first light sources 61, and infrared light having a wavelength of from 780 nm to 950 nm, specifically, approximately 850 nm is employed as the second light emitted from the second light sources 62. In the case of acquiring the human blood oxygen saturation level (SpO$_2$), a pulse wave acquired using the first light (red light) and a pulse wave acquired using the second light (infrared light) are used.

Since the amount of light absorbed by hemoglobin changes with the amount of oxygen absorbed by the hemoglobin, the optical sensor PD detects the amount of light obtained by subtracting the amount of the light absorbed by blood (hemoglobin) from the amount of the emitted first and second light. Most of the blood oxygen is reversibly bound to hemoglobin in red blood cells, and a small fraction of the blood oxygen is dissolved in blood plasma. More specifically, the value of what percentage of the allowable amount of oxygen is bound to the blood as a whole is called "oxygen saturation level" (SpO$_2$). The blood oxygen saturation level can be calculated from the amount obtained by subtracting the amount of the light absorbed by the blood (hemoglobin) from the amount of the light emitted at the two wavelengths of the first light and the second light.

The oxygen saturation level (SpO$_2$) is determined by the ratio of hemoglobin in blood bound to oxygen (oxygenated hemoglobin (O2Hb)) to hemoglobin in blood not bound to oxygen (reduced hemoglobin (HHb)). The light absorption characteristics of red light are represented as HHb>>O2Hb, indicating that HHb has significantly larger absorbance, while the light absorption characteristics of infrared light are represented as HHb≈O2Hb, indicating that O2Hb has slightly larger absorbance.

The first light emitted from the first light sources 61 travels in the direction parallel to the first direction Dx and enters the finger Fg or the wrist of the subject. The first light emitted from the first light sources 61 penetrates into the living body and is reflected in the finger Fg or the wrist of the subject. The reflected light reflected in the finger Fg or the wrist of the subject travels in the third direction Dz, and enters the detection area AA of the sensor 10 through the filter 63.

The second light emitted from the second light sources 62 travels in the direction parallel to the first direction Dx and enters the finger Fg or the wrist of the subject. The second light emitted from the second light sources 62 penetrates into the living body and is reflected in the finger Fg or the wrist of the subject. The reflected light reflected in the finger Fg or the wrist of the subject travels in the third direction Dz and enters the detection area AA of the sensor 10 through the filter 63.

The arrangement of the first and the second light sources 61 and 62 is not limited to the example illustrated in FIGS. 11 and 12. For example, the first and the second light may be emitted from above the object to be detected such as the finger Fg or the wrist of the subject illustrated in FIG. 12, specifically, in the third direction Dz. Alternatively, the first and the second light sources 61 and 62 may be, for example, what are called direct-type light sources provided directly below the detection area AA.

In the example illustrated in FIG. 10, the reset period Prst, the exposure period Pex, and the read period Pdet are provided in the one-frame detection in each of the periods t(1), t(2), t(3), and t(4). In the reset period Prst and the read period Pdet, the gate line drive circuit 15 sequentially scans the gate lines from GCL(1) to GCL(M).

As illustrated in FIG. 10, in the one-frame detection in the period t(1), the control circuit 122 (detection controller 11) controls the first light sources 61 to be on and the second light sources 62 to be off during the exposure period Pex. In the one-frame detection in the period t(2), the control circuit 122 (detection controller 11) controls the first light sources 61 to be off and the second light sources 62 to be on during the exposure period Pex. In the same manner, the first light sources 61 are controlled to be on and the second light sources 62 are controlled to be off during the exposure period Pex in the one-frame detection in the period t(3), and the first light sources 61 are controlled to be off and the second light sources 62 are controlled to be on during the exposure period Pex in the one-frame detection in the period t(4).

Thus, the first and the second light sources 61 and 62 are controlled to be on and off in a time-division manner for each one-frame detection. With this control, a first detection signal detected by the optical sensor PD based on the first light and a second detection signal detected by the optical sensor PD based on the second light are output to the detection circuit 48 in a time-division manner.

Since the calculation of the blood oxygen saturation level (SpO$_2$) uses the pulse wave acquired using the first light and the pulse wave acquired using the second light, the gap in detection timing between the first detection signal detected based on the first light and the second detection signal detected based on the second light is preferably smaller. The following describes an operation example that can reduce the gap in detection timing between the first detection signal detected based on the first light and the second detection signal detected based on the second light, with reference to FIGS. 13 and 14.

Figure 13:
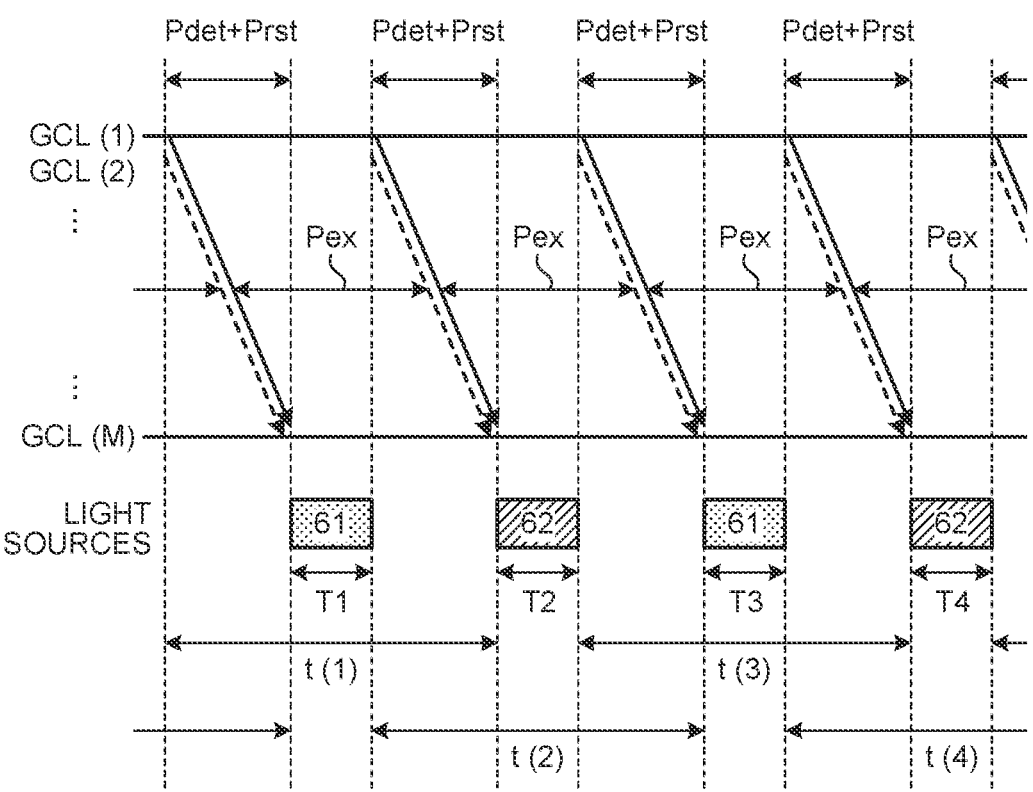
FIG. 13 is an explanatory chart for explaining an operation example of the detection device according to the embodiment.
Figure 14:
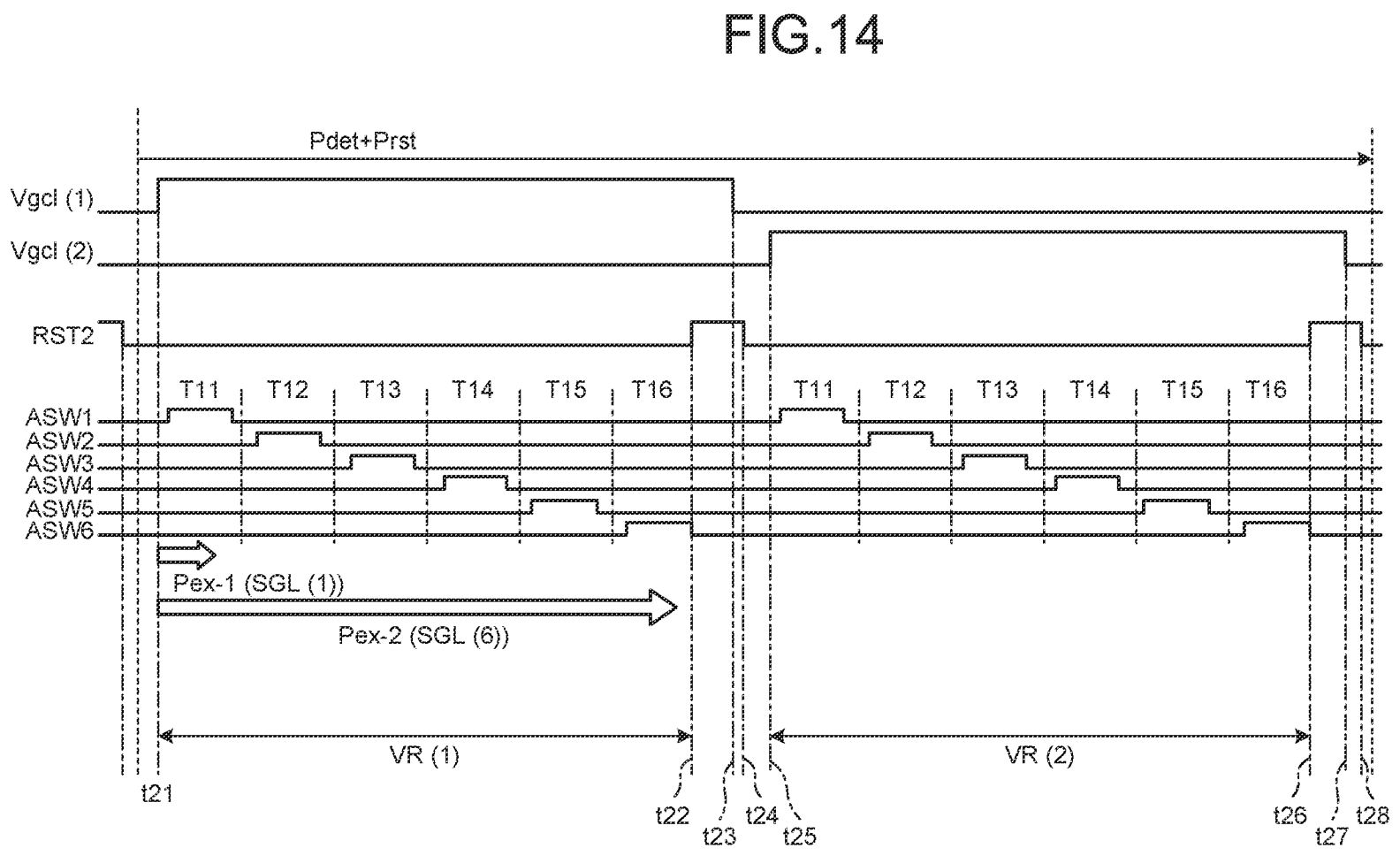

FIG. 13 is an explanatory chart for explaining the operation example of the detection device according to the embodiment. FIG. 14 is a timing waveform chart illustrating the operation example of the detection device according to the embodiment. The example illustrated in FIG. 13 indicates the reset period Prst with a solid arrow and the read period Pdet with a dashed arrow for each of the periods t(1), t(2), t(3), and t(4).

In the operation example illustrated in FIG. 13, the reset period Prst of the period t(1) provided with a period T1 to turn on the first light sources 61 is executed in parallel with the read period Pdet of the previous frame. The reset period Prst of the period t(2) provided with a period T2 to turn on the second light sources 62 is executed in parallel with the read period Pdet of the previous frame. Subsequently, in the same manner, the reset period Prst of the period t(3) provided with a period T3 to turn on the first light sources 61 is executed in parallel with the read period Pdet of the previous frame, and the reset period Prst of the period t(4) provided with a period T4 to turn on the second light sources 62 is executed in parallel with the read period Pdet of the previous frame. Specifically, for example, immediately after each row of the frame for the period t(1) is read, the row of the frame for the period t(2) is reset and irradiated with light during the period T2. Then, immediately after each row of the frame for the period t(2) is read, the row of the frame for the period t(3) is reset and irradiated with light during the period T3. Subsequently, the same operation is repeated. This operation reduces the gap in detection timing between the detection based on the first light emitted from the first light sources 61 and the detection based on the first light emitted from the second light sources 62 in each row.

In the operation example illustrated in FIG. 13, the gate drive signal Vgcl is supplied to the gate lines GCL row by row, and the first switching elements Tr belonging to a certain row are brought into a coupled state. Specifically, as illustrated in FIG. 14, the gate line drive circuit 15 supplies the gate drive signal Vgcl(1) at the high-level voltage (power supply voltage VDD) to the gate line GCL(1) at time t21. The row read period VR(1) starts at time t21 when the gate drive signal Vgcl(1) is set to the high-level voltage.

Specifically, the control circuit 122 sequentially supplies the selection signals ASW1, . . . , ASW6 to the signal line selection circuit 16 during a period in which the gate drive signal Vgcl(1) is at the high-level voltage (power supply voltage VDD). The third switching elements TrS are sequentially brought into the coupled state in response to the selection signals ASW1, . . . , ASW6. That is, during the period of reading each row (row read period VR(1)), when the first switching elements Tr of the certain row are in the coupled state, the signal line selection circuit 16 couples the signal lines SGL to the detection circuit 48 column by column in a predetermined order. As a result, the detection signal Vdet for each of the partial detection areas PAA is supplied to the detection circuit 48.

In FIG. 14, the selection signals ASW1, . . . , ASW6 are supplied in the order of periods T11, . . . , T16 in a time-division manner. At time t22, the control circuit 122 sets the selection signal ASW6 to the low-level voltage, and the reading of the last column ends. That is, the row read period VR(1) ends when the gate drive signal Vgcl(1) is at the high-level voltage and the selection signal ASW6 has changed to the low-level voltage.

After the completion of the read period of the certain row (row read period VR(1)) and before the start of the read period of a row next to the certain row (row read period VR(2)), a reset potential (reference signal COM) is supplied to the optical sensors PD and the signal lines SGL belonging to the certain row. Specifically, the control circuit 122 supplies the reset signal RST2 to the reset signal line Lrst at time t22. This operation turns on the fourth switching elements TrR to supply the reference signal COM to the optical sensors PD and the signal lines SGL corresponding to the gate line GCL(1).

In the example illustrated in FIG. 14, at time t22, the time when the reset signal RST2 is set to the high-level voltage coincides with the time when the selection signal ASW6 is set to the low-level voltage. However, the timing is not limited thereto. The reset signal RST2 may be set to the high-level voltage after a predetermined period of time has elapsed since the selection signal ASW6 has been set to the low-level voltage.

Then, at time t23, the gate line drive circuit 15 sets the gate drive signal Vgcl(1) to the low-level voltage. This operation brings the first switching elements Tr of the certain row into a non-coupled state. At time t24, the control circuit 122 sets the reset signal RST2 to the low-level voltage. This operation ends the read period Pdet and reset period Prst of the first row.

Then, at time t25, the gate line drive circuit 15 supplies the gate drive signal Vgcl(2) at the high-level voltage (power supply voltage VDD) to the gate line GCL(2) of the second row. Subsequently, in the same manner as in the first row, the read period Pdet and the reset period Prst of the second row are executed from time t26 to time t28. The one-frame detection can be performed by repeating this operation to the last row (gate line GCL(256)).

During the periods T1, T2, T3, and T4 (refer to FIG. 13) in which the light sources are turned on, none of the gate lines GCL is selected (the gate drive signals Vgcl are at the low-level voltage). That is, the light sources are off during the row read period VR in which the first switching elements Tr in the certain row are in the coupled state, and the light sources are on during the periods T1, T2, T3, and T4 in which all the first switching elements Tr are in the non-coupled state.

As described above, in the example illustrated in FIGS. 13 and 14, the read period Pdet and the reset period Prst in the detection operations of two consecutive frames are executed in parallel. Thus, the gap in detection timing between the first detection signal detected based on the first light and the second detection signal detected based on the second light can be reduced.

Figure 15:
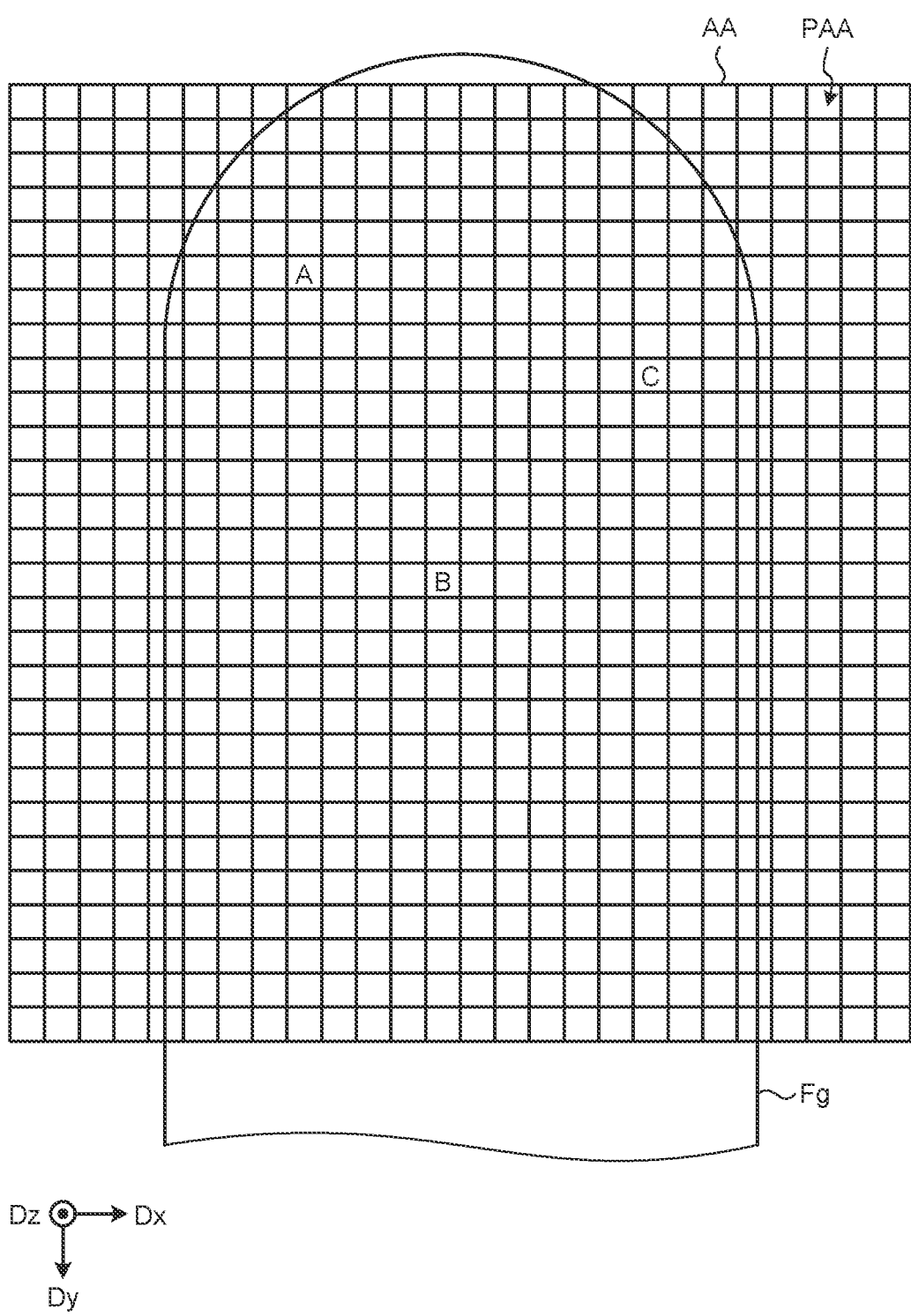
FIG. 15 is a schematic view illustrating a positional relation between a detection area of the sensor and an object to be detected.

FIG. 15 is a schematic view illustrating a positional relation between the detection area of the sensor and the object to be detected. FIG. 15 illustrates the finger Fg of the subject as the object to be detected.

Figure 16A:
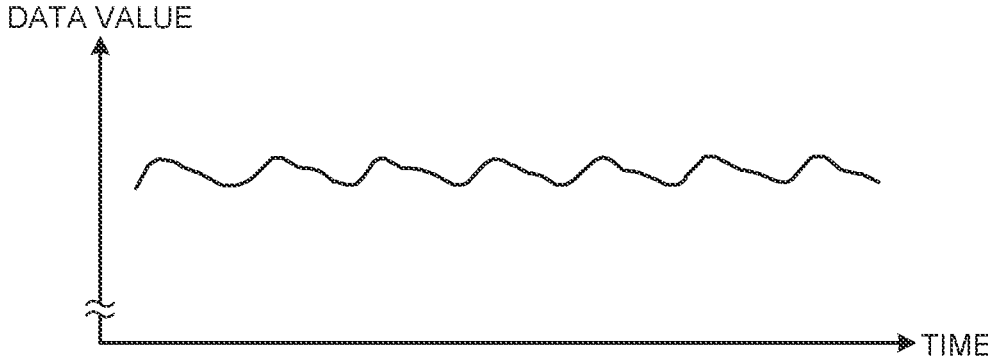
FIG. 16A is a chart illustrating a waveform of a pulse wave acquired based on a detection signal detected in a partial detection area A illustrated in FIG. 15.
Figure 16B:
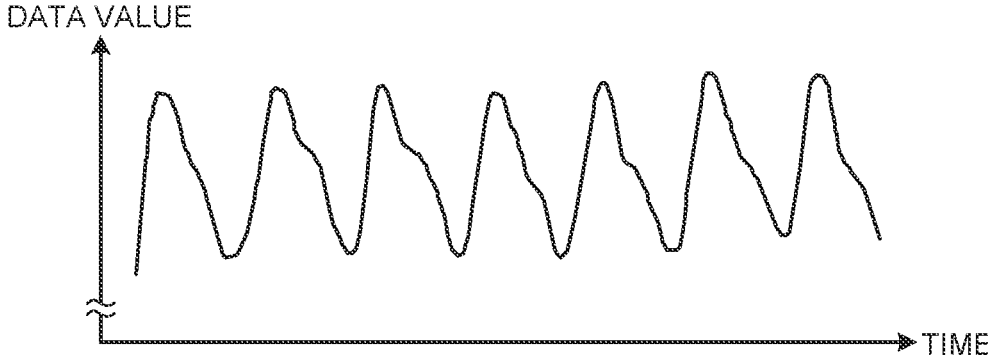
FIG. 16B is a chart illustrating the waveform of the pulse wave acquired based on the detection signal detected in a partial detection area B illustrated in FIG. 15.
Figure 16C:
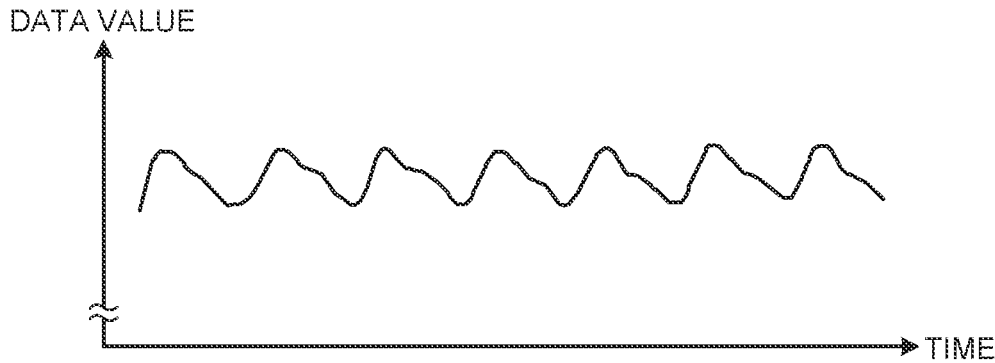
FIG. 16C is a chart illustrating the waveform of the pulse wave acquired based on the detection signal detected in a partial detection area C illustrated in FIG. 15.

FIG. 16A is a chart illustrating a waveform of a pulse wave acquired based on the detection signal detected in a partial detection area A illustrated in FIG. 15. FIG. 16B is a chart illustrating the waveform of the pulse wave acquired based on the detection signal detected in a partial detection area B illustrated in FIG. 15. FIG. 16C is a chart illustrating the waveform of the pulse wave acquired based on the detection signal detected in a partial detection area C illustrated in FIG. 15. In FIGS. 16A, 16B, and 16C, the horizontal axis represents time, and the vertical axis represents the data value of the pulse wave data.

Figure 17:
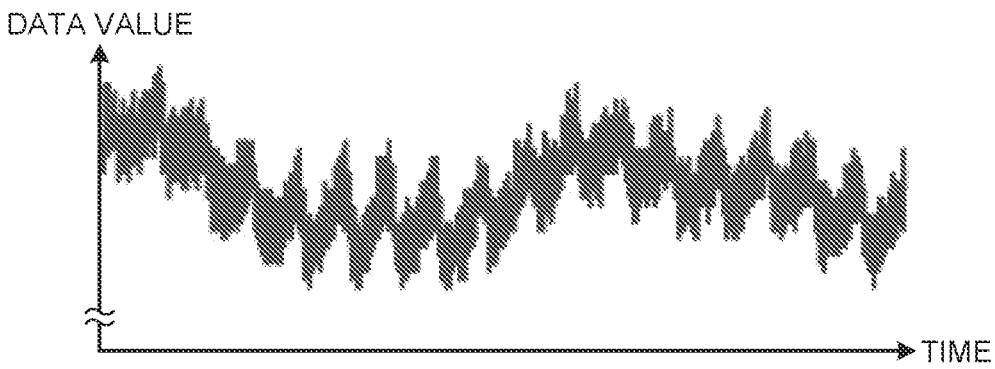
FIG. 17 is a chart illustrating an exemplary detection signal waveform.

FIG. 17 is a chart illustrating an exemplary detection signal waveform. In FIG. 17, the horizontal axis represents time, and the vertical axis represents the data value after A/D conversion of the detection signal Vdet.

In the following description, the magnitude of a peak-to-peak value (P-P value) of the data value in FIGS. 16A, 16B, 16C, and 17 is referred to as a "signal strength".

The strength of the signal detected in each of the partial detection areas PAA in the detection area AA differs depending on the distribution of subcutaneous blood vessels in the finger Fg of the subject. Specifically, for example, the signal strength of the pulse wave (FIG. 16B) acquired based on the detection signal Vdet detected in the partial detection area B illustrated in FIG. 15 is relatively larger than the signal strength of the pulse wave (FIG. 16A) acquired based on the detection signal Vdet detected in the partial detection area A illustrated in FIG. 15 and the signal strength of the pulse wave (FIG. 16C) acquired based on the detection signal Vdet detected in the partial detection area C illustrated in FIG. 15.

The detection signal Vdet detected in each of the partial detection areas PAA in the detection area AA includes noise components caused by disturbances and body movements of the subject, as illustrated in FIG. 17.

In the present disclosure, as preprocessing for acquiring the pulse wave data, extraction of one or more partial detection areas PAA is performed. In the extraction, from among the partial detection areas PAA in the detection area AA, one or more partial detection areas PAA are extracted in each of which the data having relatively larger signal strength is acquired. Then, data on the living body (in this case, the pulse wave data) is acquired based on the detection signals Vdet detected in a biometric data acquisition area BAA including the one or more extracted partial detection areas PAA. As a result, the highly accurate data on the living body can be acquired.

Measurement of SpO₂

SpO₂ serving as the biometric information can be acquired by measuring the light transmitted through the living body such as the finger. For example, SpO₂ can be measured using Expression (1) below.

$$SpO_2 = b - a*R \quad (1)$$

In Expression (1) above, "a" and "b" are predetermined coefficients. R in Expression (1) is defined by Expression (2) below.

$$R = \frac{AC_{Red}/DC_{Red}}{AC_{IR}/DC_{IR}} \quad (2)$$

In Expression (2) above, $AC_{Red}$ denotes the alternating-current (AC) component of the measurement value of the Red light; $DC_{Red}$ denotes the direct-current (DC) component of the measurement value of the Red light; $AC^{IR}$ denotes the AC component of the measurement value of the infrared (IR) light; and $DC_{IR}$ denotes the DC component of the measurement value of the IR light. The AC component is a component of the pulse wave that appears in a direct current.

Figure 18:
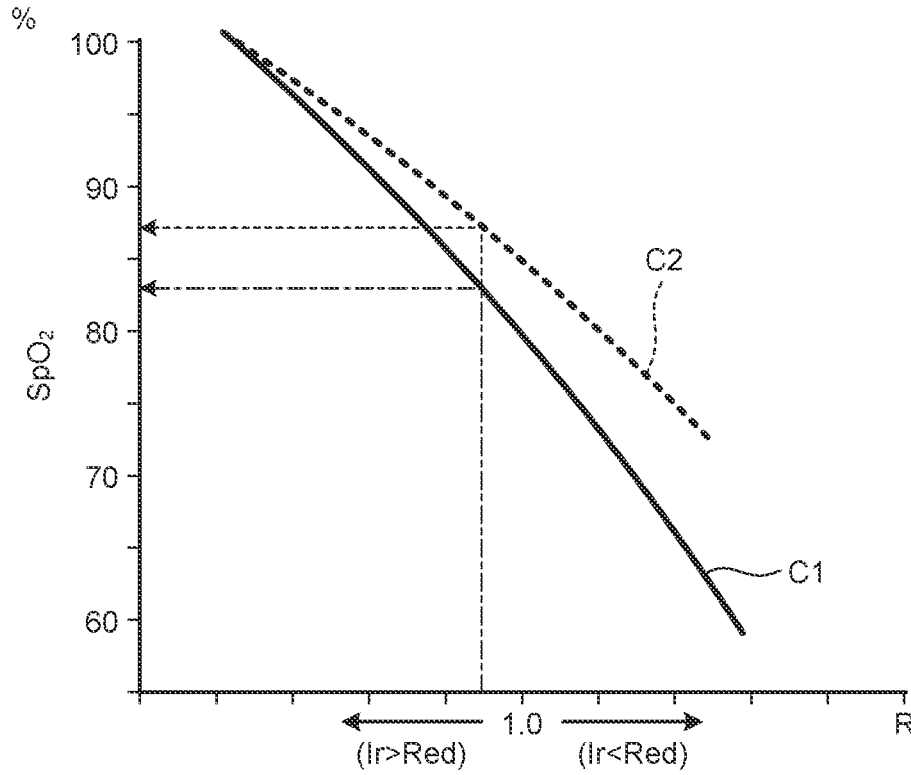
FIG. 18 is a chart illustrating examples of a value of SpO$_2$.

More specifically, the value of SpO₂ can be obtained in the following way. That is, the values of SpO₂ corresponding to the values of R mentioned above are measured in advance, and the value of SpO₂ is obtained based on the curve of the measurement values. The curve of the measurement values is as illustrated in FIG. 18, for example. FIG. 18 is a chart illustrating examples of the value of SpO₂. In FIG. 18, the horizontal axis represents the calculated value of R mentioned above, and the vertical axis represents the value of SpO₂. If the pulsation of the Ir light is greater than that of the RED light (Ir>Red), R has a smaller value than 1.0, and if the pulsation of the RED light is greater than that of the Ir light (Ir<Red), R has a larger value than 1.0.

As illustrated in FIG. 18, by calculating the value of R mentioned above, the value of SpO₂ corresponding to the value of R can be obtained. For example, by using a curve C1 in FIG. 18, a value of SpO₂ of approximately 83% can be obtained when the value of R is 0.9. For example, by using a curve C2 in FIG. 18, a value of SpO₂ of approximately 87% can be obtained when the value of R is 0.9.

Alternatively, by determining the coefficients a and b mentioned above to obtain an approximate expression of the curve C1 or the curve C2, the value of SpO₂ can be obtained using Expression (1).

Since SpO₂ serving as the biometric information is defined by Expressions (1) and (2), if the light quantity is too small, the AC component cannot be detected and only the DC component is detected, thus making it impossible to obtain highly accurate data. In addition, since the ratio between the measurement value of the IR light and the measurement value of the Red light is used, if either of these values is too large or too small, the correct value cannot be obtained. For these reasons, the initialization needs be properly performed before the measurement.

If only one sensor is provided, adjusting the light quantities of the light sources completes the initialization. For example, when the sensor receives a greater amount of the IR light than the Red light, the light quantity of the Red light is made to be increased to have the same level as the light quantity of the IR light.

In contrast, as illustrated in FIG. 3, when a plurality of sensors are provided, that is, when a plurality of detection areas (partial detection areas PAA) are provided in the detection area AA as described above, the light quantities of all the sensors are difficult to be adjusted to the same level because of problems such as distribution of light.

Initialization of Light Quantities of Light Sources

The following describes setting of initial values of the light quantities of the first and the second light sources 61 and 62. By properly setting the initial values of the light quantities of the first and the second light sources 61 and 62, the highly accurate data on the living body can be acquired. The following describes the setting of the initial values of the light quantities of the first and the second light sources 61 and 62.

First Example of Initialization

The following describes an example of the initialization of the light quantities of the first and the second light sources

Figure 19:
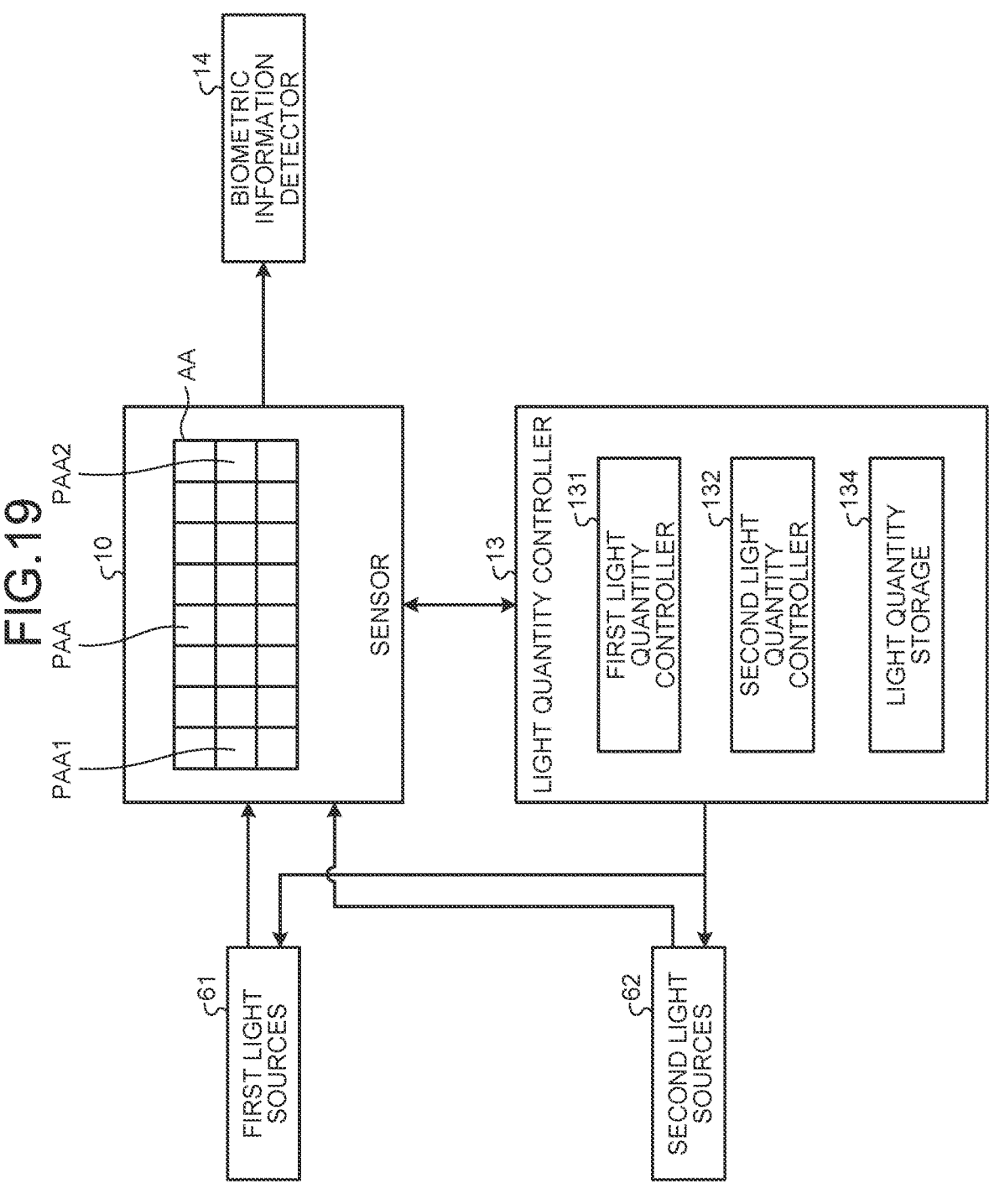
FIG. 19 is a diagram explaining a first configuration example for initializing light quantities of the light sources.

61 and 62. FIG. 19 is a diagram explaining a first configuration example for initializing the light quantities of the light sources.

Referring to FIG. 19, the first configuration for performing the initialization includes the first light sources 61, the second light sources 62, the sensor 10, a light quantity controller (light quantity control circuit) 13, and a biometric information detector (biometric information detection circuit) 14.

The first light sources 61 emit light having a predetermined wavelength. The second light sources 62 emit light having a wavelength different from the wavelength of the light emitted by the first light sources 61. That is, the first and the second light sources 61 and 62 emit light having different wavelengths from each other.

In this example, the first light sources 61 are light sources that emit infrared light (hereinafter, called "IR light"). In this example, the second light sources 62 are light sources that emit red light (hereinafter, called "Red light").

The sensor 10 includes the detection area AA described with reference to FIG. 1. As described above, the detection area AA includes the partial detection areas PAA each serving as a sensor. That is, the sensor 10 includes a plurality of optical sensors. The sensor 10 includes the optical sensors that detect the light emitted by the first and the second light sources 61 and 62, and are provided at different locations from each other.

The light quantity controller 13 controls the light quantities of the first and the second light sources 61 and 62. The light quantity controller 13 includes a first light quantity controller (first light quantity control circuit) 131 and a second light quantity controller second light quantity control circuit) 132. The first light quantity controller 131 sets the light quantity of the first light sources 61. The first light quantity controller 131 changes the light quantity of the first light sources 61. The second light quantity controller 132 sets the light quantity of the second light sources 62. The second light quantity controller 132 changes the light quantity of the second light sources 62.

The light quantity controller 13 also includes a light quantity storage (light quantity storage circuit) 134. When the increased light quantity of the first light sources 61 and the increased light quantity of the second light sources 62 have each reached a predetermined target value, the light quantity storage 134 stores therein the light quantity set by the first light quantity controller 131 and the light quantity set by the second light quantity controller 132 as light quantities for biometric information detection. That is, the light quantity storage 134 does not store therein in advance the light quantities set by the first light quantity controller 131 and the second light quantity controller 132. The light quantity storage 134 stores therein the light quantities set by the first light quantity controller 131 and the second light quantity controller 132 when the average value between a measurement value by a partial detection area PAA1 and a measurement value by a partial detection area PAA2 of the sensor 10 has reached a target value. The light quantities stored by the light quantity storage 134 serve as light quantities that are initially set when the biometric information detector 14 detects the biometric information. That is, the light quantities for biometric information detection are stored in the light quantity storage 134.

The biometric information detector 14 detects the biometric information based on the light from the first and the second light sources 61 and 62 that emit the light at the light quantities for biometric information detection stored in the light quantity storage 134.

Figure 20:
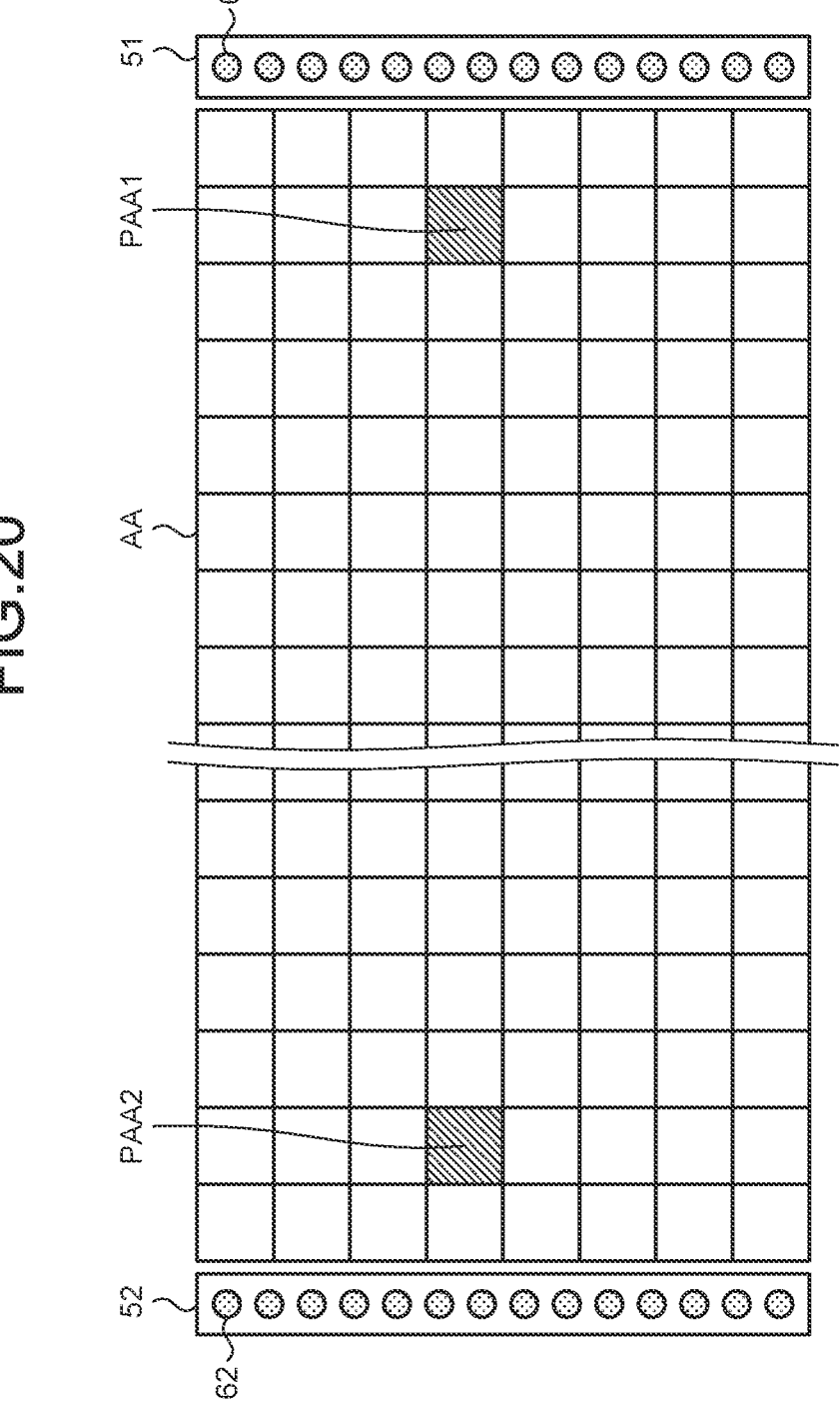
FIG. 20 is a plan view illustrating an exemplary arrangement of the light sources with respect to the detection area of the sensor.

FIG. 20 is a plan view illustrating an exemplary arrangement of the light sources with respect to the detection area AA of the sensor 10. As illustrated in FIG. 20, in this example, the detection area AA is provided between the first and the second light sources 61 and 62. That is, the first and the second light sources 61 and 62 are provided at locations interposing the detection area AA of the sensor 10 therebetween.

This example focuses on the partial detection areas PAA1 and PAA2 in the detection area AA of the sensor 10. The partial detection area PAA1 of the detection area AA is provided at a location closer to the first light source base member 51. The partial detection area PAA2 of the detection area AA is provided at a location closer to the second light source base member 52. In this example, the average value of the measurement values by the partial detection areas PAA1 and PAA2 is calculated.

The locations of the partial detection areas PAA1 and PAA2 illustrated in FIG. 20 are merely exemplary, and the average value of the measurement values by the partial detection areas PAA at two other locations may be calculated. Alternatively, the average value of the measurement values by the partial detection area PAA at three or more locations may be calculated.

Referring back to FIG. 19, the first light quantity controller 131 increases the light quantity of the IR light (hereinafter, called "IR light quantity") of the first light sources 61 until the average value of the measurement values by the partial detection areas PAA1 and PAA2 reaches the target value. That is, the first light quantity controller 131 increases the IR light quantity until the average value of the measurement values of the optical sensors reaches the target value. The second light quantity controller 132 increases the light quantity of the Red light (hereinafter, called "Red light quantity") of the second light sources 62 until the average value of the measurement values by the partial detection areas PAA1 and PAA2 reaches the target value. That is, the second light quantity controller 132 increases the Red light quantity until the average value of the measurement values of the optical sensors reaches the target value. The control of the light quantity of the light sources is performed by setting a pulse width modulation (PWM) value. The target value is, for example, 80% of the maximum detection value of the optical sensor.

The first light quantity controller 131 sets the light quantity of the first light sources 61 by changing the duty cycle of the pulse of the voltage to be applied to the first light sources 61. The second light quantity controller 132 sets the light quantity of the second light sources 62 by changing the duty cycle of the pulse of the voltage to be applied to the second light sources 62.

Figure 21:
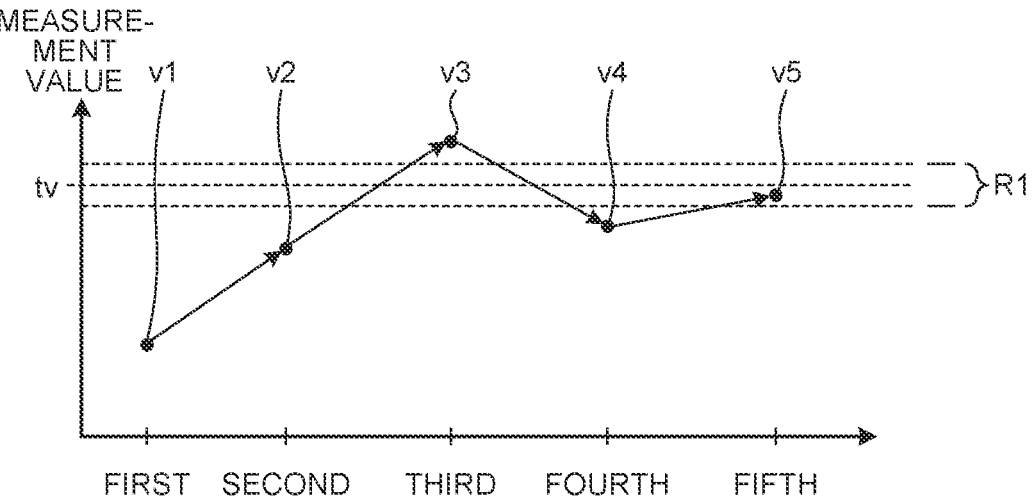
FIG. 21 is a graph illustrating an example of change in measurement value of a light quantity.

FIG. 21 is a graph illustrating an example of change in the measurement value of the light quantity. In FIG. 21, the vertical axis represents the measurement value, and the horizontal axis represents the number of times of measurement. As illustrated in FIG. 21, the measurement is repeated while increasing the light quantity until the measurement value reaches within a predetermined threshold range R1 centered on a target value tv. In the following description, reaching within the predetermined threshold range R1 is expressed as "reaching the target value".

In FIG. 21, each of the measurement values is an average value of the measurement values by the partial detection areas PAA1 and PAA2. As illustrated in FIG. 21, a first measurement value v1 and a second measurement value v2 are values lower than the predetermined threshold range R1. A third measurement value v3 is a value higher than the predetermined threshold range R1. A fourth measurement value v4 is a value lower than the predetermined threshold range R1. The first to the fourth measurement values v1 to v4 are values all outside the predetermined threshold range R1.

Unlike these measurement values, a fifth measurement value v5 is a value within the predetermined threshold range R1. Since the measurement value has reached the target value, the light quantities set by the light quantity controller 13 at that time are stored as initial set values.

In FIG. 21, when the change in the light quantity turns from upward to downward (or from downward to upward), the increase (decrease) is preferably made smaller than the previous increase (or previous decrease) by a predetermined value. For example, the increase (decrease) only needs to be approximately half the previous increase (or previous decrease). If the increase (decrease) is set to the same amount as the previous increase (or previous decrease), the light quantity may be possibly adjusted to be above the upper limit value or below the lower limit value of the predetermined threshold range R1. In contrast, if the increase (decrease) is approximately half the previous increase (or decrease) as described above, such a possibility is eliminated.

Referring back to FIG. 19, the biometric information detector 14 detects the information on the living body using the sensor 10. The light quantity storage 134 has stored therein the light quantities set by the light quantity controller 13 when the average value between the measurement value by the partial detection area PAA1 and the measurement value by the partial detection area PAA2 of the sensor 10 has reached the target value. That is, the light quantity storage 134 has stored therein the light quantities for biometric information detection. The biometric information detector 14 detects the information on the living body based on the light from the first and the second light sources 61 and 62 that emit the light at the light quantities for biometric information detection stored in the light quantity storage 134. By referring to the average value of the measurement values as described above, the initial values of the light quantities of the first and the second light sources 61 and 62 can be properly set. As a result, $SpO_2$ can be properly measured.

Figure 22:
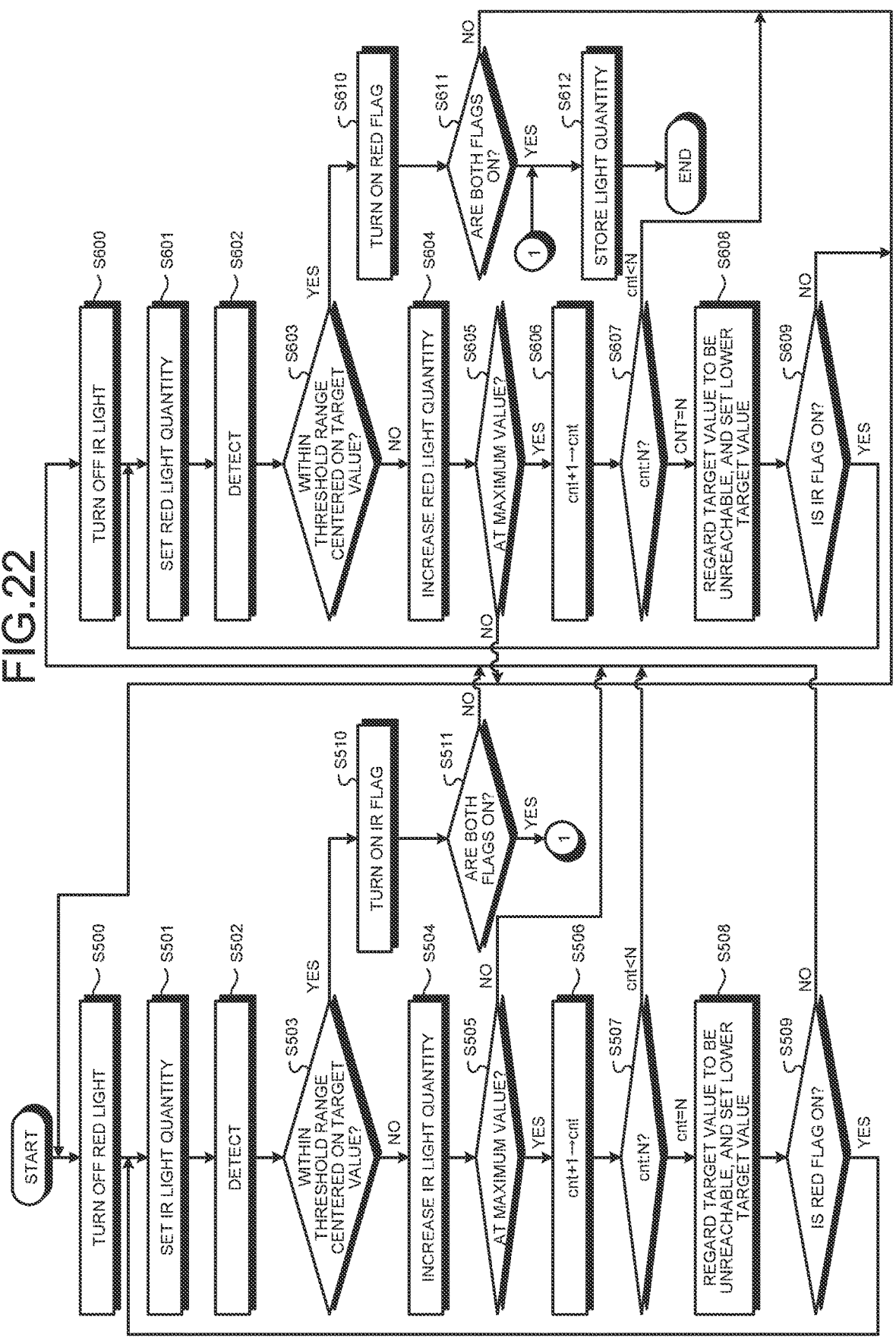
FIG. 22 is a flowchart illustrating an exemplary process for setting initial values of the light quantities.

FIG. 22 is a flowchart illustrating an exemplary process for setting the initial values of the light quantities. Each processing illustrated in FIG. 22 is mainly performed by the signal processor 44 of the detector 40.

In FIG. 22, first, the light quantity of the second light sources 62 is set to zero (Step S500). That is, the Red light is set to be off. Then, the first light quantity controller 131 sets the light quantity of the first light sources 61 (Step S501). The IR light is emitted from the first light sources 61 at the set light quantity and is measured, and the average value is detected (Step S502).

Then, determination is made as to whether the detected average value is within the threshold range centered on the target value (Step S503). If the result of the determination at Step S503 is that the detected average value is not within the threshold range (No at Step S503), the light quantity of the first light sources 61 is controlled to increase (Step S504). Then, determination is made as to whether the light quantity is at the maximum value (Step S505). The light quantity of the first light sources 61 is at the maximum value when the duty cycle mentioned above is 100%.

If the result of the determination at Step S505 is that the light quantity is at the maximum value (Yes at Step S505), a counter value cnt for error determination is incremented by one (Step S506), and determination is made as to whether the counter value cnt is a predetermined value N (Step S507). If, even after reaching the maximum value, the light quantity fails to reach the target value for N consecutive times, an error is determined to have occurred. The error is determined to have occurred, for example, if a living body such as the finger is not present.

If the result of the determination at Step S507 is that the counter value cnt is the predetermined value N (cnt=N), the target value is regarded to be unreachable, and a lower target value is set as a new target value (Step S508). The value N is a natural number. The value N is "3", for example.

Then, determination is made as to whether a Red flag is on (Step S509), wherein the Red flag is a flag indicating that the processing on the Red light has ended. If the result of the determination at Step S509 is that the Red flag is on (Yes at Step S509), the process returns to Step S501.

If the result of the determination at Step S505 is that the light quantity is not at the maximum value (No at Step S505), the process moves to Step S600. If the result of the determination at Step S507 is that the counter value cnt is not the predetermined value N (cnt<N), the process moves to Step S600. If the result of the determination at Step S509 is that the Red flag is not on (No at Step S509), the process moves to Step S600.

At Step S600, the light quantity of the first light sources 61 is set to zero (Step S600). That is, the Ir light is set to be off. Then, the second light quantity controller 132 sets the light quantity of the second light sources 62 (Step S601). The Red light is emitted from the second light sources 62 at the set light quantity and is measured, and the average value is detected (Step S602).

Then, determination is made as to whether the detected average value is within the threshold range centered on the target value (Step S603). If the result of the determination at Step S603 is that the detected average value is not within the threshold range (No at Step S603), the light quantity of the second light sources 62 is controlled to increase (Step S604). Then, determination is made as to whether the light quantity is at the maximum value (Step S605). The light quantity of the second light sources 62 is at the maximum value when the duty cycle mentioned above is 100%.

If the result of the determination at Step S605 is that the light quantity is at the maximum value (Yes at Step S605), the counter value cnt for error determination is incremented by one (Step S606), and determination is made as to whether the counter value cnt is the predetermined value N (Step S607). If, even after reaching the maximum value, the light quantity fails to reach the target value for N consecutive times, an error is determined to have occurred. The error is determined to have occurred, for example, if a living body such as the finger is not present.

If the result of the determination at Step S607 is that the counter value cnt is the predetermined value N (cnt=N), the target value is regarded to be unreachable, and a lower target value is set as the new target value (Step S608). The value N is a natural number. The value N is "3", for example.

Then, determination is made as to whether an IR flag is on (Step S609), wherein the IR flag is a flag indicating that the processing on the IR light has ended. If the result of the determination at Step S609 is that the IR flag is on (Yes at Step S609), the process returns to Step S601.

If the result of the determination at Step S605 is that the light quantity is not at the maximum value (No at Step S605), the process moves to Step S500. If the result of the determination at Step S607 is that the counter value cnt is not the predetermined value N (cnt<N), the process moves to Step S500. If the result of the determination at Step S609 is that the IR flag is not on (No at Step S609), the process moves to Step S500.

If the result of the determination at Step S503 is that the detected average value is within the threshold range (Yes at Step S503), the IR flag is turned on (Step S510). Here, determination is made as to whether the IR flag and the Red flag are both on (Step S511). If the result of the determination at Step S511 is that either of the flags is not on (No at Step S511), the process moves to Step S600.

If the result of the determination at Step S603 is that the detected average value is within the threshold range (Yes at Step S603), the red flag is turned on (Step S610). Here, determination is made as to whether the IR flag and the Red flag are both on (Step S611). If the result of the determination at Step S611 is that either of the flags is not on (No at Step S611), the process moves to Step S500.

If the result of the determination at Step S511 is that both the flags are on (Yes at Step S511), or if the result of the determination at Step S611 is that both the flags are on (Yes at Step S611), the measurement ends. The light quantity at that time is stored in the light quantity storage 134 as the light quantity to be used when detecting the biometric information (Step S612), and the process ends.

In the process described with reference to FIG. 22, if neither the IR flag nor the Red flag is on (No at Step S509, and No at Step S609), the processes from Step S501 to Step S509 and the processes from Step S601 to Step S609 are alternately performed. That is, the measurement of the IR light quantity and the measurement of the Red light quantity are alternately performed. To alternately measure the light quantities, the Red light is set to be off when the IR light quantity is measured, and the IR light is set to be off when the Red light quantity is measured.

As described above, the highly accurate data can be acquired by referring to the average value of the measurement values of a plurality of sensors and initializing the light quantity so that the measurement values fall within the same range as that of the target value.

Second Example of Initialization

Figure 23:
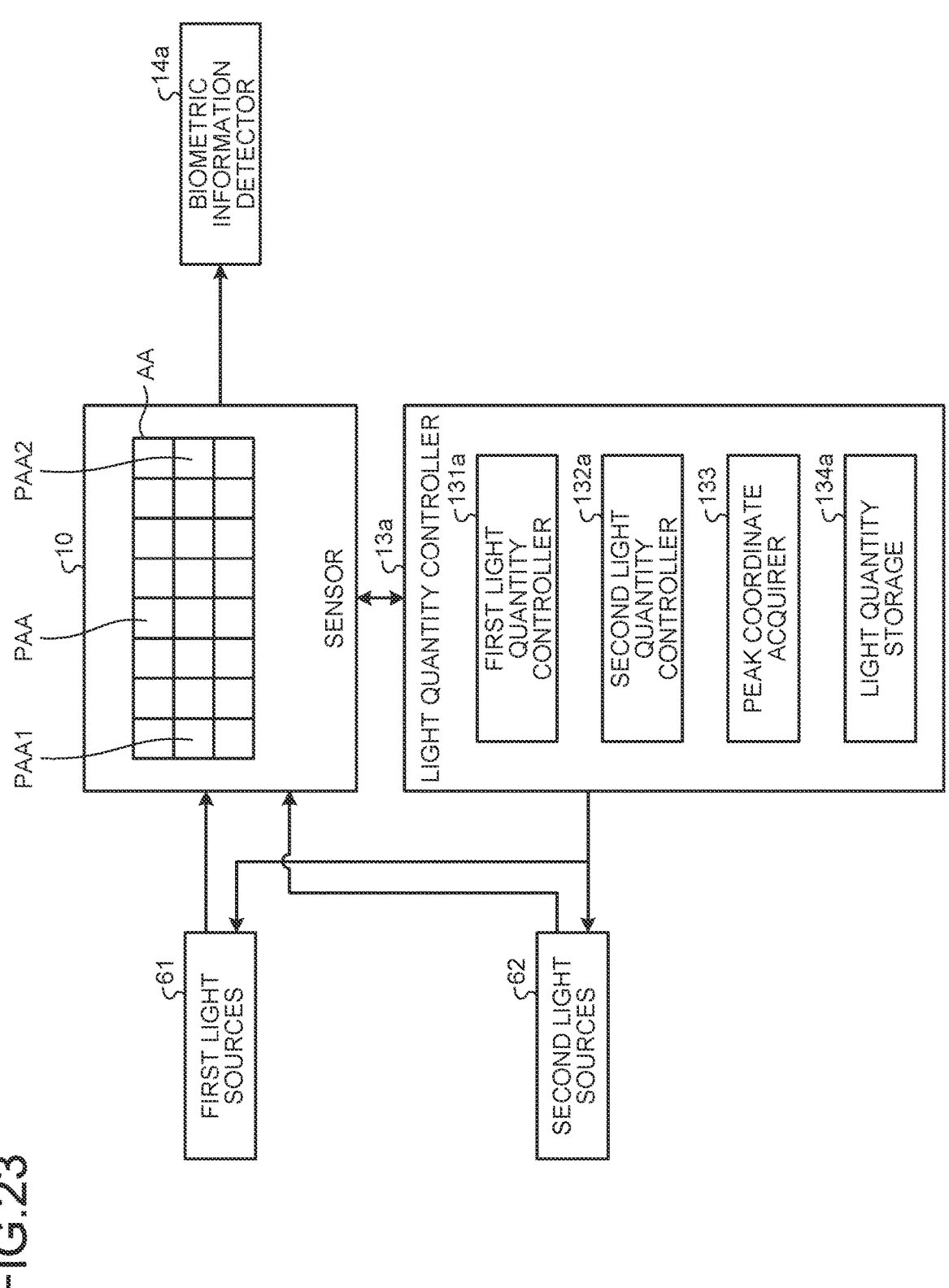
FIG. 23 is a diagram explaining a second configuration example for initializing the light quantities of the light sources.

The following describes another example of the initialization of the light quantities of the first and the second light sources 61 and 62. FIG. 23 is a diagram explaining a second configuration example for initializing the light quantities of the light sources.

In the first configuration example described above, the light quantity is initialized so that the average value of the measurement values of the sensors reaches the target value. In contrast, in the second configuration example to be described below, the initialization is performed as described below. That is, the light quantity of the first light sources 61 is set so that the measurement value of a sensor in any temporarily determined coordinate position reaches the target value. Then, referring to an optical sensor in a peak coordinate position where the measurement value is highest, the light quantity of the second light sources 62 is set so that the measurement value in the peak coordinate position reaches the target value.

Referring to FIG. 23, the second configuration for performing the initialization includes a light quantity controller (light quantity control circuit) 13a instead of the light quantity controller 13 of the first configuration described with reference to FIG. 19. The light quantity controller 13a includes a first light quantity controller (first light quantity control circuit) 131a, a second light quantity controller (second light quantity control circuit) 132a, a peak coordinate acquirer (peal coordinate acquisition circuit) 133, and a light quantity storage (light quantity storage circuit) 134a. In this example, the first light sources 61 are light sources that emit the IR light. In this example, the second light sources 62 are light sources that emit the red light.

The first light quantity controller 131a sets the light quantity of the first light sources 61. The first light quantity controller 131a changes the light quantity of the first light sources 61. The first light quantity controller 131a increases the IR light quantity until the measurement value of an optical sensor in a predetermined coordinate position among the optical sensors reaches the target value.

The peak coordinate acquirer 133 acquires the peak coordinate position where the measurement value is highest among those of the optical sensors when the measurement value in the predetermined coordinate position mentioned above has reached the target value. The peak coordinate acquirer 133 acquires the position where the amplitude of the pulse wave is largest as the peak coordinate position. The process to detect the peak coordinate position will be described later.

The second light quantity controller 132a sets the light quantity of the second light sources 62. The second light quantity controller 132a changes the light quantity of the second light sources 62. The second light quantity controller 132a increases the Red light quantity until the measurement value in the peak coordinate position acquired by the peak coordinate acquirer 133 reaches the target value.

When the measurement value of the optical sensor in the peak coordinate position has reached the target value, the light quantity storage 134a stores therein the light quantity set by the first light quantity controller 131a and the light quantity set by the second light quantity controller 132a as the light quantities for biometric information detection. The light intensities stored by the light quantity storage 134a serve as light quantities that are initially set when a biometric information detector 14a detects the biometric information. That is, the light quantities for biometric information detection are stored in the light quantity storage 134a.

The biometric information detector 14a detects the biometric information based on the light from the first and the second light sources 61 and 62 that emit the light at the light quantities for biometric information detection stored in the light quantity storage 134a.

Figure 24:
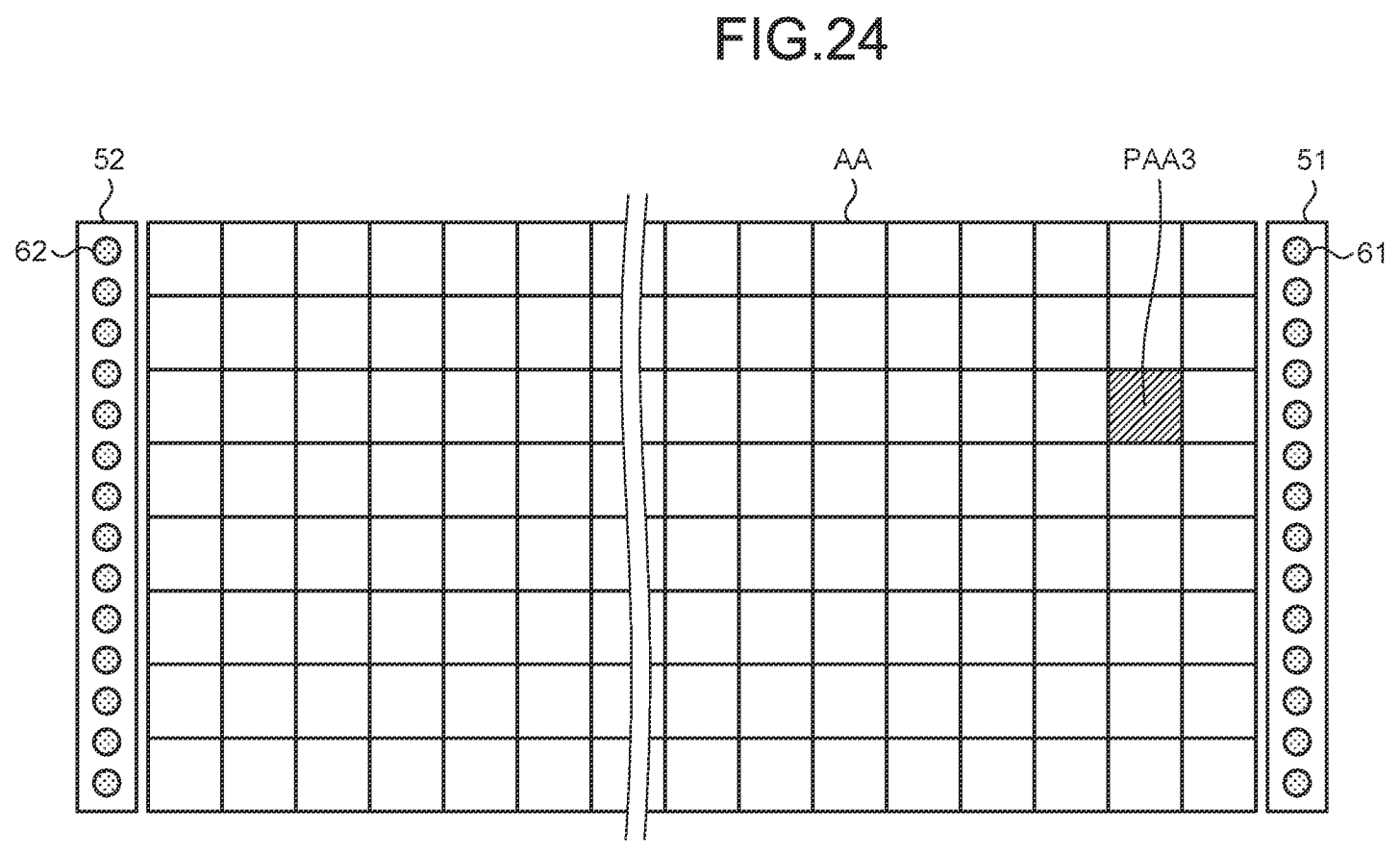

FIGS. 24 to 27 are plan views and charts explaining the initialization performed by the configuration illustrated in FIG. 23. In FIG. 24, a partial detection area PAA3 in the detection area AA is assumed here to be an area for the sensor in any temporarily determined coordinate position. Using the sensor in the coordinate position of the partial detection area PAA3 as a measurement target, the first light quantity controller 131a sets the light quantity of the first light sources 61 (that is, the IR light sources) so that the measurement value of the measurement target reaches the target value.

Figure 25:
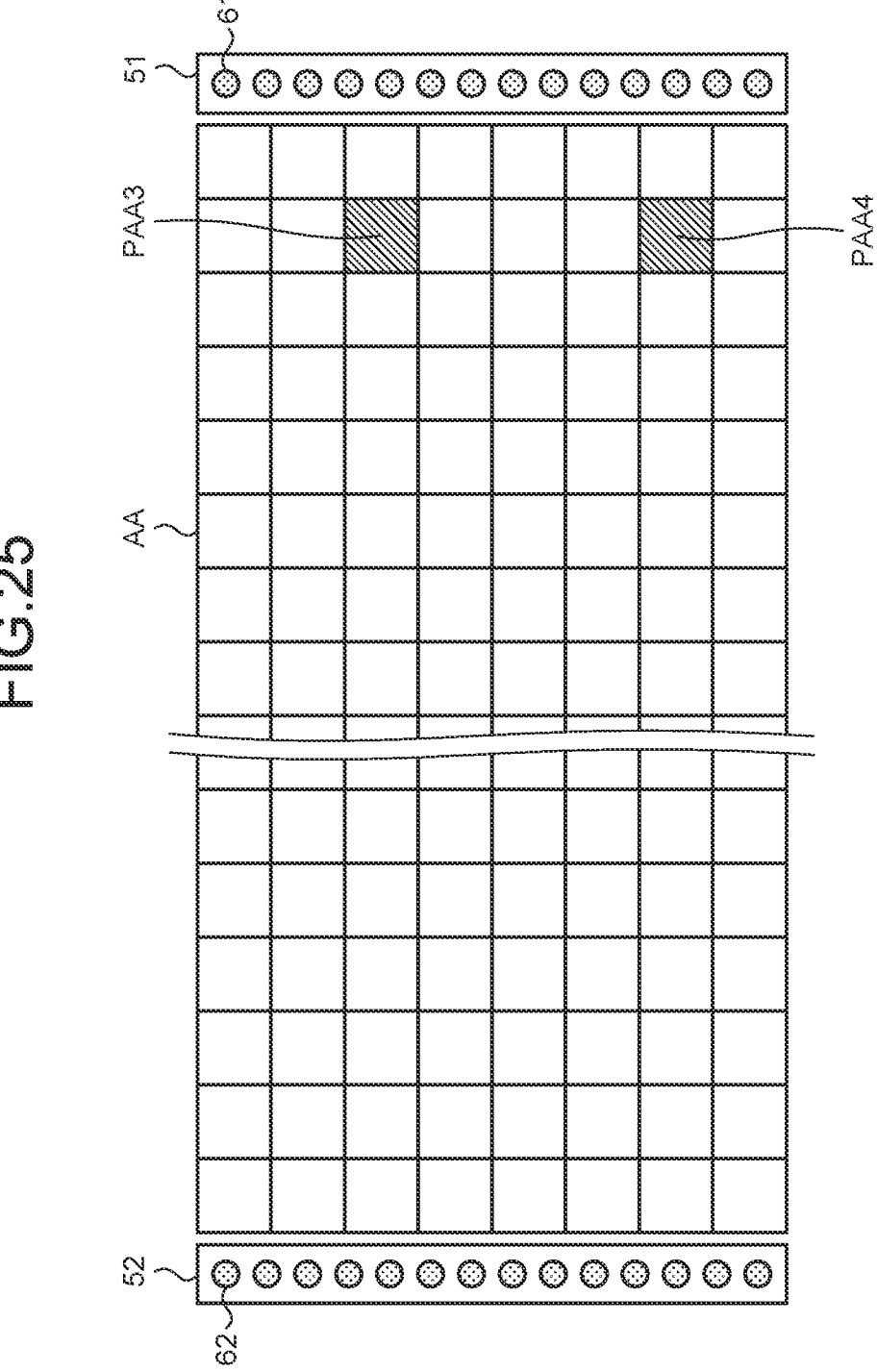
FIG. 25 is a plan view explaining the initialization performed by the configuration illustrated in FIG. 23.

The setting of the light quantity by the first light quantity controller 131a increases the measurement value of the sensor in the coordinate position of the partial detection area PAA3 as illustrated in FIG. 25. When the measurement value has reached the target value tv as illustrated in FIG. 26, the peak coordinate acquirer 133 acquires the peak coordinate position where the measurement value is highest.

Figure 26:
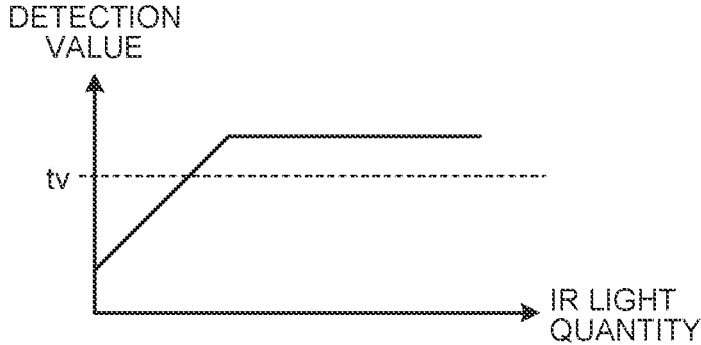
FIG. 26 is a chart explaining the initialization performed by the configuration illustrated in FIG. 23.

This example assumes that a partial detection area PAA4 illustrated in FIG. 26 is acquired as the peak coordinate position as a result of the setting of the light quantity of the first light sources 61 by the first light quantity controller 131a. The second light quantity controller 132a measures the partial detection area PAA4 in the peak coordinate position while setting the light quantity of the second light sources 62 (that is, the Red light sources). That is, the second light quantity controller 132a increases the light quantity of the second light sources 62 until the measurement value in the peak coordinate position reaches the target value. At this time, the Ir light of the first light sources 61 is set to be off.

Figure 27:
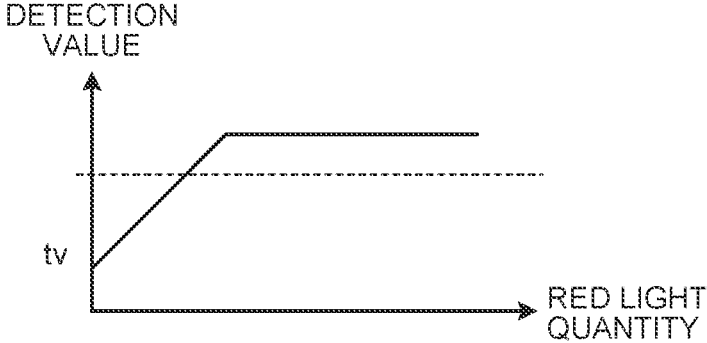
FIG. 27 is a chart explaining the initialization performed by the configuration illustrated in FIG. 23.

The setting of the light quantity by the second light quantity controller 132a increases the measurement value of the sensor in the coordinate position of the partial detection area PAA4 as illustrated in FIG. 27. When the measurement value reaches the target value tv as illustrated in FIG. 27, the biometric information detector 14a sets the light quantity of the first light sources 61 to the IR light quantity of the first light quantity controller 131a and the light quantity of the second light sources 62 to the Red light quantity of the second light quantity controller 132a, and detects the information on the living body.

As illustrated in FIG. 22, the IR light may be measured using the sensors on the entire surface of the detection area AA without determining the particular partial detection area PAA3.

Figure 28:
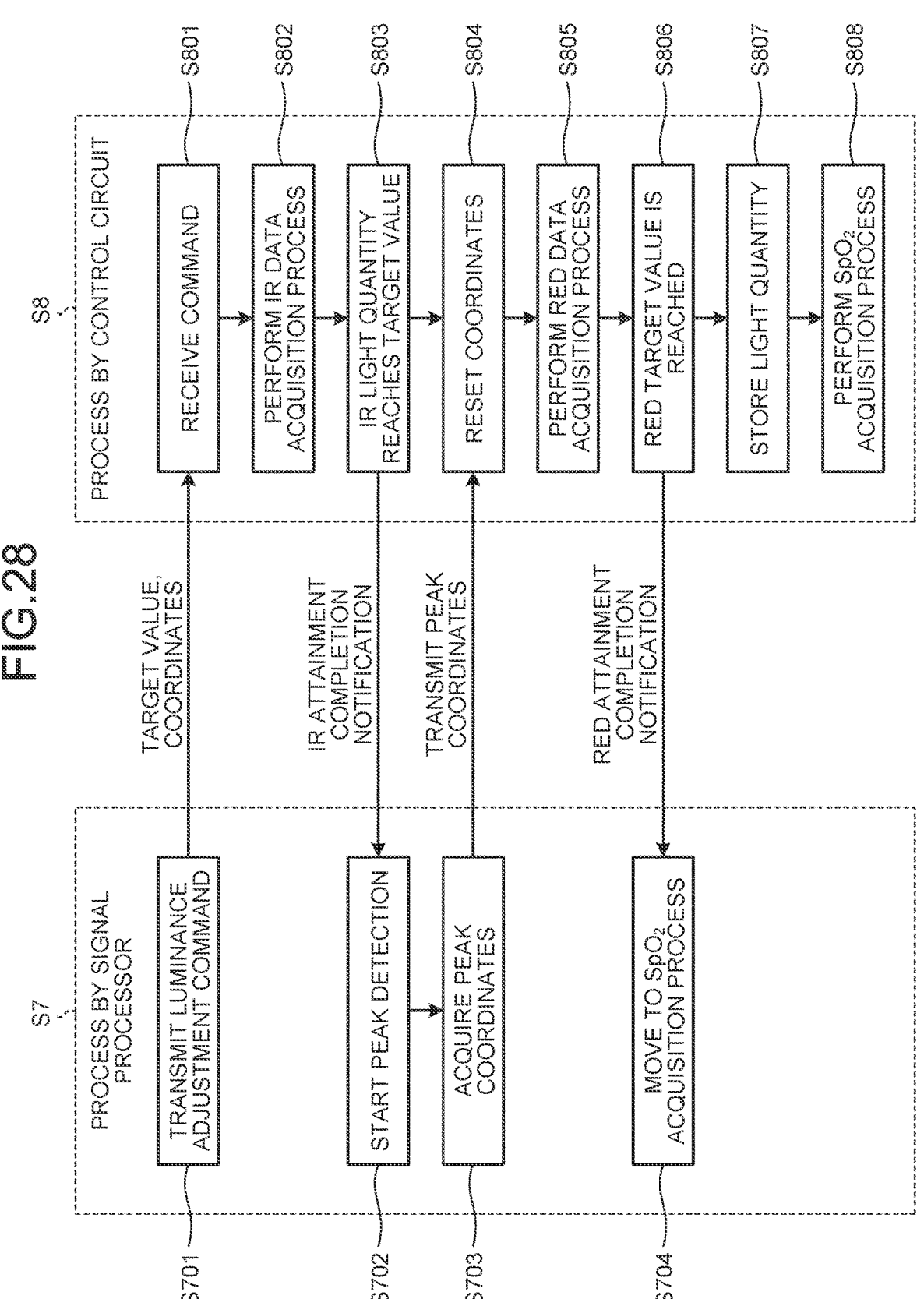
FIG. 28 is a flowchart illustrating an exemplary process of the second configuration in FIG. 23.

The process of the second configuration in FIG. 23 described with reference to FIGS. 24 to 27 will be further described with reference to FIGS. 28 to 31. FIG. 28 is a flowchart illustrating an exemplary process of the second configuration in FIG. 23. The process illustrated in FIG. 28 includes a process S7 performed by the signal processor 44 and a process S8 performed by the control circuit 122.

In FIG. 28, first, the signal processor 44 transmits a luminance adjustment command to adjust the luminance (Step S701). The luminance adjustment command includes a target value and coordinates.

After the control circuit 122 receives the luminance adjustment command (Step S801), the control circuit 122 performs an IR data acquisition process to acquire the measurement value of the IR light quantity (Step S802). The IR data acquisition process will be described later. After the IR light quantity reaches the target value (Step S803), an IR attainment completion notification is output to indicate that fact.

After the signal processor 44 receives the IR attainment completion notification, the signal processor 44 starts a process to acquire peak coordinates (Step S702). The process to acquire the peak coordinates will be described later. After the peak coordinates are acquired by the process of the signal processor 44 (Step S703), the signal processor 44 transmits the peak coordinates.

After the control circuit 122 receives the peak coordinates, the control circuit 122 resets the peak coordinates as the coordinates of the measurement target (Step S804). Then, the control circuit 122 performs a Red data acquisition process to acquire the measurement value of the Red light quantity (Step S805). The red data acquisition process will be described later. After the measurement value of the red light quantity reaches the target value (Step S806), a Red attainment completion notification is output to indicate that fact.

After the signal processor 44 receives the Red attainment completion notification, the control circuit 122 performs the process to detect the information on the living body (Step S704). In this example, an SpO₂ acquisition process is performed to measure SpO₂.

The control circuit 122 sets the light quantity of the first light sources 61 to the IR light quantity of the first light quantity controller 131a and the light quantity of the second light sources 62 to the red light quantity of the second light quantity controller 132a, and stores the setting results in the light quantity storage 134a (Step S807). The process described above completes the initialization of the light quantities for measuring SpO₂, and the control circuit 122 performs the SpO₂ acquisition process to measure SpO₂ (Step S808).

Figure 29A:
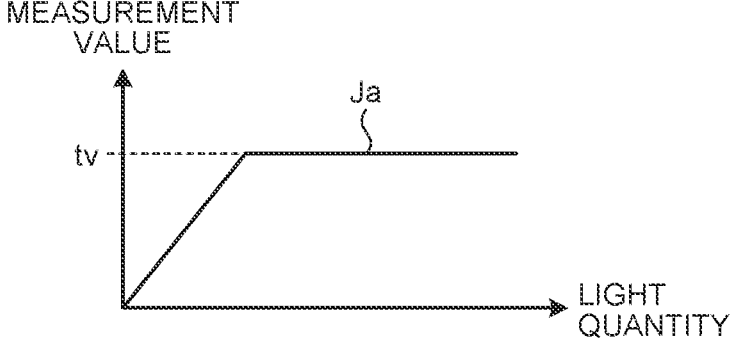
FIG. 29A is a chart illustrating a state where an infrared (IR) light quantity reaches a target value.

FIG. 29A is a graph illustrating a state where the IR light quantity reaches the target value. FIG. 29A is a waveform chart explaining an example of the processing at Step S803 in FIG. 28. As illustrated in FIG. 29A, increasing the IR light quantity level increases the measurement value as illustrated by a voltage value indicated by a solid line Ja. The measurement value increases and reaches the target value tv. Since the measurement value has reached the target value tv, the IR light quantity level is maintained, and the measurement value of the red light quantity is acquired by the processes at Steps S805 and S806 in FIG. 28.

Figure 29B:
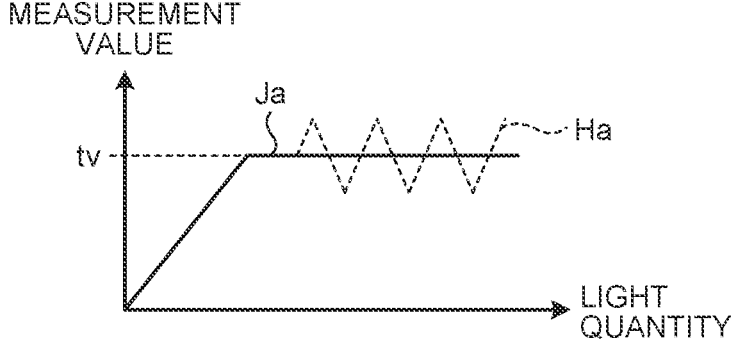
FIG. 29B is a chart illustrating a state where a Red light quantity reaches the target value.
Figure 29C:
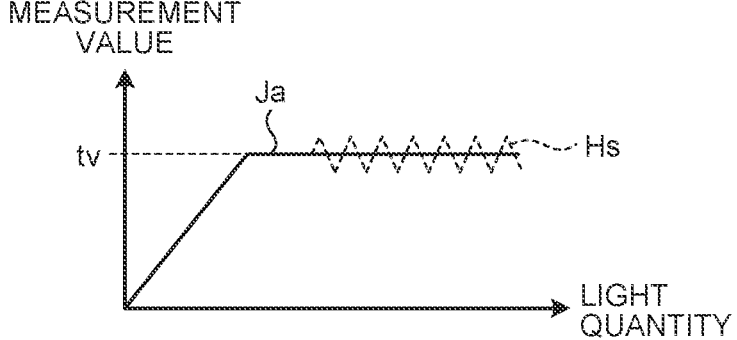
FIG. 29C is a chart illustrating another state where the Red light quantity reaches the target value.

FIGS. 29B and 29C are charts illustrating states where the red light quantity reaches the target value. FIGS. 29B and 29C are waveform charts explaining examples of the processes at Steps S805 and S806. A pulse wave indicated by a dashed line Ha is added to a DC voltage indicated by the solid line Ja in FIG. 29B. The pulse wave fluctuates in voltage value over time. The peak coordinate acquirer 133 acquires, as the peak coordinate position, the position where the amplitude of the pulse wave is largest. The frequency of this pulse wave is, for example, from 0.5 Hz to 3 Hz. The measurement value of the red light quantity including the fluctuating pulse wave needs to reach the target value. In the case of FIG. 29C, a pulse wave having smaller amplitude indicated by a dashed line Hs is also added to the DC voltage indicated by the solid line Ja. Also in this case, the measurement value of the Red light quantity including the fluctuating pulse wave needs to reach the target value.

Figure 30:
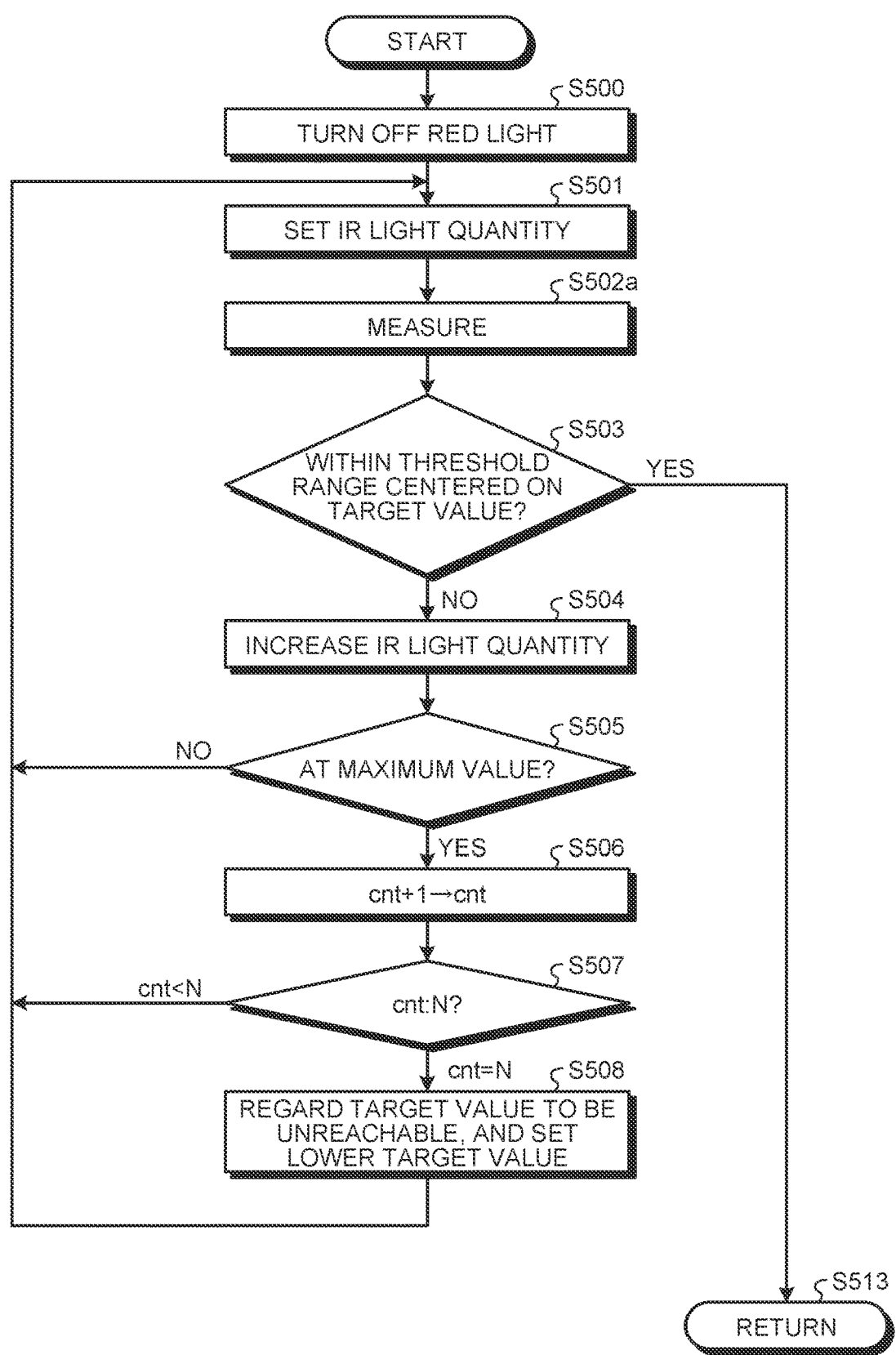
FIG. 30 is a flowchart illustrating an example of an IR data acquisition process in FIG. 28.

FIG. 30 is a flowchart illustrating an example of the IR data acquisition process (Step S802) in FIG. 28. In FIG. 30, first, the light quantity of the second light sources 62 is set to zero (Step S500). That is, the Red light is set to be off. Then, the first light quantity controller 131 sets the light quantity of the first light sources 61 (Step S501). The IR light is emitted from the first light sources 61 at the set light quantity and is measured (Step S502a).

Then, determination is made as to whether the measurement value is within the threshold range centered on the target value (Step S503). If the result of the determination at Step S503 is that the measured value is not within the threshold range (No at Step S503), the light quantity of the first light sources 61 is increased (Step S504). Then, determination is made as to whether the light quantity is at the maximum value (Step S505). The light quantity of the first light sources 61 is at the maximum value when the duty cycle mentioned above is 100%.

If the result of the determination at Step S505 is that the light quantity is at the maximum value (Yes at Step S505), the counter value cnt for error determination is incremented by one (Step S506), and determination is made as to whether the counter value cnt is the predetermined value N (Step S507).

If the result of the determination at Step S507 is that the counter value cnt is the predetermined value N (cnt=N), the target value is regarded to be unreachable, and a lower target value is set as the new target value (Step S508). Then, the process returns to Step S501. The value N is a natural number. The value N is "3", for example.

If the result of the determination at Step S505 is that the light quantity is not at the maximum value (No at Step S505), the process returns to Step S501.

If the result of the determination at Step S507 is that the counter value cnt is not the predetermined value N (cnt<N), the process returns to Step S501.

If the result of the determination at Step S503 is that the measured value is within the threshold range (Yes at Step S503), the measurement ends, and the process returns to the original process (Step S513).

Figure 31:
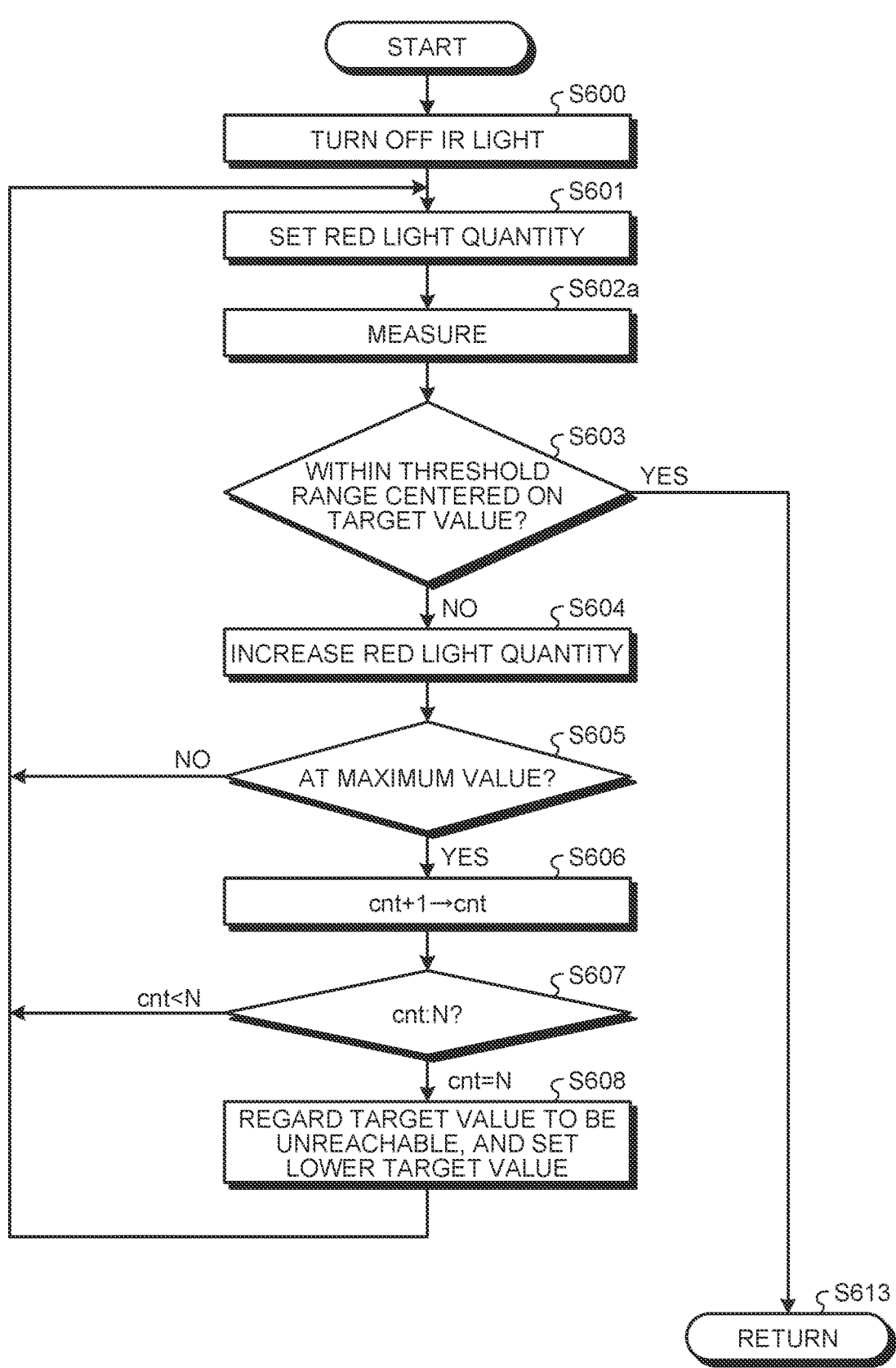
FIG. 31 is a flowchart illustrating an example of a red data acquisition process in FIG. 28.

FIG. 31 is a flowchart illustrating an example of the red data acquisition process (Step S805) in FIG. 28. In FIG. 31, first, the light quantity of the first light sources 61 is set to zero (Step S600). That is, the Ir light is set to be off. Then, the second light quantity controller 132 sets the light quantity of the second light sources 62 (Step S601). The Red light is emitted from the second light sources 62 at the set light quantity and is measured (Step S602a).

Then, determination is made as to whether the measurement value is within the threshold range centered on the target value (Step S603). If the result of the determination at Step S603 is that the measured value is not within the threshold range (No at Step S603), the light quantity of the second light sources 62 is increased (Step S604). Then, determination is made as to whether the light quantity is at the maximum value (Step S605). The light quantity of the second light sources 62 is at the maximum value when the duty cycle mentioned above is 100%.

If the result of the determination at Step S605 is that light quantity is at the maximum value (Yes at Step S605), the counter value cnt for error determination is incremented by one (Step S606), and determination is made as to whether the counter value cnt is the predetermined value N (Step S607).

If the result of the determination at Step S607 is that the counter value cnt is the predetermined value N (cnt=N), the target value is regarded to be unreachable, and a lower target value is set as the new target value (Step S608). Then, the process returns to Step S601. The value N is a natural number. The value N is "3", for example.

If the result of the determination at Step S605 is that the light quantity is not at the maximum value (No at Step S605), the process returns to Step S601.

If the result of the determination at Step S607 is that the counter value cnt is not the predetermined value N (cnt<N), the process returns to Step S601.

If the result of the determination at Step S603 is that the measured value is within the threshold range (Yes at Step S603), the measurement ends, and the process returns to the original process (Step S613).

As described above, the highly accurate data can be acquired by referring to the measurement value of the sensor in the position where the measurement value is the maximum value and initializing the light quantity so that the measurement value falls within the same range as that of the target value. The transmittance of the living body is higher for the IR light than for the Red light. Therefore, the target value is likely to be reached earlier for the IR light than for the Red light. Thus, by employing the sequence in which setting the IR light quantity is performed first and then setting the Red light quantity is performed as described above, the initialization can be performed more efficiently than being performed in the reverse sequence.

Process to Detect Peak Coordinate Position

Figure 32:
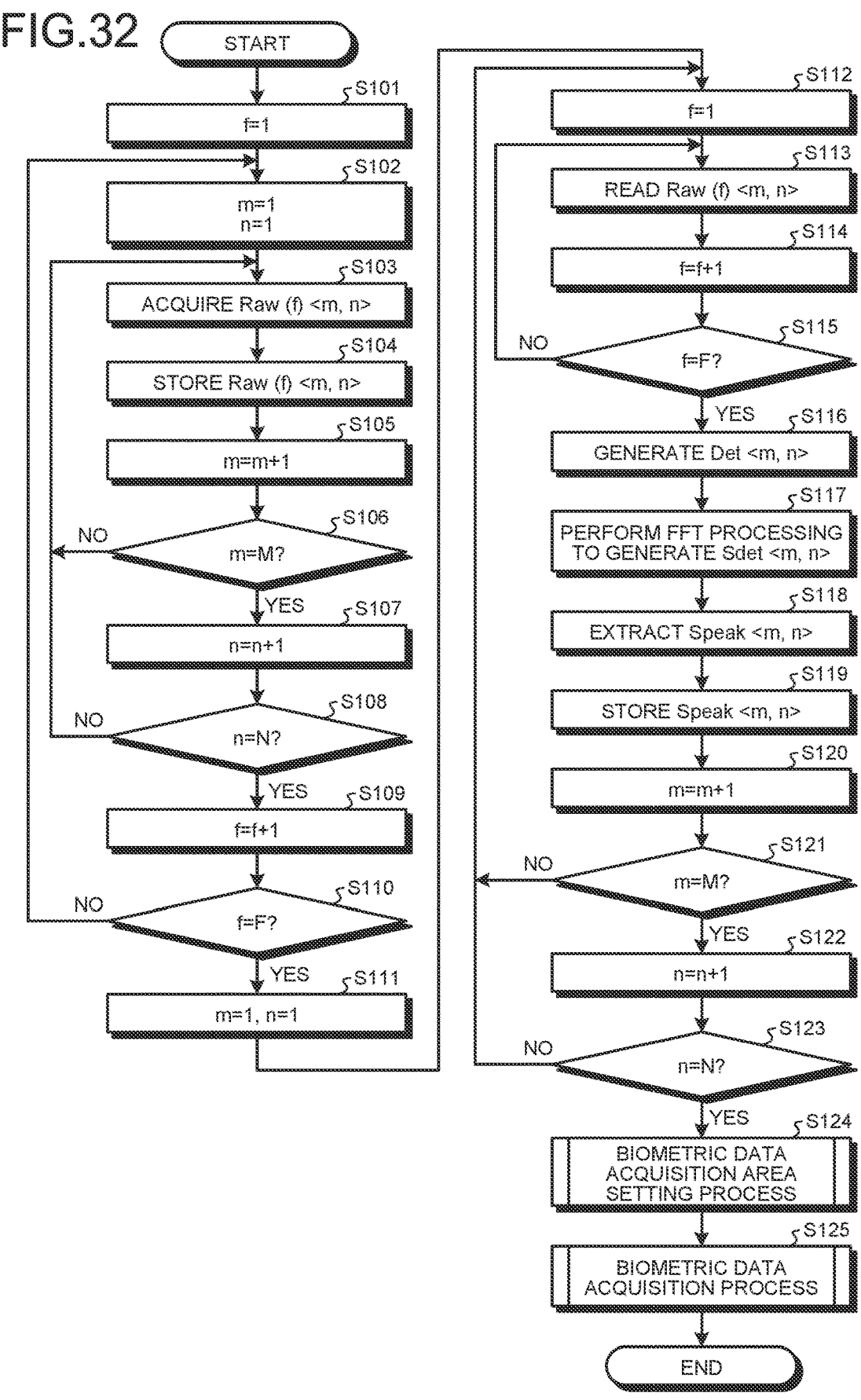
FIG. 32 is a flowchart illustrating an exemplary detection process to detect a peak coordinate position.

The following describes the process to detect the peak coordinate position. FIG. 32 is a flowchart illustrating an exemplary detection process to detect the peak coordinate position. Each processing illustrated in FIG. 32 is mainly performed by the signal processor 44 of the detector 40.

In the following description, X<m, n> denotes a variable in the partial detection area PAA in the m-th column of the n-th row. The variable X<m, n> includes coordinate information on the partial detection area PAA from which the variable X<m, n> has been acquired. X(f)<m, n> denotes the variable X<m, n> in the f-th frame.

In the detection process illustrated in FIG. 32, the signal processor 44 first acquires detection values Raw(f)<m, n> for a plurality of frames in each of the partial detection areas PAA in the detection area AA. The number of frames F for which the detection values Raw(f)<m, n> are to be acquired is set to the number of times (for example, approximately 10 times) by which the peak of the pulse wave can be acquired. The number of frames F is stored in the storage 46, for example.

In processes from Step S102 to Step S110 of the detection process illustrated in FIG. 32, the control circuit 122 continuously turns on either the first light sources 61 or the second light sources 62, for example, during the periods t(1), t(2), t(3), and t(4) illustrated in FIG. 10. Each of the detection values Raw(f)<m, n> is temporarily stored in the storage 46, for example. FIG. 33 is a chart illustrating the detection values for the F frames in each of the partial detection areas in the detection area that are temporarily stored in the storage.

The signal processor 44 sets an initial frame f to 1 (f=1) (Step S101). The signal processor 44 sets m=1 and n=1 (Step S102), acquires the detection value Raw(f)<m, n> (Step S103), and temporarily stores the acquired detection value Raw(f)<m, n> in the storage 46 (Step S104).

The signal processor 44 then sets m=m+1 (Step S105), and determines whether m is M (m=M) (Step S106). If m is smaller than M (m<M) (No at Step S106), the process returns to the processing at Step S103.

If m reaches M (m=M) (Yes at Step S106), the signal processor 44 then sets n=n+1 (Step S107), and determines whether n is N (n=N) (Step S108). If n is smaller than N (n<N) (No at Step S108), the process returns to the processing at Step S103.

If n reaches N (n=N) (Yes at Step S108), the signal processor 44 then sets f=f+1 (Step S109), and determines whether f is F (f=F) (Step S110). If f is smaller than F (f<F) (No at Step S110), the process returns to the processing at Step S102.

By repeating the above-described processes from Step S102 to Step S110 F times, the detection values Raw(f)<m, n> for the F frames in each of the partial detection areas PAA in the detection area AA illustrated in FIG. 33 are temporarily stored in the storage 46.

If f reaches F (f=F) (Yes at Step S110), the signal processor 44 then sets m=1 and n=1 (Step S111), sets the initial frame f to 1 (f=1) (Step S112), and reads the detection value Raw(f)<m, n> from the storage 46 (Step S113). Further, the signal processor 44 sets f=f+1 (Step S114), and determines whether f is F (f=F) (Step S115). If f is smaller than F (f<F) (No at Step S115), the process returns to the processing at Step S113.

By performing the processes from Step S113 to Step S115 described above, the detection values Raw(f)<m, n> for the F frames in the partial detection area PAA in the m-th column of the n-th row are read.

Figure 34A:
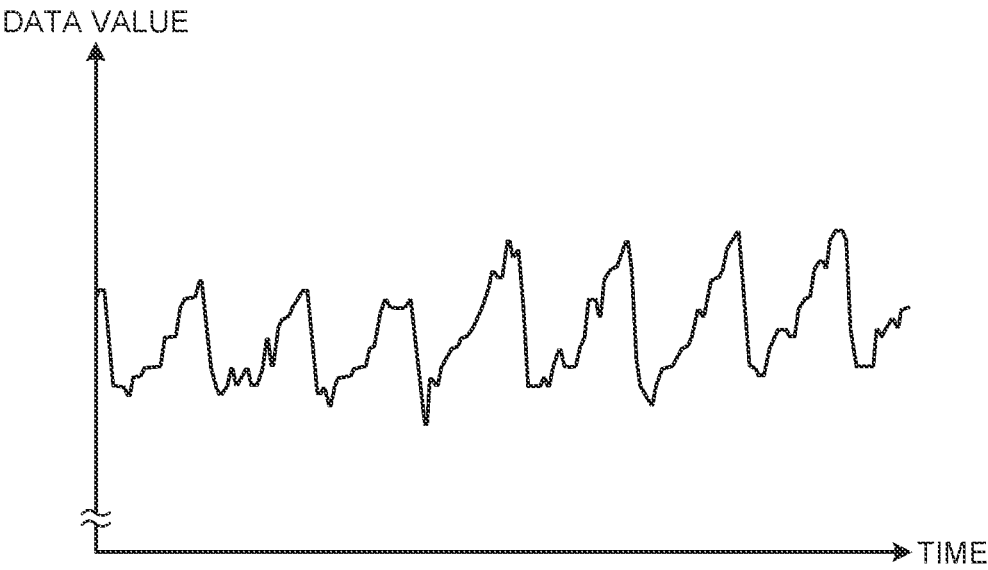
FIG. 34A is a graph illustrating a specific example of time-domain data in each of the partial detection areas.
Figure 34B:
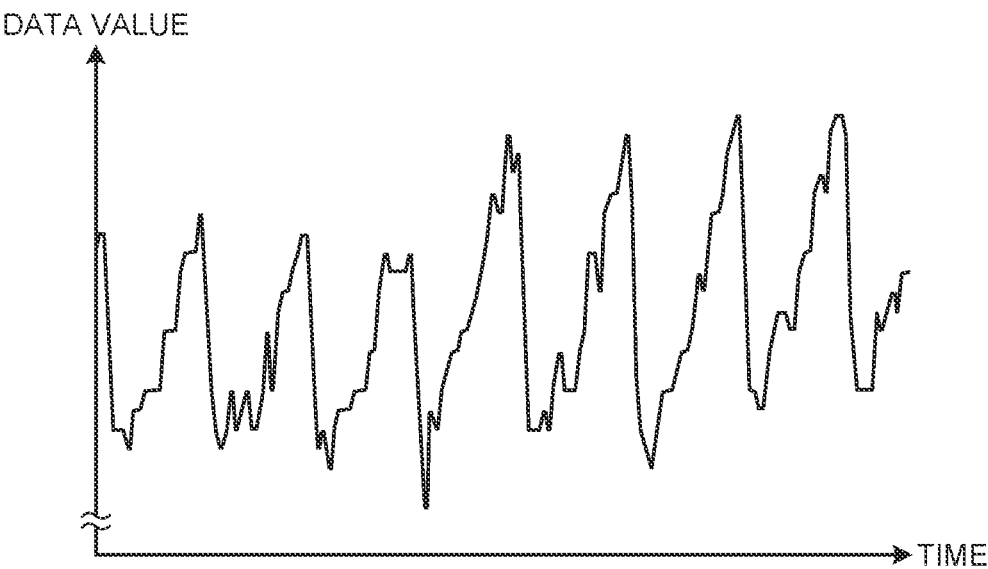
FIG. 34B is a graph illustrating another specific example of the time-domain data in each of the partial detection areas.

If f reaches F (f=F) (Yes at Step S115), the signal processor 44 generates time-domain data Det<m, n> in the partial detection area PAA in the m-th column of the n-th row, based on the detection values Raw(f)<m, n> for the F frames read from the storage 46 (Step S116). FIGS. 34A and 34B are diagrams illustrating specific examples of the time-domain data in each of the partial detection areas. FIG. 34A illustrates an example of the time-domain data in the partial detection area A illustrated in FIG. 15. FIG. 34B illustrates an example of the time-domain data in the partial detection area B illustrated in FIG. 15.

Figure 35A:
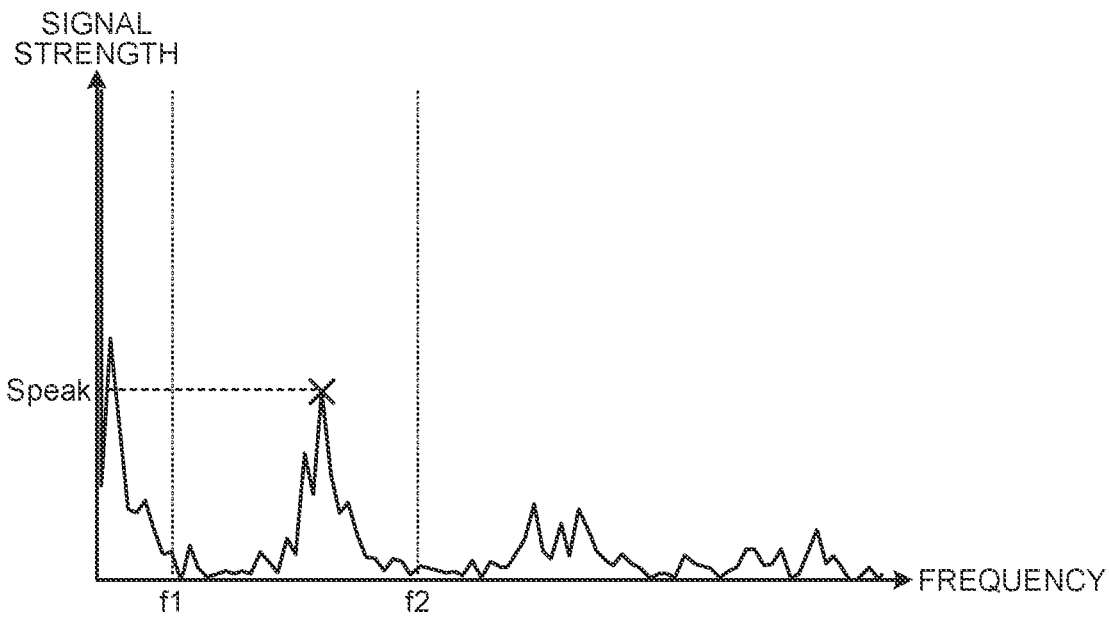
FIG. 35A is a graph illustrating a specific example of frequency-domain data in each of the partial detection areas.
Figure 35B:
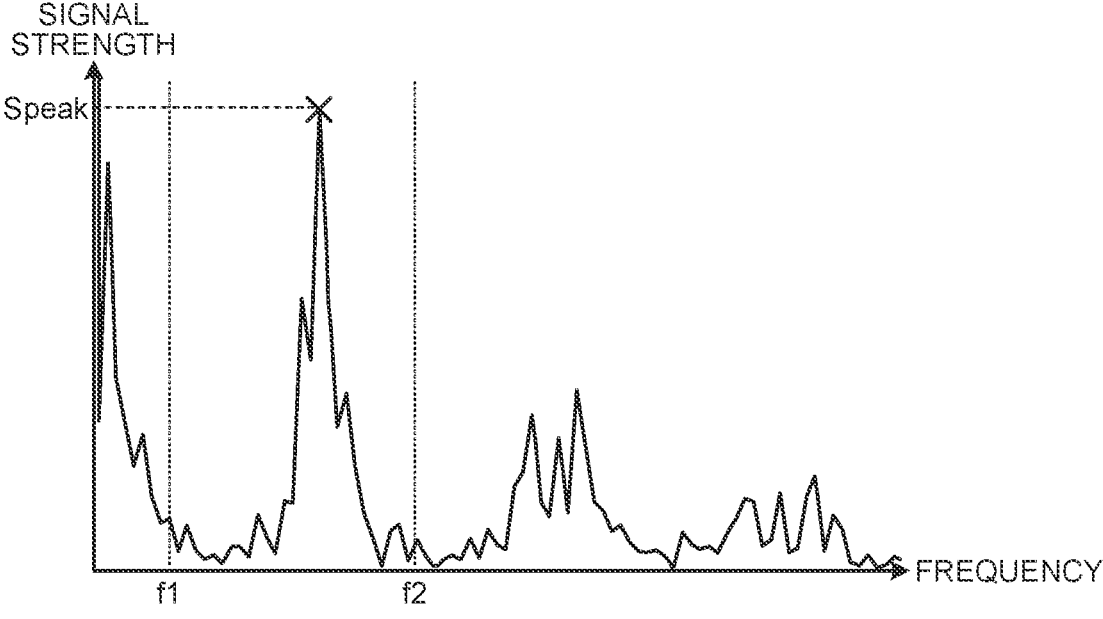
FIG. 35B is a graph illustrating another specific example of the frequency-domain data in each of the partial detection areas.

The signal processor 44 performs Fourier transform processing (in this case, fast Fourier transform (FFT) processing) on the generated time-domain data Det<m, n> in the partial detection area PAA in the m-th column of the n-th row to generate frequency-domain data Sdet<m, n> (Step S117). FIGS. 35A and 35B are diagrams illustrating specific examples of the frequency-domain data in each of the partial detection areas. FIG. 35A illustrates an example of the frequency-domain data in the partial detection area A illustrated in FIG. 15. FIG. 35B illustrates an example of the frequency-domain data in the partial detection area B illustrated in FIG. 15.

The signal processor 44 extracts a signal strength Speak<m, n> of a peak value of the frequency-domain data in a frequency domain from a first frequency f1 to a second frequency f2 illustrated in FIGS. 35A and 35B (Step S118). The first frequency f1 is set to 0.5 Hz (f1=0.5 Hz), for example, and the second frequency f2 is set to 3 Hz (f2=3 Hz), for example. The signal processor 44 temporarily stores the extracted signal strength Speak<m, n> of the peak value in the storage 46 as the signal strength in the partial detection area PAA in the m-th column of the n-th row (Step S119).

The signal processor 44 then sets m=m+1 (Step S120), and determines whether m is M (m=M) (Step S121). If m is smaller than M (m<M) (No at Step S121), the process returns to the processing at Step S112.

If m reaches M (m=M) (Yes at Step S121), the signal processor 44 then sets n=n+1 (Step S122), and determines whether n is N (n=N) (Step S123). If n is smaller than N (n<N) (No at Step S123), the process returns to the processing at Step S112.

By repeating the above-described processes from Step S112 to Step S123 M×N times, the signal strength Speak<m, n> in each of the partial detection areas PAA in the detection area AA is temporarily stored in the storage 46. If the above-described processes from Step S112 to Step S123 have been repeated M×N times (Yes at Step S123), the process moves to a processing at Step S124.

Based on the signal strength Speak<m, n> in each of the partial detection areas PAA in the detection area AA extracted by the processing described above, the signal processor 44 sets the biometric data acquisition area for acquiring the pulse wave data (Step S124).

Figure 36:
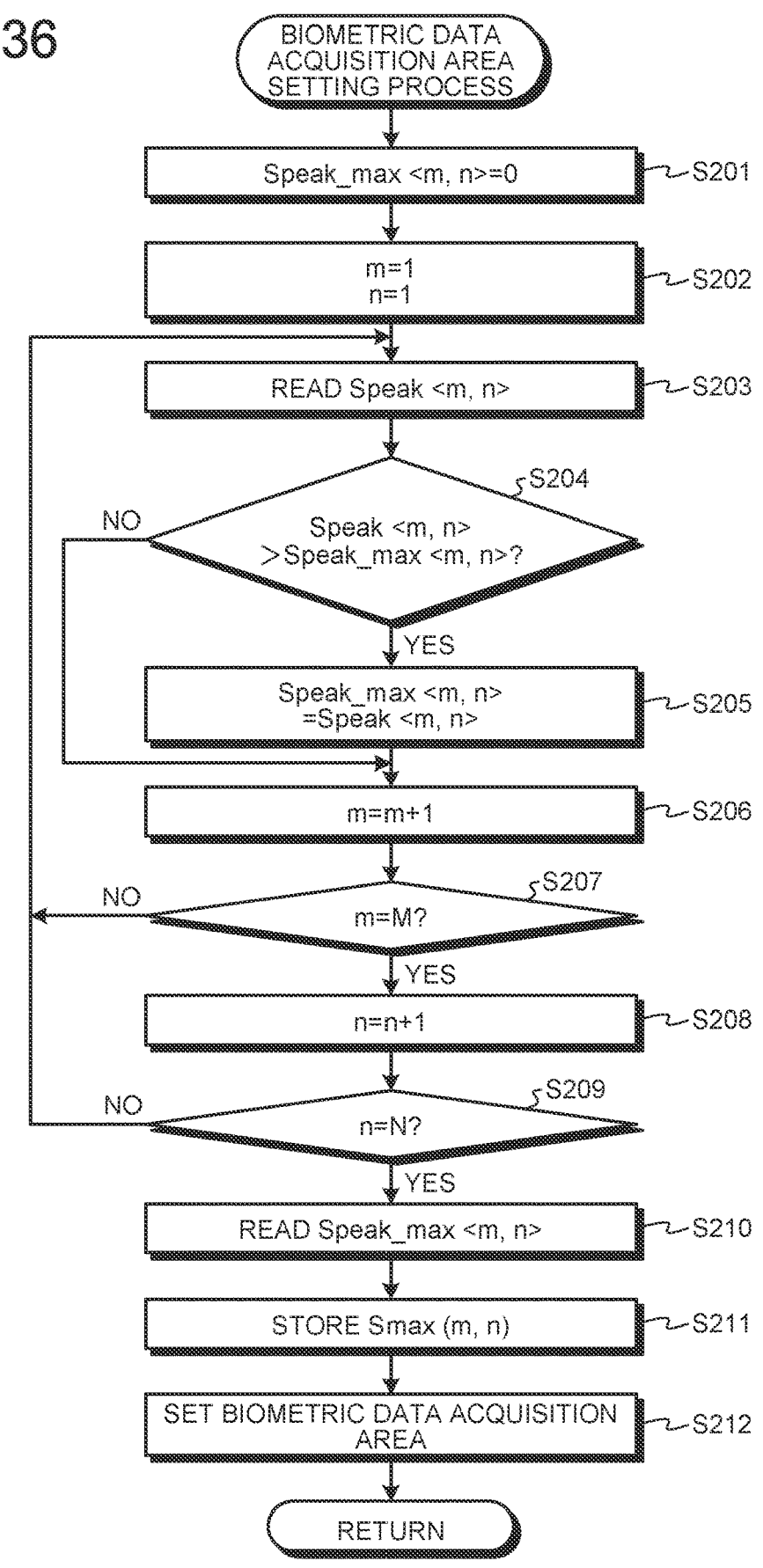
FIG. 36 is a flowchart illustrating an exemplary biometric data acquisition area setting process in the detection device.

FIG. 36 is a flowchart illustrating an exemplary biometric data acquisition area setting process in the detection device.

In the biometric data acquisition area setting process illustrated in FIG. 36, the signal processor 44 first performs comparison operations on the signal strengths Speak<m, n> in the respective partial detection areas PAA in the detection area AA and extracts coordinates of a position of the partial detection area PAA where the signal strength Speak<m, n> is maximal.

The signal processor 44 initializes a maximal signal strength Speak_max<m, n> to be 0 (Speak_max<m, n>=0) (Step S201). The signal processor 44 sets m=1 and n=1 (Step S202) and reads the signal strength Speak<m, n> (Step S203).

The signal processor 44 determines whether the read signal strength Speak<m, n> is higher than the maximal signal strength Speak_max<m, n> (Speak<m, n>>Speak_max<m, n>) (Step S204). If the signal strength Speak<m, n> is equal to or lower than the maximal signal strength Speak_max<m, n> (Speak<m, n>≤Speak_max<m, n>) (No at Step S204), the process moves to a processing at Step S206.

If the read signal strength Speak<m, n> is higher than the maximal signal strength Speak_max<m, n> (Speak<m, n>>Speak_max<m, n>) (Yes at Step S204), the signal processor 44 replaces the maximal signal strength Speak_max<m, n> with the signal strength Speak<m, n> (Speak_max<m, n>=Speak<m, n>), and temporarily stores the replaced value in the storage 46 (Step S205).

The signal processor 44 then sets m=m+1 (Step S206) and determines whether m is M (m=M) (Step S207). If m is smaller than M (m<M) (No at Step S207), the process returns to the processing at Step S203.

If m reaches M (m=M) (Yes at Step S207), the signal processor 44 then sets n=n+1 (Step S208) and determines whether n is N (n=N) (Step S209). If n is smaller than N (n<N) (No at Step S209), the process returns to the processing at Step S203.

By repeating the above-described processes from Step S203 to Step S209 M×N times, the maximal signal strength Speak_max<m, n> in the detection area AA and the coordinate information on the partial detection area PAA from which the maximal signal strength Speak_max<m, n> has been acquired are temporarily stored in the storage 46.

If n reaches N (n=N) (Yes at Step S209), the signal processor 44 reads the maximal signal strength Speak_max<m, n> temporarily stored in the storage 46 (Step S210) and stores the coordinates of the partial detection area PAA from which the maximal signal strength Speak_max<m, n> has been acquired, in the storage 46, as signal strength maximum coordinates Smax(m, n) (Step S211).

The signal processor 44 sets a predetermined area including the signal strength maximum coordinates Smax(m, n) serving as the center coordinates thereof, as the biometric data acquisition area BAA (Step S212). The set biometric data acquisition area BAA is stored in the storage 46.

Referring back to FIG. 32, in a biometric data acquisition process (Step S125), the signal processor 44 reads the biometric data acquisition area BAA stored in the storage 46, and acquires the pulse wave data based on the detection signals Vdet detected in the partial detection areas PAA included in the biometric data acquisition area BAA.

When more than one of the biometric data acquisition areas BAA are set in the detection area AA, the signal processor 44 acquires the pulse wave data by averaging the detection signals Vdet output from the partial detection areas PAA in the biometric data acquisition areas BAA. As a result, improvement in quality of the pulse wave data can be expected.

As described above, the strength of the signal detected in each of the partial detection areas PAA in the detection area AA differs depending on the distribution of the subcutaneous blood vessels in the finger Fg of the subject. The detection device 1 of the present embodiment extracts the partial detection areas PAA in each of which the data having relatively larger signal strength is acquired in the detection area AA, and the detection device 1 acquires the pulse wave data based on the detection signals Vdet detected in the biometric data acquisition area BAA including the extracted partial detection areas PAA. As a result, the accurate pulse wave data can be acquired.

Modification 1

Figure 37:
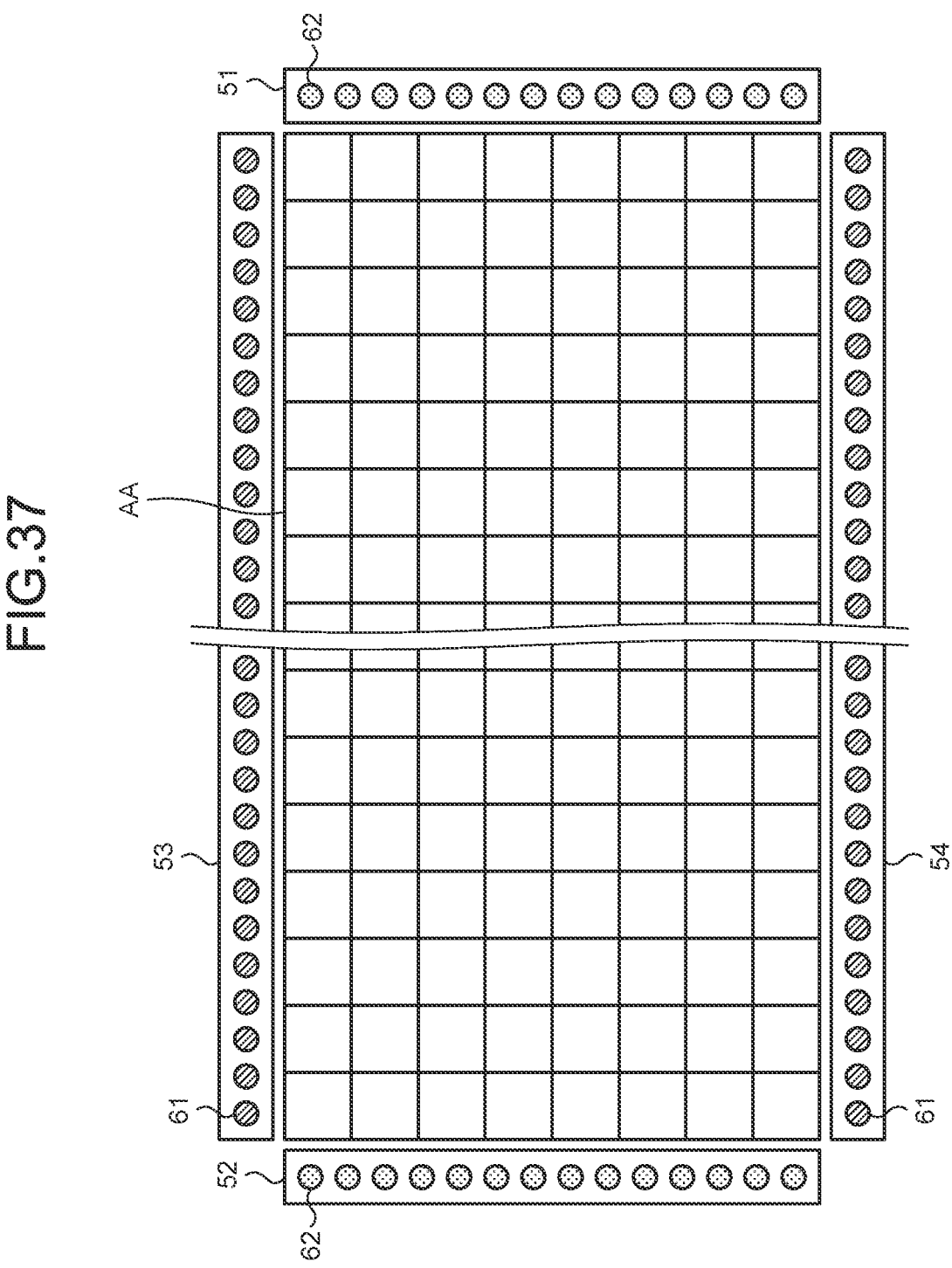
FIG. 37 is a plan view illustrating a modification of the arrangement of the light sources.

In the examples described with reference to FIGS. 20 and 24, the first and the second light sources 61 and 62 are provided at locations interposing the detection area AA of the sensor 10 therebetween, but the light sources may be provided around the detection area AA so as to surround the detection area AA. FIG. 37 is a plan view illustrating a modification of the arrangement of the light sources. Referring to FIG. 37, the first light source base member 51, the second light source base member 52, a third light source base member 53, and a fourth light source base member 54 are provided so as to surround the detection area AA. By providing the first and the second light sources 61 and 62 so as to surround the detection area AA, the light quantity to each portion of the detection area AA can be kept higher. As illustrated in FIG. 37, the second light sources 62 may be provided on the first and the second light source base members 51 and 52 facing each other, and the first light sources 61 may be provided on the third and the fourth light source base members 53 and 54 facing each other. The first and the second light sources 61 and 62 only need to be arranged around the optical sensors in this manner.

Modification 2

The detection area AA for detection by the optical sensors may be divided into a plurality of areas, and the processing by the light quantity controller 13 or the light quantity controller 13a may be performed for each of the divided areas. For example, as described with reference to FIG. 3, the block units PAG1 and PAG2 in the detection area AA may each be selected as the detection target. The processing can be performed more efficiently than when the entire detection area AA is selected as the detection target. When the peak coordinate acquirer 133 of the light quantity controller 13a has acquired the peak coordinates, the processing can be efficiently performed by detecting the biometric information using the block unit including the peak coordinates.

What is claimed is:

1. A detection device comprising:
a first light source configured to emit light having a predetermined wavelength;
a second light source configured to emit light having a wavelength different from that of the light emitted by the first light source;
a plurality of optical sensors provided at different locations from each other and configured to measure and detect the light emitted by the first light source and the second light source, the plurality of optical sensors configured to output detection values based on the detected light;
circuitry configured to set a light quantity of at least one of the first light source or the second light source so that a measurement value based on at least one of the detection values output by the optical sensors reaches a predetermined target value; and
a biometric information detector configured to, when the measurement value has reached the predetermined target value, detect information on a living body with the optical sensors using the light quantity for detecting biometric information set by the light quantity controller.

2. The detection device according to claim 1, wherein the circuitry comprises:
a first light quantity controller configured to increase the light quantity of the first light source until an average value of the measurement values based on the detection values of the optical sensors reaches the predetermined target value;
a second light quantity controller configured to increase the light quantity of the second light source until the average value of the measurement values based on the detection values of the optical sensors reaches the target value; and
a light quantity storage configured to, when the increased light quantity of the first light source and the increased light quantity of the second light source have each reached the predetermined target value, store the light quantity set by the first light quantity controller and the light quantity set by the second light quantity controller as the light quantities for detecting the biometric information.

3. The detection device according to claim 1, wherein the circuitry comprises:
a first light quantity controller configured to increase the light quantity of the first light source until the measurement value of an optical sensor in a predetermined coordinate position among the optical sensors reaches the predetermined target value;
a peak coordinate acquirer configured to, when the measurement value in the predetermined coordinate position has reached the target value, acquire a peak coordinate position where the measurement value is highest among those of the optical sensors;
a second light quantity controller configured to increase the light quantity of the second light source until the measurement value in the peak coordinate position acquired by the peak coordinate acquirer reaches the target value; and
a light quantity storage configured to, when the measurement value in the peak coordinate position has reached the target value, store the light quantity set by the first light quantity controller and the light quantity set by the second light quantity controller as the light quantities for detecting the biometric information.

4. The detection device according to claim 3, wherein the peak coordinate acquirer is configured to acquire, as the peak coordinate position, a position where amplitude of a pulse wave is largest.

5. The detection device according to claim 4, wherein the pulse wave has a frequency of from 0.5 Hz to 3 Hz.

6. The detection device according to claim 2, wherein the first light quantity controller and the second light quantity controller are configured to, when the measurement value does not reach the target value, reset a target value lower than the target value as a new target value, and then increase the light quantity.

7. The detection device according to claim 3, wherein the first light quantity controller and the second light quantity controller are configured to, when the measurement value does not reach the target value, reset a target value lower than the target value as a new target value, and then increase the light quantity.

8. The detection device according to claim 6, wherein the first light quantity controller and the second light quantity controller are configured to, when the measurement value has failed a predetermined number of times to reach the target value, reset the lower target value as the new target value.

9. The detection device according to claim 7, wherein the first light quantity controller and the second light quantity controller are configured to, when the measurement value has failed a predetermined number of times to reach the target value, reset the lower target value as the new target value.

10. The detection device according to claim 2, wherein a detection area for detection by the optical sensors is divided into a plurality of areas, and the first light quantity controller and the second light quantity controller are configured to perform the processing for each of the divided areas.

11. The detection device according to claim 3, wherein a detection area for detection by the optical sensors is divided into a plurality of areas, and the first light quantity controller and the second light quantity controller are configured to perform the processing for each of the divided areas.

12. The detection device according to claim 1, wherein the first light source is a light source configured to emit infrared light, and the second light source is a light source configured to emit red light.

13. The detection device according to claim 1, wherein the first light source and the second light source are disposed around the optical sensors.

14. The detection device according to claim 1, wherein the information on the living body detected by the biometric information detector is a blood oxygen saturation level.

15. The detection device according to claim 1, wherein the optical sensors are organic photodiodes.

16. The detection device according to claim 1, wherein the light quantity is a luminance.

\* \* \* \* \*